(12) United States Patent
Frey et al.

(10) Patent No.: US 9,562,892 B2
(45) Date of Patent: Feb. 7, 2017

(54) METHODS AND AGENTS FOR MODULATING PROTOCADHERIN-18 ACTIVITY

(71) Applicants: Alan B. Frey, Princeton, NJ (US); Edwin J. Vazquez-Cintron, New York, NY (US); Ngozi R. Monu, Jersey City, NJ (US); Jeremy C. Burns, New York, NY (US)

(72) Inventors: Alan B. Frey, Princeton, NJ (US); Edwin J. Vazquez-Cintron, New York, NY (US); Ngozi R. Monu, Jersey City, NJ (US); Jeremy C. Burns, New York, NY (US)

(73) Assignee: New York University, New York, NY (US)

( * ) Notice: Subject to any disclaimer, the term of this patent is extended or adjusted under 35 U.S.C. 154(b) by 542 days.

(21) Appl. No.: 14/044,087

(22) Filed: Oct. 2, 2013

(65) Prior Publication Data
US 2014/0094382 A1 Apr. 3, 2014

Related U.S. Application Data

(60) Provisional application No. 61/708,901, filed on Oct. 2, 2012.

(51) Int. Cl.
*C40B 30/06* (2006.01)
*G01N 33/50* (2006.01)
(Continued)

(52) U.S. Cl.
CPC ......... *G01N 33/5041* (2013.01); *C12Q 1/6809* (2013.01); *G01N 33/505* (2013.01);
(Continued)

(58) Field of Classification Search
None
See application file for complete search history.

(56) References Cited

U.S. PATENT DOCUMENTS 7,105,328 B2   9/2006   Wood et al.
7,700,301 B2   4/2010   Wood et al.

OTHER PUBLICATIONS

Frey, et al., "Effector-phase tolerance: another mechanism of how cancer escapes antitumor immune response", J Leukoc Biol, 2006; 79: 652-662.
(Continued)

*Primary Examiner* — Christian Boesen
(74) *Attorney, Agent, or Firm* — Klauber & Jackson LLC

(57) ABSTRACT

Screening assays and methods of using same for screening to identify modulator agents or compounds that affect pcdh18 mediated inhibition of T cell effector function are described herein. Pharmaceutical and immunogenic compositions comprising agents or compounds that modulate pcdh18 mediated inhibition of T cell effector function are also encompassed. Methods for modulating pcdh18 mediated inhibition of T cell effector function using agents identified using assays described herein in pharmaceutical and immunogenic compositions are also envisioned. Adenocarcinoma is an exemplary tumor type that expresses pcdh18 and for which such pharmaceutical and immunogenic compositions would confer benefit to patients. Also encompassed are methods for reducing pcdh18 mediated inhibition of T cell effector function so as to achieve more effective T cell responses to pcdh18 expressing tumors.

7 Claims, 19 Drawing Sheets

(51) Int. Cl.
 G01N 33/68 (2006.01)
 C12Q 1/68 (2006.01)
 G01N 33/566 (2006.01)
(52) U.S. Cl.
 CPC ....... *G01N 33/566* (2013.01); *G01N 33/6872* (2013.01); *C12Q 2600/136* (2013.01); *C40B 30/06* (2013.01)

(56) References Cited

OTHER PUBLICATIONS

Monu, et al., "Suppression of proximal T cell receptor signaling and lytic function in CD8+ tumor-infiltrating T cells", Cancer Res, 2007; 67: 11447-11454.
Radoja, et al., "CD8+ tumor-infiltrating lymphocytes are primed for Fas-mediated activation-induced cell death but are not apoptotic in situ", J. Immunol, 2001; 166: 6074-6083.
Koneru, et al., "Defective proximal TCR signaling inhibits CD8+ tumor infiltrating lymphocyte lytic function", J. Immunol., 2005, 174: 1830-1840.
Homayouni, et al., ., "Disabled-1 interacts with a novel developmentally regulated protocadherin", Biochem. Biophys. Res. Commun, 2001; 289: 539-547.
Ma, et al., "Protein kinase Cdelta regulates antigen receptor-induced lytic granule polarization in mouse CD8+ CTL", J. Immunol., 2007; 178: 7814-7821.
Koneru, et al., , "Defective adhesion in tumor infiltrating CD8+ T cells", J. Immunol, 2006; 176: 6103-6111.
Vazquez-Cintron, et al., "Tumor-induced disruption of proximal TCR-mediated signal transduction in tumor-infiltrating CD8+ lymphocytes inactivates antitumor effector phase", J. Immunol., 2010; 185: 7133-7140.
Vivier, et al., , "Inhibitory NK-cell receptors on T cells: witness of the past, actors of the future", Nat. Rev. Immunol, 2004; 4: 190-198.
Blackburn, et al., , "Coregulation of CD8+ T cell exhaustion by multiple inhibitory receptors during chronic viral infection", Nat. Immunol, 2009; 10: 29-37.
Aamar, et al., "Protocadherin-18a has a role in cell adhesion, behavior and migration in zebrafish development", Dev. Biol., 2008; 318: 335-346.
Newman, et al., "Inhibition of antigen-receptor signaling by Platelet Endothelial Cell Adhesion Molecule-1 (DS31) requires functional ITIMs, SHP-2, and p56ck", Blood, 2001; 97: 2351-2357.
Zou, et al., ., "Inhibitory B7-family molecules in the tumour microenvironment", Nat. Rev. Immunol, 2008; 8: 467-477.
Vazquez-Cintron et al., "Protocadherin-18 Is a Novel Differentiation Marker and an Inhibitory Signaling Receptor for CD8+ Effector Memory T Cells", PLoS One, 2012, 7:e36101.

Vazquez et al, supplement fig 9

Figure 9A

Homo sapiens protocadherin 18 (PCDH18), mRNA
NCBI Reference Sequence: NM_019035.3

GenBank Graphics

```
>gi|156630996|ref|NM_019035.3| Homo sapiens protocadherin 18 (PCDH18), mRNA
GCAATCACGGGTGTTTAGTCTGCAGCCGAGCAGCTAAAGGGAGAAAGAATCGCTCAGGAAAGACACACTG
CAGACTCCACCGGCACCCTGCAATAGATGGATTCCGACTACACAAGGGAGAAAACGCGGAGGTGACACTC
TCCTGCCTGGAAAGAGGACGAACGACCAAACAAACGCAAGGACTGGACTCCATGCCGAAGGTATCTGGAA
GTCGTGACACGGTGTGTATAAAACAAAAGTTTGCGAGCTGTTAATTGCTGTGCTGTGTTATTAAGAGACG
CTTTCAAGTTTCAAGTACCAAATGTAGCTTTACGTTGCCAAAGGAAGTTGAGGCAATTGCTTTGCTGTTT
TAACTTGCTCTGTGAGGGAAATCTCATAAACTGACCAATGCACCAAATGAATGCTAAAATGCACTTTAGG
TTTGTTTTTGCACTTCTGATAGTATCTTTCAACCACGATGTACTGGGCAAGAATTTGAAATACAGGATTT
ATGAGGAACAGAGGGTTGGATCAGTAATTGCAAGACTATCAGAGGATGTGGCTGATGTTTTATTGAAGCT
TCCTAATCCTTCTACTGTTCGATTTCGAGCCATGCAGAGGGGAAATTCTCCTCTACTTGTAGTAAACGAG
GATAATGGGGAAATCAGCATAGGGGCTACAATTGACCGTGAACAACTGTGCCAGAAAAACTTGAACTGTT
CCATAGAGTTTGATGTGATCACTCTACCCACAGAGCATCTGCAGCTTTTCCATATTGAAGTTGAAGTGCT
GGATATTAATGACAATTCTCCCCAGTTTTCAAGATCTCTCATACCTATTGAGATATCTGAGAGTGCAGCA
GTTGGGACTCGCATTCCCCTGGACAGTGCATTTGATCCAGATGTTGGGGAAAATTCCCTCCACACATACT
CGCTCTCTGCCAATGATTTTTTTAATATCGAGGTTCGGACCAGGACTGATGGAGCCAAGTATGCAGAACT
CATAGTGGTCAGAGAGTTAGATCGGGAGCTGAAGTCAAGCTACGAGCTTCAGCTCACTGCCTCAGACATG
GGAGTACCTCAGAGGTCTGGCTCATCCATACTAAAAATAAGCATTTCAGACTCCAATGACAACAGCCCTG
CTTTTGAGCAGCAATCTTATATAATACAACTCTTAGAAAACTCCCCGGTTGGCACTTTGCTCTTAGATCT
GAATGCCACGGATCCAGATGAGGGCGCTAATGGGAAAATTGTATATTCCTTCAGCAGTCATGTGTCTCCC
AAAATTATGGAGACTTTTAAAATTGATTCTGAAAGAGGACATTTGACTCTTTTCAAGCAAGTGGATTATG
AAATCACCAAATCCTATGAGATTGATGTTCAGGCTCAAGATTTGGGTCCAAATTCAATCCCAGCCCATTG
CAAAATTATAATTAAGGTTGTGGATGTTAATGACAATAAACCTGAAATTAACATCAACCTCATGTCCCCT
GGAAAAGAAGAAATATCTTATATTTTTGAAGGGGATCCTATTGATACATTTGTTGCTTTGGTCAGAGTTC
AGGACAAGGATTCTGGGCTGAATGGAGAAATAGTTTGTAAGCTTCATGGACATGGTCACTTTAAACTTCA
GAAGACATATGAAAACAATTATTTAATCTTAACTAATGCCACACTGGATAGAGAAAGAGATCTGAGTAT
AGTTTGACTGTAATCGCTGAGGACAGGGGGACACCCAGTCTCTCTACAGTGAAACATTTTACAGTTCAAA
TCAATGATATCAATGACAATCCACCCCACTTCCAGAGAAGCCGATATGAATTTGTAATTTCAGAAAATAA
CTCACCAGGGGCATATATCACCACTGTTACAGCCACAGATCCTGATCTTGGAGAAAATGGGCAAGTGACA
TACACCATCTTGGAGAGTTTTATTCTAGGAAGTTCCATAACTACATATGTAACCATTGACCCATCTAATG
GAGCCATCTATGCCCTCAGAATCTTTGATCATGAAGAAGTGAGTCAGATCACTTTTGTGGTAGAAGCAAG
AGATGGAGGAAGCCCGAAGCAACTGGTAAGCAATACCACAGTTGTGCTCACCATCATTGACGAAAATGAC
AACGTTCCTGTGGTTATAGGGCCTGCATTGCGTAATAATACGGCAGAAATCACCATTCCCAAAGGGGCTG
AAAGTGGCTTTCATGTCACAAGAATAAGGGCAATTGACAGAGACTCTGGTGTGAATGCTGAACTCAGCTG
CGCCATAGTAGCAGGTAATGAGGAGAATATCTTCATAATTGATCCACGATCATGTGACATCCATACCAAC
GTTAGCATGGATTCTGTTCCCTACACAGAATGGGAGCTGTCAGTTATCATTCAGGACAAAGGCAATCCTC
AGCTACATACCAAAGTCCTTCTGAAGTGCATGATCTTTGAATATGCAGAGTCGGTGACAAGTACAGCAAT
GACTTCAGTAAGCCAGGCATCCTTGGATGTCTCCATGATAATAATTATTTCCTTAGGAGCAATTTGTGCA
GTGTTGCTGGTTATTATGGTGCTATTTGCAACTAGGTGTAACCGCGAGAAGAAAGACACTAGATCCTATA
```

Figure 9A (cont)

```
ACTGCAGGGTGGCCGAATCAACTTACCAGCACCACCCAAAAAGGCCATCCCGGCAGATTCACAAAGGGGA
CATCACATTGGTGCCTACCATAAATGGCACTCTGCCCATCAGATCTCATCACAGATCGTCTCCATCTTCA
TCTCCTACCTTAGAAAGAGGGCAGATGGGCAGCCGGCAGAGTCACAACAGTCACCAGTCACTCAACAGTT
TGGTGACAATCTCATCAAACCACGTGCCAGAGAATTTCTCATTAGAACTCACCCACGCCACTCCTGCTGT
TGAGCAGGTCTCTCAGCTTCTTTCAATGCTTCACCAGGGGCAATATCAGCCAAGACCAAGTTTTCGAGGA
AACAAATATTCCAGGAGCTACAGATATGCCCTTCAAGACATGGACAAATTTAGCTTGAAAGACAGTGGCC
GTGGTGACAGTGAGGCAGGAGACAGTGATTATGATTTGGGGCGAGATTCTCCAATAGATAGGCTGTTGGG
TGAAGGATTCAGCGACCTGTTTCTCACAGATGGAAGAATTCCAGCAGCTATGAGACTCTGCACGGAGGAG
TGCAGGGTCCTGGGACACTCTGACCAGTGCTGGATGCCACCACTGCCCTCACCGTCTTCTGATTATAGGA
GTAACATGTTCATTCCAGGGGAAGAATTCCCAACGCAACCCCAGCAGCAGCATCCACATCAGAGTCTTGA
GGATGACGCTCAGCCTGCAGATTCCGGTGAAAAGAAGAAGAGTTTTTCCACCTTTGGAAAGGACTCCCCA
AACGATGAGGACACTGGGGATACCAGCACATCATCTCTGCTCTCGGAAATGAGCAGTGTGTTCCAGCGTC
TCTTACCGCCTTCCCTGGACACCTATTCTGAATGCAGTGAGGTGGATCGGTCCAACTCCCTGGAGCGCAG
GAAGGGACCCTTGCCAGCCAAAACTGTGGGTTACCCACAGGGGGTAGCGGCATGGGCAGCCAGTACGCAT
TTTCAAAATCCCACCACCAACTGTGGGCCGCCACTTGGAACTCACTCCAGTGTGCAGCCTTCTTCAAAAT
GGCTGCCAGCCATGGAGGAGATCCCTGAAAATTATGAGGAAGATGATTTTGACAATGTGCTCAACCACCT
CAATGATGGGAAACACGAACTCATGGATGCCAGTGAACTGGTGGCAGAGATTAACAAACTGCTTCAAGAT
GTCCGCCAGAGCTAGGAGATTTTAGCGAAGCATTTTGTTTCCATGTATATGGAAATAGGGAACAACAAC
AACAACAAAAACCCTGAAAGAACTGGCATTGCCAAATAGTTGCATTTATCATAAATGTGTCTGTGTATA
TTGAATATTAAATACTGTATTTTCGTATGTACACAATGCAAGTGTGATTATTTTAATCTGTATTTTAAAA
ATACATTTGTACCTTATATTTATGTGTAATTTAACAAACAAATTTTATTTTTTACTCCCATGACAGACA
TGTTTTTCCTAGTCGTGTAGAAACTAGCCACTGTTCAAATCTGATACACTATTCAACCACAAAGTGTAAA
GGCACTGCTTAGATTAGTTTTGTTGGGGAAGAATTATTATGTTGTATGAACAACCCCACTGAAGCATTAT
ACAATTCTTAATTCCATTAAGTGATCCCACTTTTTTTCAATAACTTTTTAGAAATTAAGAATCATTAAAA
TTGTTAAGCTATTTTATTGTTATTTTCTCTACTTTCTACTAGCCCCAATAGTTGAACTCTTATAGGAAAA
TCGAAAGATAAAGTGAAAGTTTATTTCAGGACTGAGAAATATCTTGAAGGTTATTTATTAGATGACTATC
TCAAATGAACTTTTTATAGACAATGATGAAAACAGAATTAAAGTCAATGTTTCCTGACTCCAGGCCCCT
ACTATTCCAGGCCATCACACTGGCCTGTTCCGGAGAATATTTCTCTCACAATATTATTATCTACTTATAA
TTATGGTAAACAATAAATTTTATTCCATCCTTGTAGTATGAAACATGCTCCAAGGAAATGGAATCTGTCC
TTTAAATGGATAACAGTATGTGTTCTAATGGCATAAAATATTACTGGATAAAAACAGTTGTGTCAGTGTC
TCTCCTAAGGTAGTAAATATAATTGACTTATTCTGAACCCATTCTATTTTGAATCTCCCCTTTCCTCTCA
CAATACTTGAACATTTTAATCTTTTGGAATATTGTCTTTCTTTGTTATAACTATTCATTTTTAGCTTTTG
TCTCCAGTGCATGATCTCATATTTTTGCTTTTATTTTTAGTATAAGAACATTTATAAAATCATATTTTTG
TTACTGCAATTGTTTTATTTGTTGTGTGGCAAATGAGAAATCCTTTATTTATTGTGCTGTGATCTCTCTG
TGTGGAATGCCTTGGTGAGAGAGATGCTTATTATGACTATTATCATTTCTGACCAAGCTTCTATTAATGT
TATTTCTAATAATACACTATCTTGATTGTACTCTCCAGAAAATTTTCTGTCAGTGAAAATAAAAGAAAA
ATTAAAGTAAAGCTAAGGAACTGTCTATAAGTCAGAGTCCTGTTCCTACATATTTGTTCAAAAGCTTGGC
ATGCAGCAGGCCCTTCCTGAGCGGGTGATTCAGTGTTGAGTTTCAAATAATAAACAGGCAGCATTCAGTT
GGCTGGGCGAACAAGAAAAACACAATGGAAAAGGAATGAGTTTGAGACTTGTAATGGGAATGAAAGTAGT
AAGCCATATTCCAGCTAAATAAGTTAAATGCATTTGGGGAATAAAGAAAAAGAGTAAGCAAGCAATAAT
TGCTTGAATATTTTTCAAATTACAACAAAAAAAAATACTTTCTTAGGACATTTTGTATTAAATTGTGCAG
```

Figure 9A (cont)

```
GATAAAAAGGTATCCTTACAATGTTTCCAGGAGGCAAGAATATTATCGTCCCTGGCTTGCTAGTCAGGAA
TTGAAACACTGGGAAAGTTAAGTAACTGAAAAGTGACTAAAATTCAGATATTTGAATTCTCAAATGAGTA
CCACATTAAATAGAATATATTACCTCTTTCAACAGGCACATTTTCCTTTATAGGAGAGATTGCAATTACA
AGTGAAATTTCAGTATATTTTTCAGTAGATTACACACACAAACGCTAACCATATTTAAATGCATTCTGCC
TTTCAACTTCACTTCCTTTCAGTATATATTACCATTAAGAAAAGACTTTTATATCCTCACTGTTCTTAA
TTAAAGCACCAGCAGTAATATGGGAAGCTATGCTGAAAACCGCTATTTTGAATAATGTGAAATAAATAA
AATGCAATATTTCATTCAACACAAAA
```

Figure 9B

PCDH18 protein [Homo sapiens]

GenBank: AAI43362.1

GenPept Graphics

\>gi|219519457|gb|AAI43362.1| PCDH18 protein [Homo sapiens]
MHQMNAKMHFRFVFALLIVSFNHDVLGKNLKYRIYEEQRVGSVIARLSEDVADVLLKLPNPSTVRFRAMQ
RGNSPLLVVNEDNGEISIGATIDREQLCQKNLNCSIEFDVITLPTEHLQLFHIEVEVLDINDNSPQFSRS
LIPIEISESAAVGTRIPLDSAFDPDVGENSLHTYSLSANDFFNIEVRTRTDGAKYAELIVVRELDREIKS
SYELQLTASDMGVPQRSGSSILKISISDSNDNSPAFEQQSYIIQLLENSPVGTLLLDLNATDPDEGANGK
IVYSFSSHVSPKIMETFKIDSERGHLTLFKQVDYEITKSYEIDVQAQDLGPNSIPAHCKIIIKVVDVNDN
KPEININLMSPGKEEISYIFEGDPIDTFVALVRVQDKDSGLNGEIVCKLHGHGHFKLQKTYENNYLILTN
ATLDREKRSEYSLTVIAEDRGTPSLSTVKHFTVQINDINDNPPHFQRSRYEFVISENNSPGAYITTVTAT
DPDLGENGQVTYTILESFILGSSITTYVTIDPSNGAIYALRIFDHEEVSQITFVVEARDGGSPKQLVSNT
TVVLTIIDENDNVPVVIGPALRNNTAEITIPKGAESGFHVTRIRAIDRDSGVNAELSCAIVAGNEENIFI
IDPRSCDIHTNVSMDSVPYTEWELSVIIQDKGNPQLHTKVLLKCMIFEYAESVTSTAMTSVSQASLD
VSMIIISLGAICAVLLVIMVLF
ATRCNREKKDTRSYNCRVAESTYQHHPKRPSRQIHKGDITLVPTINGTLP
IRSHHRSSPSSSPTLERGQMGSPQSHNSHQSLNSLVTISSNHVPENFSLELTHATPAVEVSQLLSMLHQG
QY*QPRPSFRGNKYSRSYRYALQDMDKFSLKDSGRGDSEAGDSDYDLGRDSPIDRLLGEGFSDLFLTDGRI
PAAMRLCTEECRVLGHSDQCWMPPLPSPSSDYRSNMFIPGEEFPTQPQQQHPHQSLEDDAQPADSGEKKK
SFSTFGKDSPNDEDTGDTSTSSLLSEMSSVFQRLLPPSLDTYSECSEVDRSNSLERRKGPLPAKTVGYPQ
GVAAWAASTHFQNPTTNCGPPLGTHSSVQPSSKWLPAMEEIPENYEEDDFDNVLNHLNDGKHELMDASEL
VAEINKLLQDVRQS

Figure 10A

*ED1 nucleotide*
TACAGGATTTATGAGGAACAGAGGGTTGGATCAGTAATTGCAAGACTATCAGAGGA
TGTGGCTGATGTTTTATTGAAGCTTCCTAATCCTTCTACTGTTCGATTTCGAGCCATG
CAGAGGGGAAATTCTCCTCTACTTGTAGTAAACGAGGATAATGGGGAAATCAGCAT
AGGGGCTACAATTGACCGTGAACAACTGTGCCAGAAAAACTTGAACTGTTCCATAG
AGTTTGATGTGATCACTCTACCCACAGAGCATCTGCAGCTTTTCCATATTGAAGTTG
AAGTGCTGGATATTAATGACAAT

Figure 10B

*ED1 amino acid*
YRIYEEQRVGSVIARLSEDVADVLLKLPNPSTVRFRAMQRGNSPLLVVNEDNGEISIGAT
IDREQLCQKNLNCSIEFDVITLPTEHLQLFHIEVEVLDINDN

Figure 10C

*ED5 nucleotide*
TATGAATTTGTAATTTCAGAAAATAACTCACCAGGGGCATATATCACCACTGTTACA
GCCACAGATCCTGATCTTGGAGAAAATGGGCAAGTGACATACACCATCTTGGAGAG
TTTTATTCTAGGAAGTTCCATAACTACATATGTAACCATTGACCCATCTAATGGAGC
CATCTATGCCCTCAGAATCTTTGATCATGAAGAAGTGAGTCAGATCACTTTTGTGGT
AGAAGCAAGAGATGGAGGAAGCCCGAAGCAACTGGTAAGCAATACCACAGTTGTG
CTCACCATCATTGACGAAAATGACAAC

Figure 10D

*ED5 amino acid*
YEFVISENNSPGAYITTVTATDPDLGENGQVTYTILESFILGSSITTYVTIDPSNGAIYALRI
FDHEEVSQITFVVEARDGGSPKQLVSNTTVVLTIIDENDN

Figure 10E

*Nucleotide from start Methionine to EC5*
TAACTTGCTCTGTGAGGGAAATCTCATAAACTGACCAATGCACCAAATGAATGCTAA
AATGCACTTTAGGTTTGTTTTTGCACTTCTGATAGTATCTTTCAACCACGATGTACTG
GGCAAGAATTTGAAATACAGGATTTATGAGGAACAGAGGGTTGGATCAGTAATTGC
AAGACTATCAGAGGATGTGGCTGATGTTTATTGAAGCTTCCTAATCCTTCTACTGTT
CGATTTCGAGCCATGCAGAGGGGAAATTCTCCTCTACTTGTAGTAAACGAGGATAAT
GGGGAAATCAGCATAGGGGCTACAATTGACCGTGAACAACTGTGCCAGAAAAACTT
GAACTGTTCCATAGAGTTTGATGTGATCACTCTACCCACAGAGCATCTGCAGCTTTT
CCATATTGAAGTTGAAGTGCTGGATATTAATGACAATTCTCCCCAGTTTTCAAGATC
TCTCATACCTATTGAGATATCTGAGAGTGCAGCAGTTGGGACTCGCATTCCCCTGGA
CAGTGCATTTGATCCAGATGTTGGGGAAAATTCCCTCCACACATACTCGCTCTCTGC
CAATGATTTTTTAATATCGAGGTTCGGACCAGGACTGATGGAGCCAAGTATGCAGA
ACTCATAGTGGTCAGAGAGTTAGATCGGGAGCTGAAGTCAAGCTACGAGCTTCAGC
TCACTGCCTCAGACATGGGAGTACCTCAGAGGTCTGGCTCATCCATACTAAAAATAA
GCATTTCAGACTCCAATGACAACAGCCCTGCTTTTGAGCAGCAATCTTATATAATAC
AACTCTTAGAAAACTCCCCGGTTGGCACTTTGCTCTTAGATCTGAATGCCACGGATC
CAGATGAGGGCGCTAATGGGAAAATTGTATATTCCTTCAGCAGTCATGTGTCTCCCA
AAATTATGGAGACTTTTAAAATTGATTCTGAAAGAGGACATTTGACTCTTTTCAAGC
AAGTGGATTATGAAATCACCAAATCCTATGAGATTGATGTTCAGGCTCAAGATTTGG
GTCCAAATTCAATCCCAGCCCATTGCAAAATTATAATTAAGGTTGTGGATGTTAATG
ACAATAAACCTGAAATTAACATCAACCTCATGTCCCCTGGAAAAGAAGAAATATCTT
ATATTTTTGAAGGGGATCCTATTGATACATTTGTTGCTTTGGTCAGAGTTCAGGACA
AGGATTCTGGGCTGAATGGAGAAATAGTTTGTAAGCTTCATGGACATGGTCACTTTA
AACTTCAGAAGACATATGAAAACAATTATTTAATCTTAACTAATGCCACACTGGATA
GAGAAAAGAGATCTGAGTATAGTTTGACTGTAATCGCTGAGGACAGGGGGACACCC
AGTCTCTCTACAGTGAAACATTTTACAGTTCAAATCAATGATATCAATGACAATCCA
CCCCACTTCCAGAGAAGCCGATATGAATTTGTAATTTCAGAAAATAACTCACCAGGG
GCATATATCACCACTGTTACAGCCACAGATCCTGATCTTGGAGAAAATGGGCAAGTG
ACATACACCATCTTGGAGAGTTTTATTCTAGGAAGTTCCATAACTACATATGTAACC
ATTGACCCATCTAATGGAGCCATCTATGCCCTCAGAATCTTTGATCATGAAGAAGTG
AGTCAGATCACTTTTGTGGTAGAAGCAAGAGATGGAGGAAGCCCGAAGCAACTGGT
AAGCAATACCACAGTTGTGCTCACCATCATTGACGAAAATGACAAC

Figure 10F

*Amino acid sequence of ED1 to ED6*

MHQMNAKMHFRFVFALLIVSFNHDVLGKNLK<u>YRIYEEQRVGSVIARLSEDVADVLLKL</u>
<div align="right">ED1</div>
<u>PNPSTVRFRAMQRGNSPLLVVNEDNGEISIGATIDREQLCQKNLNCSIEFDVITLPTEHLQ</u>

<u>LFHIEVEVLDINDNSPQFSRSLIP</u><u>IEISESAAVGTRIPLDSAFDPDVGENSLHTYSLSANDFF</u>
<div align="right">ED2</div>
<u>NIEVRTRTDGAKYAELIVVRELDRELKSSYELQLTASDMGVPQRSGSSILKISISDSNDNS</u>

<u>PAFEQQ</u><u>SYIIQLLENSPVGTLLLDLNATDPDEGANGKIVYSFSSHVSPKIMETFKIDSERG</u>
<div align="right">ED3</div>

<u>HLTLFKQVDYEITKSYEIDVQAQDLGPNSIPAHCKIIIKVVDVNDNKPEININLMSPGKEEI</u>

<u>SY</u><u>IFEGDPIDTFVALVRVQDKDSGLNGEIVCKLHGHGHFKLQKTYENNYLILTNATLDRE</u>
<div align="right">ED4</div>

<u>KRSEYSLTVIAEDRGTPSLSTVKHFTVQINDINDNPPHFQRSR</u><u>YEFVISENNSPGAYITTVT</u>
<div align="right">ED5</div>

<u>ATDPDLGENGQVTYTILESFILGSSITTYVTIDPSNGAIYALRIFDHEEVSQITFVVEARDG</u>

<u>GSPKQLVSNTTVVLTIIDENDNVPVVIGPALRNNTA</u><u>EITIPKGAESGFHVTRIRAIDRDSGV</u>
<div align="right">ED6</div>

<u>NAELSCAIVAGNEENIFIIDPRSCDIHTNVSMDSVPYTEWELSVIIQDKGNPQLHTKVLLK</u>

<u>CMIFEYAESVTSTAMTSVSQASLD</u>

Figure 10G

Protocadherin-18
Human Nucleotide acid sequence that encodes ED1 to ED6

ATGCACCAAATGAATGCTAAAATGCACTTTAGGTTTGTTTTGCACTTCTG
ATAGTATCTTTCAACCACGATGTACTGGGCAAGAATTTGAAATACAGGAT
TTATGAGGAACAGAGGGTTGGATCAGTAATTGCAAGACTATCAGAGGATG
TGGCTGATGTTTTATTGAAGCTTCCTAATCCTTCTACTGTTCGATTTCGAGC
CATGCAGAGGGGAAATTCTCCTCTACTTGTAGTAAACGAGGATAATGGGG
AAATCAGCATAGGGGCTACAATTGACCGTGAACAACTGTGCCAGAAAAAC
TTGAACTGTTCCATAGAGTTTGATGTGATCACTCTACCCACAGAGCATCTG
CAGCTTTTCCATATTGAAGTTGAAGTGCTGGATATTAATGACAATTCTCCC
CAGTTTTCAAGATCTCTCATACCTATTGAGATATCTGAGAGTGCAGCAGTT
GGGACTCGCATTCCCCTGGACAGTGCATTTGATCCAGATGTTGGGGAAAA
TTCCCTCCACACATACTCGCTCTCTGCCAATGATTTTTTAATATCGAGGTT
CGGACCAGGACTGATGGAGCCAAGTATGCAGAACTCATAGTGGTCAGAGA
GTTAGATCGGGAGCTGAAGTCAAGCTACGAGCTTCAGCTCACTGCCTCAG
ACATGGGAGTACCTCAGAGGTCTGGCTCATCCATACTAAAAATAAGCATT
TCAGACTCCAATGACAACAGCCCTGCTTTTGAGCAGCAATCTTATATAATA
CAACTCTTAGAAACTCCCCGGTTGGCACTTTGCTCTTAGATCTGAATGCC
ACGGATCCAGATGAGGGCGCTAATGGGAAAATTGTATATTCCTTCAGCAG
TCATGTGTCTCCCAAAATTATGGAGACTTTTAAAATTGATTCTGAAAGAGG
ACATTTGACTCTTTTCAAGCAAGTGGATTATGAAATCACCAAATCCTATGA
GATTGATGTTCAGGCTCAAGATTTGGGTCCAAATTCAATCCCAGCCCATTG
CAAAATTATAATTAAGGTTGTGGATGTTAATGACAATAAACCTGAAATTA
ACATCAACCTCATGTCCCTGGAAAAGAAGAAATATCTTATATTTTTGAAG
GGGATCCTATTGATACATTTGTTGCTTTGGTCAGAGTTCAGGACAAGGATT
CTGGGCTGAATGGAGAAATAGTTTGTAAGCTTCATGGACATGGTCACTTTA
AACTTCAGAAGACATATGAAACAATTATTTAATCTTAACTAATGCCACA
CTGGATAGAGAAAGAGATCTGAGTATAGTTTGACTGTAATCGCTGAGGA
CAGGGGGACACCCAGTCTCTCTACAGTGAAACATTTTACAGTTCAAATCA
ATGATATCAATGACAATCCACCCCACTTCCAGAGAAGCCGATATGAATTT
GTAATTTCAGAAAATAACTCACCAGGGGCATATATCACCACTGTTACAGC
CACAGATCCTGATCTTGGAGAAATGGGCAAGTGACATACACCATCTTGG
AGAGTTTTATTCTAGGAAGTTCCATAACTACATATGTAACCATTGACCCAT

Figure 10G (cont)

CTAATGGAGCCATCTATGCCCTCAGAATCTTTGATCATGAAGAAGTGAGTC
AGATCACTTTTGTGGTAGAAGCAAGAGATGGAGGAAGCCCGAAGCAACTG
GTAAGCAATACCACAGTTGTGCTCACCATCATTGACGAAAATGACAACGT
TCCTGTGGTTATAGGGCCTGCATTGCGTAATAATACGGCAGAAATCACCAT
TCCCAAAGGGGCTGAAAGTGGCTTTCATGTCACAAGAATAAGGGCAATTG
ACAGAGACTCTGGTGTGAATGCTGAACTCAGCTGCGCCATAGTAGCAGGT
AATGAGGAGAATATCTTCATAATTGATCCACGATCATGTGACATCCATACC
AACGTTAGCATGGATTCTGTTCCCTACACAGAATGGGAGCTGTCAGTTATC
ATTCAGGACAAAGGCAATCCTCAGCTACATACCAAAGTCCTTCTGAAGTG
CATG

Figure 11A

Gene ID for 73173 (Pcdh18) using NCBI data base from the NIH
Chromosomal Locations for CCDS 17334.1

Nucleotide ID
NCBI: NM_130448.3

ATGCACCAAATGAATACTAAAATGCACTTTAGATTTGCACTTGCACTTCTGATGGCGTTTTTCAGCCAC
GATGTCCTGGCTAAGAATCTGAAATACAGGATTTATGAGGAGCAGAGGGTCGGATCGGTAATTGCTAG
ACTATCAGAAGATGTGGCTGATGTTTTATTGAAGCTACCAAATCCTTCTGCTGTTCGTTTTCGAGCCAT
GCCACGGGGGAATTCTCCTCTCCTGGTCGTAAATGAGAATACCGGAGAAATCAGCATAGGGGCTAAA
ATTGACCGCGAGCAACTATGCCAAAAAAACTTGAACTGTTCGATAGAGTTTGATGTGCTCACTCTGCC
GACCGAGCATCTGCAGCTGTTCCACATTGAAGTGGACGTGCTGGACATTAATGACAATTCCCCCCAAT
TCTCGAGACCCGTCATTCCCATTGAGATATCGGAGAGCGCAGCAGTTGGGACTCGTATCCCCCTGGAC
AGTGCGTTCGACCCAGATGTTGGGGAAAATTCCCTCCACACCTACTCGCTCTCTGCTAATGATTATTTT
AATATCGAAGTGCGAACCAGGACAGACGGGGCCAAGTACGCTGAACTCATAGTGGTGAAAGAGTTGG
ATCGGGAGCTGAAGGCTAGCTACGAGCTTCAGCTCACCGCCTCCGACATGGGAGTGCCTCAGAGGTCT
GGCTCCTCCATCCTGAAAATCAGCATTTCGGATTCCAACGACAACAGCCCGGCCTTTGAGCAGCCTTCT
TACACAATACAACTCTTAGAAAACTCCCCAGTTGGAACCTTGCTCCTTGATCTAAATGCCACCGATCCA
GATGAGGGCGCTAATGGGAGAATTGTGTATTCTTTCAGCAGTCATGTGTCTCCCAAAATTATAGAGAC
TTTTAAGATCGACTCAGAAAAAGGCCACTTGACTCTTTTCAAGCCAGTGGATTATGAAATCACCAAGT
CCTATGAGATAGACGTTCAAGCCCAAGATTTGGGTCCCAATTCCATTCCTGCTCATTGCAAAATTATAA
TTAAGGTTGTGGATGTCAATGACAATAAACCTGAAATTAGCATAAATCTCATGTCCCCTGGAAAAGAA
GAAGTATCTTATGTCTTTGAAGGGGATCCCATTGATACATTCGTTGCTATCGTCAGGGTTCAAGACAAG
GATTCTGGGCTGAATGGGGAAATAATCTGTAAGCTTCATGGGCATGGACATTTTAAACTTCAGAAGAC
ATATGAAAATAACTACTTGATCTTGACCAATGCCACTCTGGATAGAGAAAAGAGATCTGAGTATAGTT
TGACTGTGATTGCTGAGGACAAGGGAACACCAAGCCTCTCCTCAGTGAGACATTTTACTGTTCAAATC
AATGACATAAATGACAATCCACCTCGCTTCCAGAGGAGCCGATATGAATTTGTCATCTCAGAGAATAA
TTCACCAGGGGCGTATATCACCACAGTTACAGCCACTGATCCAGATCTTGGTGAAAACGGACATGTGA
CATACACCATTTTGGAGAGTTTTGTCTTGGGAAGTTCCATCACCACGTATGTAACCATTGACCCCTCTA
ATGGCGCCATCTATGCCCTCAGGATCTTTGATCATGAAGAAGTGAGTCAGATCACTTTTGTGGTGGAA
GCCAGGGATGGAGGGAGTCAGAAGCAACTCTCCAGCAACACCACCGTTGTGCTGACCATCATTGATGA
GAATGACAATGTCCCTGTGGTTATAGGGCCTGCAATGCACAATAATACTGCAGAAATATCCATCCCCA
AAGGAGCTGAAAGTGGTTTTCATGTCACAAGAATAAGGGTGGTCGACAGGGACTCTGGTGCCAATGCT
GAATTCAGCTGCTCCATAGTATCTGGTAATGAGGAAAACATCTTTATCATGGACCCTAGGTCATGTGA
CATTCATACCAACGTCAGCATGGAATCCATTCCCTCTGCGGAATGGGCACTCTCAGTTATCATCCAGGA
CAAGGGCAGTCCTCCTCTGCACACCAAAGTCCTTCTGAGGTGCATGGTCTTTGACTATGCAGAATCTGT
GACAAGCACAGCCATGACCTCTGTCAGCCGCGCATCCTTGGATGTGTCCATGATCATAATTATTTCCTT
GGGAGCAATTTGTGCTGTGTTGCTGGTTATTATGGTCCTGTTTGCAACGAGGTGTAATAGAGAAAAGA
AAGACACCAGATCCTACAACTGCAGGGTGGCAGAATCCACGTACCAGCATCATCCTAAAAGGCCATCC
AGGCAGATTCACAAAGGAGACATCACACTGGTACCCACCATCAATGGCACTCTGCCCATCAGATCTCA
CCACAGATCCTCCCCATCTTCATCCCCAACCTTGGAGAGGGGACAAATGGGCAGCCGCCAGAGTCACA
ACAGTCACCAGTCACTCAACAGTTTGGTGACCATCTCATCAAACCACGTGCCAGAGAATTTTTCATTAG
AACTCACCCACGCCACTCCTGCTGTTGAGGTCTCGCAGCTTCTCTCCATGCTTCACCAGGGGCAATATC
AGCCACGGCCAAGTTTTCGAGGAAACAAATATTCCAGGAGCTATAGATATGCCCTTCAAGACATGGAT
AAATTTAGCCTGAAAGACAGTGGCCGTGGAGATAGCGAAGCAGGAGATAGCGATTATGATTTGGGGC

Figure 11A (cont)

GCGATTCTCCGATAGACAGGCTCCTGGGAGAAGGATTCAGTGACCTCTTCCTCACGGACGGGAGAATT
CCAGCAGCAATGAGGCTATGTACGGAGGAGTGCAGAGTCCTGGGCCACTCTGACCAGTGCTGGATGCC
CCCGCTGCCCTCGCCATCCTCTGACTACAGAAGCAACATGTTCATCCCCGGAGAAGAATTCCCAGCTC
AACCTCAGCAACAGCATTCTCATCAGGGCCTTGATGATGACAGCCAGCCTGCAGAAAACGGGGAGAA
AAAAAAGAGCTTCTCCACTTTTGGGAAGGACTCCCCTAGCGACGAGGATTCGGGAGACTCTAGCACAT
CATCTCTGCTATCAGAAATGAGCAGTGTGTTCCAGCGCCTTCTCCCCGCATCCCTAGATACCTTTTCTG
AATGCAACGAAGGGGATCGCTCCAACTCTCTGGAACGTCGAAAGGGTCCGGCACAGGGCAAAACTGG
GGGTTACCCACAAGGGGTTGCGGCCTGGGCAGCCAGCACACATTTTCAGAACCCCACCAGCAGCTCTG
GGACCCCTCTGGGGACTCACTCTAGTGTGCAGCCTTCCTCCAAGTGGCTGCCAGCTATGGAGGAGATT
CCTGAAAATTACGAGGAAGATGATTTTGACAATGTGCTTAACCATCTCAGCGATGGGAAACACGAACT
CATGGATGCCAGCGAGCTGGTGGCTGAGATCAACAAACTGCTTCAAGACGTCCGCCAGAGCTAG

Figure 11B

Protein ID:

NCBI: NP_569715.3

Translation (1134 aa):
MHQMNTKMHFRFALALLMAFFSHDVLAKNLKYRIYEEQRVGSVIARLSEDVADVLLKLPNPSAVRFRAM
PRGNSPLLVVNENTGEISIGAKIDREQLCQKNLNCSIEFDVLTLPTEHLQLFHIEVDVLDINDNSPQFSRP
VIPIEISESAAVGTRIPLDSAFDPDVGENSLHTYSLSANDYFNIEVRTRTDGAKYAELIVVKELDRELKA
SYELQLTASDMGVPQRSGSSILKISISDSNDNSPAFEQPSYTIQLLENSPVGTLLLDLNATDPDEGANGR
IVYSFSSHVSPKIIETFKIDSEKGHLTLFKPVDYEITKSYEIDVQAQDLGPNSIPAHCKIIIKVVDVNDN
KPEISINLMSPGKEEVSYVFEGDPIDTFVAIVRVQDKDSGLNGEIICKLHGHGHFKLQKTYENNYLILTN
ATLDREKRSEYSLTVIAEDKGTPSLSSVRHFTVQINDINDNPPRFQRSRYEFVISENNSPGAYITTVTAT
DPDLGENGHVTYTILESFVLGSSITTYVTIDPSNGAIYALRIFDHEEVSQITFVVEARDGGSQKQLSSNT
TVVLTIIDENDNVPVVIGPAMHNNTAEISIPKGAESGFHVTRIRVVDRDSGANAEFSCSIVSGNEENIFI
MDPRSCDIHTNVSMESIPSAEWALSVIIQDKGSPPLHTKVLLRCMVFDYAESVTSTAMTSVSRASLDVSM
IIISLGAICAVLLVIMVLFATRCNREKKDTRSYNCRVAESTYQHHPKRPSRQIHKGDITLVPTINGTLP
IRSHHRSSPSSSPTLERGQMGSRQSHNSHQSLNSLVTISSNHVPENFSLELTHATPAVEVSQLLSMLHQG
QYQPRPSFRGNKYSRSYRYALQDMDKFSLKDSGRGDSEAGDSDYDLGRDSPIDRLLGEGFSDLFLTDGRI
PAAMRLCTEECRVLGHSDQCWMPPLPSPSSDYRSNMFIPGEEFPAQPQQQHSHQGLDDDSQPAENGEKKK
SFSTFGKDSPSDEDSGDSSTSSLLSEMSSVFQRLLPASLDTFSECNEGDRSNSLERRKGPAQGKTGGYPQ
GVAAWAASTHFQNPTSSSGTPLGTHSSVQPSSKWLPAMEEIPENYEEDDFDNVLNHLSDGKHELMDASEL
VAEINKLLQDVRQS

METHODS AND AGENTS FOR MODULATING PROTOCADHERIN-18 ACTIVITY

CROSS REFERENCE TO RELATED APPLICATION

This application claims priority under 35 USC §119(e) from U.S. Provisional Application Ser. No. 61/708,901, filed Oct. 2, 2012, which application is herein specifically incorporated by reference in its entirety.

GOVERNMENTAL SUPPORT

The research leading to the present invention was supported, at least in part, by National Institutes of Health Grant Nos. R01 CA108573, F31 CA136164, and F31 CA162875. Accordingly, the Government has certain rights in the invention.

FIELD OF THE INVENTION

The present invention relates to methods for screening to identify modulator agents or compounds that affect protocadherin-18 (pcdh18) mediated inhibition of T cell receptor (TCR) signaling and effector phase function of CD8+ effector memory T cells. Also encompassed herein are methods for modulating pcdh18 mediated inhibition of TCR signaling. Pharmaceutical compositions comprising agents or compounds that modulate (inhibit or enhance) pcdh18 mediated inhibition of T cell receptor (TCR) signaling and effector phase function of CD8+ memory T cells are also encompassed herein. Adenocarcinoma is an exemplary tumor type for which such pharmaceutical compositions would confer benefit to patients. The invention further relates to agents or compounds that reduce or inhibit pcdh18 mediated inhibition of TCR signaling and effector phase function of CD8+ memory T cell activation and methods of using such agents or compound or pharmaceutical compositions thereof to achieve a more effective CD8+ T cell response to tumors.

BACKGROUND OF THE INVENTION

The citation of references herein shall not be construed as an admission that such is prior art to the present invention.

CD8+ CTL play an essential role in killing of virus-infected and transformed cells but in unmanipulated hosts fail to control tumor growth. Although the frequency of antigen-specific T cells in cancer patients is low, demonstrable priming occurs in response to tumor growth [1]. Investigation of animal models and tumor-bearing patients show production of antigen-specific CTL in the periphery but whose effector phase T cell function is suppressed upon entrance into the tumor [2,3], a phenotype postulated to contribute to tumor escape from immune-mediated eradication [4]. This implies the tumor microenvironment induces tumor infiltrating T cell (TIL) lytic dysfunction, a conclusion that has been substantiated by several experimental approaches [5]. In a murine model of colorectal carcinoma (MCA38) nonlytic TIL were shown to be recently-activated effector memory cells (CD44+ CD62L$^{lo}$CD69+CD95L+ CD122+CD127+ [6]). The dysfunctional lytic phenotype was subsequently shown to be due to a tumor-induced block in proximal TCR-mediated signaling that obviates ZAP70 activation, in turn due to rapid inactivation of p56$^{lck}$ upon contact with cognate tumor cells [7]. The nature of the tumor-induced block remained undefined in advance of the discoveries presented herein.

SUMMARY OF THE INVENTION

As indicated herein above, CD8+ tumor infiltrating T cells (TIL) lack effector-phase functions due to defective proximal TCR-mediated signaling previously shown to result from inactivation of p56$^{lck}$ kinase. During analysis of TIL p56$^{lck}$ we observed that when nonlytic TIL form conjugates ex vivo with cognate tumor cells, p56$^{lck}$ co-immuneprecipitates with a 120 kD protein, whose identity and potential role in regulation of TIL function was unknown. As described herein, we define the novel interacting partner for p56$^{lck}$ in nonlytic TIL as Protocadherin-18 ('pcdh18') and, moreover, show that pcdh18 is transcribed upon in vitro or in vivo activation of all CD8+ central memory T cells (Cm; CD44+ CD62L$^{hi}$CD127+) coincident with conversion into effector memory cells (Em; CD44+CD62L$^{lo}$CD127+). We also demonstrate that expression of pcdh18 in primary CD8+ effector cells induces the phenotype of nonlytic TIL: defective proximal TCR signaling, cytokine secretion, and cytolysis, and enhanced activation induced cell death (AICD). We also present evidence that pcdh18 contains a motif (centered at Y842) that is shared with src kinases (QGQYQP; SEQ ID NO: 19) and is required for the inhibitory phenotype. Thus, our results reveal that pcdh18 is a novel activation marker of CD8+ memory T cells that can function as an inhibitory signaling receptor and restrict the effector phase.

In accordance with results described herein, a method for screening to identify a modulator of protocadherin-18 (pcdh18) mediated inhibition of T cell receptor (TCR) signaling is presented, the method comprising: contacting a composition comprising a first and a second distinguishable pcdh18 population with a candidate modulator agent and assessing interaction levels of the first and second distinguishable pcdh18 populations in the presence of the candidate modulator agent, wherein detecting a change in interaction levels of the first and second distinguishable population of pcdh18 in the presence of the candidate modulator agent relative to interaction levels of the first and second distinguishable population of pcdh18 in the absence of the candidate agent or in the presence of a control agent identifies a modulator of pcdh18 mediated inhibition of T cell effector function. In a particular embodiment thereof, the pcdh18 mediated inhibition of TCR signaling relates to inhibition of proximal TCR signaling.

In an embodiment of the method, the change detected in the presence of the candidate modulator agent is a reduction in interaction levels of the first and second distinguishable populations of pcdh18, thereby identifying the candidate modulator agent as an inhibitor of pcdh18 mediated inhibition of T cell effector function. In a more particular embodiment, the first distinguishable population of pcdh18 is expressed on a cell. The cell may express pcdh18 endogenously and/or may be transfected to express exogenous pcdh18. In accordance with the method, cells expressing pcdh18 are contacted with pchdh18 protein. In a particular embodiment thereof, the second distinguishable population of pcdh18 comprises isolated proteins comprising pcdh18 protein.

In a further embodiment thereof, the cell expresses a T cell receptor. In a still further embodiment, the cell is a T cell.

In an aspect of the method, the change in interaction levels of the first and second distinguishable populations of pcdh18 is detected by measuring proximal T cell receptor signaling. In a particular embodiment thereof, the change detected in the presence of the candidate modulator agent is an increase in proximal T cell receptor signaling activity in the cell.

In a further aspect of the method, the change in interaction levels of the first and second distinguishable populations of pcdh18 is detected by measuring ZAP 70 activation, calcium flux and/or cytolytic activity. In a particular embodiment thereof, the change detected in the presence of the candidate modulator agent is an increase in ZAP 70 activation, calcium flux and/or cytolytic activity in the cell.

In yet another aspect of the method, the first and second distinguishable populations of pcdh18 each comprises isolated proteins comprising pchdh18 protein.

In a still further aspect, the method further comprises assaying in a cell based assay a modulator of pcdh18 mediated inhibition of T cell effector function initially identified in a non-cell based assay, wherein the cell based assay comprises at least one cell expressing pcdh18 and a T cell receptor to assess the ability of the modulator to alter pcdh18 mediated inhibition of T cell effector function in the at least one cell. The at least one cell expressing pcdh18 may express pcdh18 endogenously and/or may be transfected to express exogenous pcdh18. The at least one cell expressing a TCR may, moreover, express the TCR endogenously and/or may be transfected to express an exogenous TCR.

In an alternative embodiment, the first and second distinguishable populations of pcdh18 are expressed on two distinct populations of cells.

In a further aspect of the method, the candidate modulator agent is a small organic molecule, a protein or peptide, a nucleic acid, a carbohydrate, or an antibody.

Also encompassed herein is a method for stimulating or enhancing CD8+ T cell responses, the method comprising administering at least one candidate inhibitor of pcdh18 mediated inhibition of T cell effector function identified herein, or a nucleic acid sequence encoding same to a subject in need thereof. The method may further comprise assessing enhanced immune responses, wherein enhanced immune responses are detected as an increase TIL mediated effector immune response to tumors in the subject in need thereof. In an embodiment thereof, the subject in need thereof is a mammalian subject. In a particular embodiment thereof, the mammalian subject has a pcdh18 expressing tumor. In a more particular embodiment, the pcdh18 expressing tumor is an adenocarcinoma, breast cancer, ovarian cancer, cervical cancer, endometrial cancer, glioma, lymphoma, lung cancer, melanoma, pancreatic cancer, or liver cancer. More particularly still, the pcdh18 expressing tumor is an adenocarcinoma. In a particular aspect of the method, the mammalian subject is a human.

Also encompassed herein is a method for screening to identify agents that modulate pcdh18 mediated inhibition of T cell effector function, the method comprising: a) contacting a T cell expressing pcdh18 with a population of pcdh18 molecules in the presence or absence of a candidate modulator agent; and b) determining the ability of the candidate modulator agent to modulate proximal T cell receptor signaling, wherein a change in proximal T cell receptor signaling in the presence of the candidate modulator agent relative to that in the absence of the candidate modulator agent or in the presence of a control agent identifies the candidate modulator agent as a modulator of pcdh18 mediated inhibition of T cell effector function. In a particular embodiment, the change in proximal T cell receptor signaling is reflected in modulation of ZAP70 phosphorylation. In a more particular embodiment, the candidate modulator agent inhibits pcdh18 mediated inhibition of T cell effector function as reflected by increased ZAP70 phosphorylation. In another particular embodiment, the candidate modulator agent enhances pcdh18 mediated inhibition of T cell effector function as reflected by decreased ZAP70 phosphorylation.

In a further aspect thereof, the population of pcdh18 molecules is expressed on a cell. In a more particular embodiment, the cell is a tumor cell that expresses pcdh18. Tumor cells useful in such cell-based assays include adenocarcinoma cells, breast cancer cells, ovarian cancer cells, cervical cancer cells, endometrial cancer cells, glioma cells, lymphoma cells, lung cancer cells, melanoma cells, pancreatic cancer cells, and liver cancer cells.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 9A-B shows the nucleic (SEQ ID NO: 9) and amino (SEQ ID NO: 10) acid sequences of human pcdh18, respectively. As shown in (B), the extracellular domain is indicated in bold font, the transmembrane domain is indicated in bold font and underlined, and the cytoplasmic or intracellular domain is indicated in plain font. Within the cytoplasmic domain, the Y505 homology sequence also found in lck is underlined and the Y* represents the tyrosine residue that is phosphorylated in pcdh18 as described herein.

FIG. 10A-G shows nucleic and amino acid sequences corresponding to the extracellular domains (ED) of human pcdh18. Nucleic (SEQ ID NO: 11) and amino (SEQ ID NO: 12) acid sequences of ED1 are presented in (A) and (B), respectively. Nucleic (SEQ ID NO: 13) and amino (SEQ ID NO: 14) acid sequences of ED5 are presented in (C) and (D), respectively. (E) presents the nucleic acid sequence (SEQ ID NO: 15) encoding the start methionine to ED5 of human pcdh18. (F) presents the amino acid sequence (SEQ ID NO: 16) spanning ED1 to ED6, wherein each of ED1-ED6 is designated with the corresponding identifier in bold font below the amino acids (ED1, ED2, etc.) and the amino acids included therein indicated via underlining. (G) presents the nucleic acid sequence (SEQ ID NO: 54) encoding the start methionine to ED6 of human pcdh18.

FIGS. 11A-B shows the nucleic (SEQ ID NO: 17) and amino (SEQ ID NO: 18) acid sequences of mouse pcdh18, respectively.

DETAILED DESCRIPTION

As shown herein, the cell surface adhesion molecule pcdh18 is expressed widely in tissues, but in the hematopoietic system primarily in CD8+ effector memory T cells (CD8+ CD44+CD62L$^{lo}$CD127+) derived from recently-activated central memory cells (CD8+ CD44+ CD62L$^{hi}$CD127+). pcdh18 binds to $p56^{lck}$ in activated primary CD8+ effector memory cells and is closely associated with defective: cytokine secretion, cytolysis, and blockade of TCR signaling (including proximal TCR signaling), and enhanced AICD; a phenotype that mimics that of nonlytic TIL [5, 7]. These effects are characteristic of inhibitory signaling receptors (ISR) expressed in NK cells and T cells that function to dampen cellular immune responses [11, 15-17].

Figure 1:
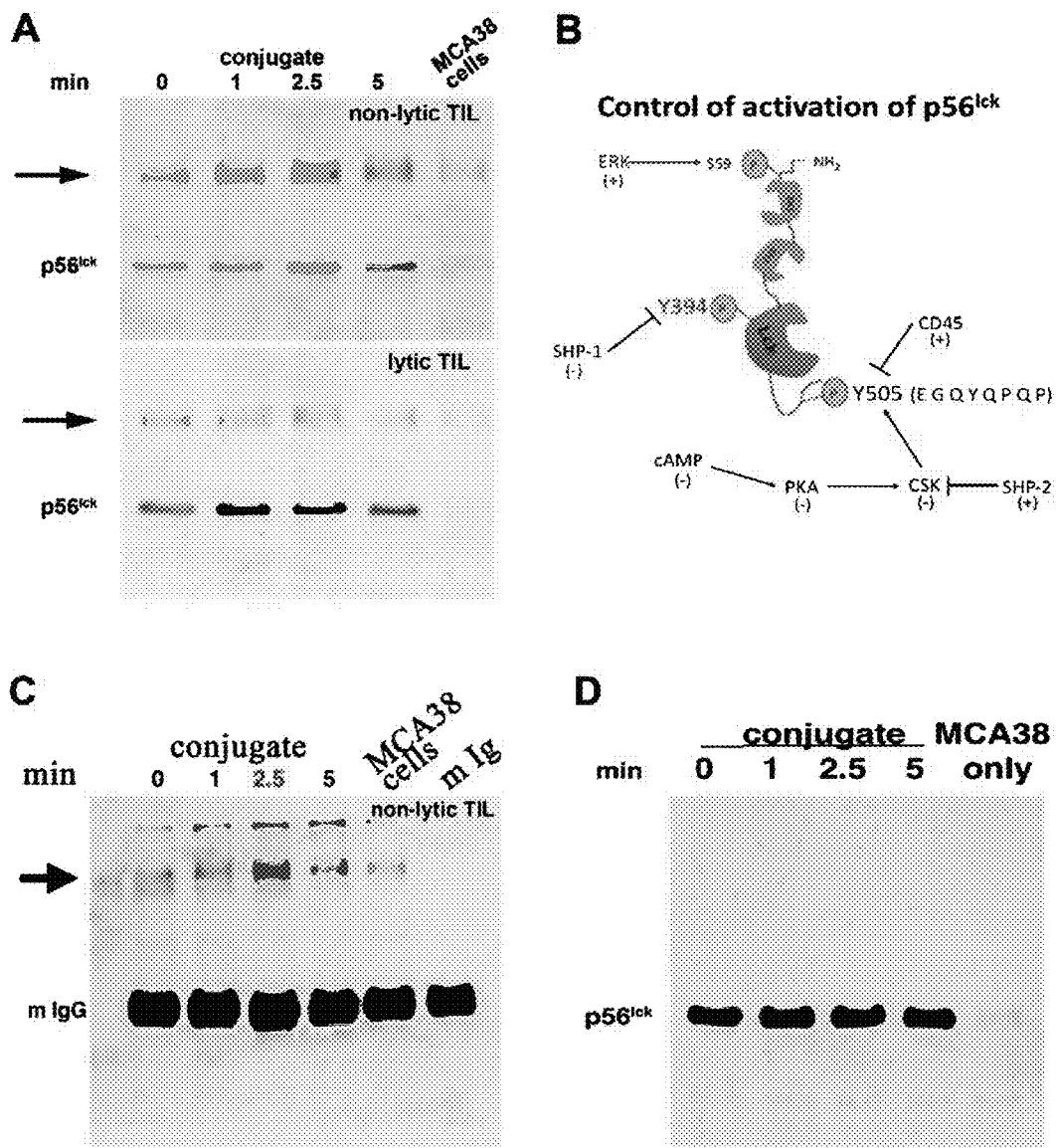
FIG. 1A-D shows a reciprocal immunoblot analysis of $p56^{lck}$ isolated from nonlytic and lytic MCA38 TIL. A) TIL were purified as described in [6] and either immediately used to form conjugates with MCA38 cells for the indicated times (upper panel) or plated in complete RPMI medium (lower panel) until performance of conjugation and reciprocal immunoblotting. Following incubation, detergent lysates were prepared and immunoprecipitated with Ab reactive with an epitope in the amino terminal portion of the protein (clone 3A5). Immunoprecipitated $p56^{lck}$ was subjected to immunoblotting using anti-$p56^{lck}$ (pY505) and detected by chemiluminescence following reaction with peroxidase-conjugated anti-rabbit. B) Schematic diagram of $p56^{lck}$. The two primary sites of $p56^{lck}$ regulation—the kinase activation motif (centered at Y394) and the inhibitory motif (centered at Y505) are indicated by boxes and key regulators of Y phosphorylation at each site are indicated. '+' and '−' indicate whether a given enzyme causes activation or inhibition of $p56^{lck}$ activity. Activation of kinase function is mediated by phosphorylation of Y394 which is autophosphorylated upon dephosphorylation of Y505 (by CD45). Once phosphorylated, control of kinase function is mediated by Shp-1 dephosphorylation of Y394. Phosphorylation of Y505 (by Csk) prevents autophosphorylation of Y394 and Csk activity is controlled by cAMP regulation of PKA activity. The amino acid sequence of the Y505 motif is also indicated. C) Reciprocal immunoblot analysis of $p56^{lck}$ using anti-pY Ab. TIL:MCA38 conjugates were formed for the indicated times as described above, extracts were prepared and immunoprecipitated with anti-$p56^{lck}$ (Ab 3A5), and blotted with anti-pY (4G10). The position of mouse IgG (the species used for $p56^{lck}$ immunoprecipitation, indicated as 'mIgG', and which obscures $p56^{lck}$) is validated by analysis of purified mouse IgG in the last gel lane and the arrowhead indicates the interacting protein detected by anti-pY blotting. D) High mw band is not $p56^{lck}$ dimer. Substitution of anti-pY505 with an anti-$p56^{lck}$ reactive to a different $p56^{lck}$ epitope than 3M (Ab 2102) was performed and detected only $p56^{lck}$ migrating at the appropriate mw, and not a higher molecular weight species, eliminating the possibility that the higher mw band represented dimeric $p56^{lck}$.
Figure 8:
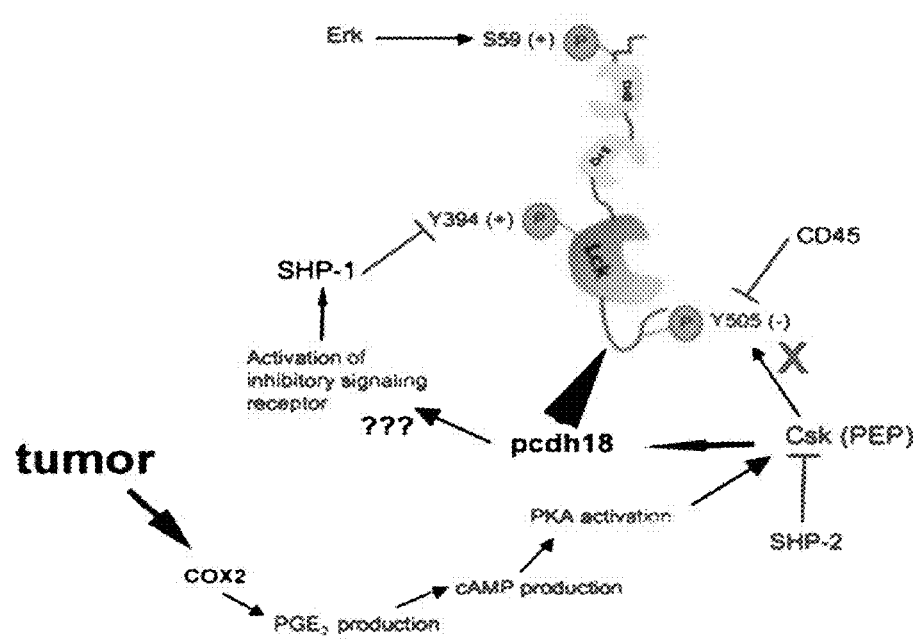
FIG. 8 shows a schematic of $p56^{lck}$ regulation involving pcdh18, related to FIG. 1. This updated model differs from that shown in FIG. 1B by incorporating results presented herein showing that $p56^{lck}$ Y505 is not phosphorylated upon activation of TIL and, likely also in memory CD8+ T cells since Zap70 is not activated in primary CD8+ T cells transfected to express pcdh18 [5]. In this model pcdh18 homophilic interactions between TIL and cognate MCA38 tumor disrupt TCR mediated signaling by binding to $p56^{lck}$. Binding of $p56^{lck}$ to pcdh18 causes a conformational change that prevents Csk (which localizes at the immune synapse with $p56^{lck}$ [7]) from phosphorylating the $p56^{lck}$ Y505 motif and thus permits phosphorylation of the homologous motif in pcdh18 (Y842). $p56^{lck}$-Y384 is then available for targeting by Shp-1 causing $p56^{lck}$ to deactivate as observed [5]. Thus, inactivation of $p56^{lck}$ results in the inability to activate ZAP70, in turn preventing propagation of proximal signaling and loss of effector phase lytic function.

Results presented herein also reveal that $p56^{lck}$ in CD8+ TIL interacts with pcdh18 coincident with robust phosphorylation at a tyrosine motif (Y842) shared with src kinases (QGQYQP; SEQ ID NO: 19). Y842 was shown by site-directed mutagenesis to be required for the pcdh18 inhibitory phenotype in transfected T cells. At early times during cell interaction the equivalent motif in $p56^{lck}$ (Y505) is not phosphorylated [5]. Since Csk is known to phosphorylate $p56^{lck}$ Y505, we hypothesize that it is responsible for the preferential phosphorylation of the homologous motif in pcdh18 (FIG. 8). Further to this point, it is reasonable to expect that pcdh18 can localize to TIL immunological synapses because pcdh18 and $p56^{lck}$ interact (FIG. 1) and Csk and $p56^{lck}$ are known to co-localize at the TIL immunological synapse [7]. The rapidity of inhibition of TCR signaling mediated by pcdh18 is characteristic of ISR expressed in immune cells. Thus, within seconds of recognition of cognate tumor cell, $p56^{lck}$ in anti-MCA38 TIL becomes inactive, therefore Zap70 is not activated and all downstream signaling is prevented which abrogates the effector phase. Although many studies have shown that a wide variety of inhibitory signaling receptors are expressed in cells of the adaptive immune response [16, 18], this is the first report of the adhesion molecule pcdh18 both being expressed in T cells and regulating proximal TCR signaling.

Figure 5:
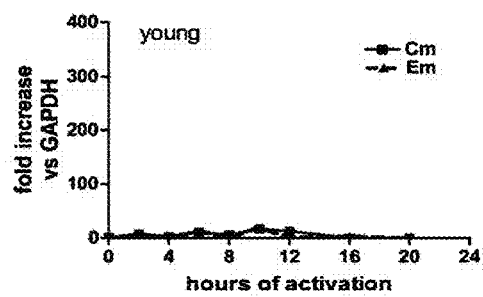
FIG. 5A-B shows protocadherin qRT-PCR and gene array analyses in activated Cm cells. A) pcdh18 qRT-PCR analysis of FACS-purified Cm and Em cells from young, aged, or 'memory' mice (from FIG. 4D) was as indicated (bottom panels). Gene array of FACS-purified Cm cells from a pool of 10 aged mice was performed by the NYU Center for Health Informatics and Bioinformatics. Purified Cm were activated in vitro and total cells in each culture were isolated for RNA extraction. cDNAs were hybridized to GeneChip arrays using an Affymetrix platform and the data were processed as described in Materials and Methods. B) Bone marrow CD8+ T cells were purified by positive selection magnetic immunobeading from young or aged mice, activated in vitro with ConA, and qRT-PCR performed as before.
Figure 5:
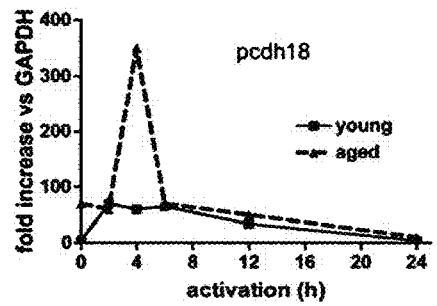
Figure 5:
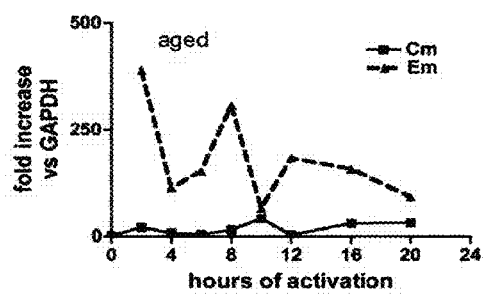
Figure 5:
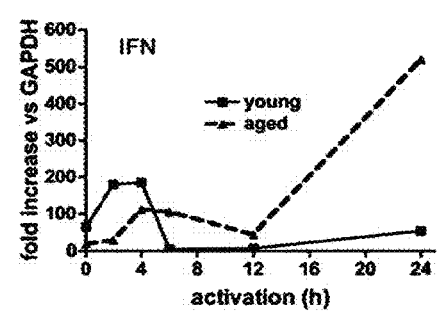
Figure 5:
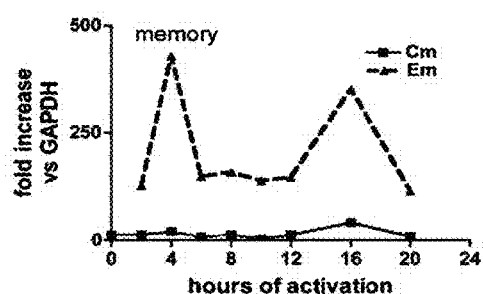
Figure 5:
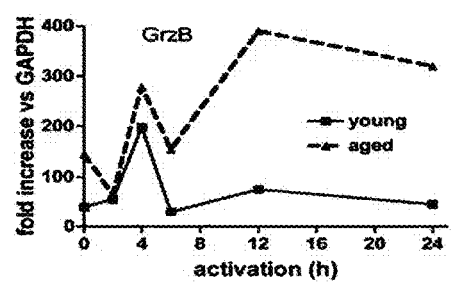
Figure 5:
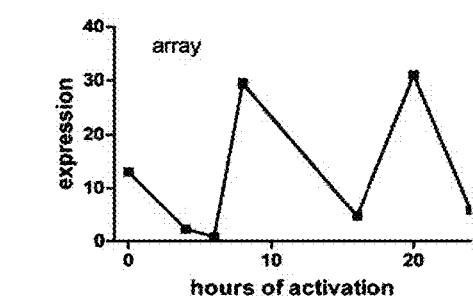

Since a role for pcdh18 in the immune system has not been previously reported, we determined its expression profile in CD8+ cells by RT-PCR in different states of differentiation and found that its expression is restricted to memory cells and is not unique to a particular experimental model, including endogenous cells from aged naive mice. The experiment in which Cm cells were purified and activated in vitro before purification of Em and Cm cells followed by RT-PCR analysis (FIG. 5) showed that neither Cm or Em originating from young mice robustly express pcdh18, in contrast to in vitro differentiated Em cells originating from aged mice. Perhaps there exists in young mice an endogenous CD44$^{hi}$CD62L$^{hi}$CD127+ Cm subpopulation that resists pcdh18 transcriptional activation under our ex vivo activation conditions. Alternatively, and more likely, memory cells identified by cell surface marker expression contain non-memory cells in addition to bona fide memory cells. We hypothesize that pcdh18 expression distinguishes the true memory population. In that experiment Cm cells from aged mice rapidly convert to Em cells (loss of CD62L) and the Em robustly express pcdh18 in an undulating kinetic pattern seen also by gene array analysis (FIG. 5a). The rapid kinetics of pcdh18 transcription induction in vitro or in vivo (FIG. 3c) further implies a role in memory re-activation.

That pcdh18 is a marker of Em formation is also supported by several observations including the robust expression in activated bone marrow-derived CD8+ T cells (FIG. 5b) and in isolated TIL. Further evidence that pcdh18 is a marker of authentic memory cells comes from the experiment in which TIL were adoptively transferred into RAG −/− mice. Adoptive transfer of naive cells into RAG −/− causes homeostatic expansion in which naive cells acquire a cell surface phenotype that resembles central memory cells (CD8+ CD44+CD62L$^{hi}$ CD127+), but these cells likely do not provide memory-mediated immune protection reflected by the lack of expression of IFN upon isolation. In contrast, IFN expression is extant, and further inducible, in cells derived from adoptive transfer of TIL, which do not express IFN in primary tumor tissue. pcdh18 transcription in adoptive transferred TIL and not in T cells derived from naive cells (90 days post transfer into RAG −/−) after in vitro activation confirms that pcdh18 expression is exclusive to CD8+ T cells that have been previously activated, i.e. bona fide memory cells.

To define the signature of CD8+ Cm T cells during differentiation into Em cells, we profiled the gene expression patterns of purified Cm cells during the early stage of in vitro activation by microarray. Activation of Cm cells resulted in differential expression of many genes whose expression clustered into five groups each having distinct kinetics. The clusters containing the largest numbers of active genes had their maximal expression at 8 and 20 hours of activation and cluster 4 (having the third largest number of genes, and which contains pcdh18), has maxima at both 8 and 20 hours of activation. The profiles of Cm cells at each time point of activation (2-24 h) were compared to non-activated cells and the normalized expression array data of all 5,274 "active genes" (see 'Materials and Methods') determined.

Figure 7:
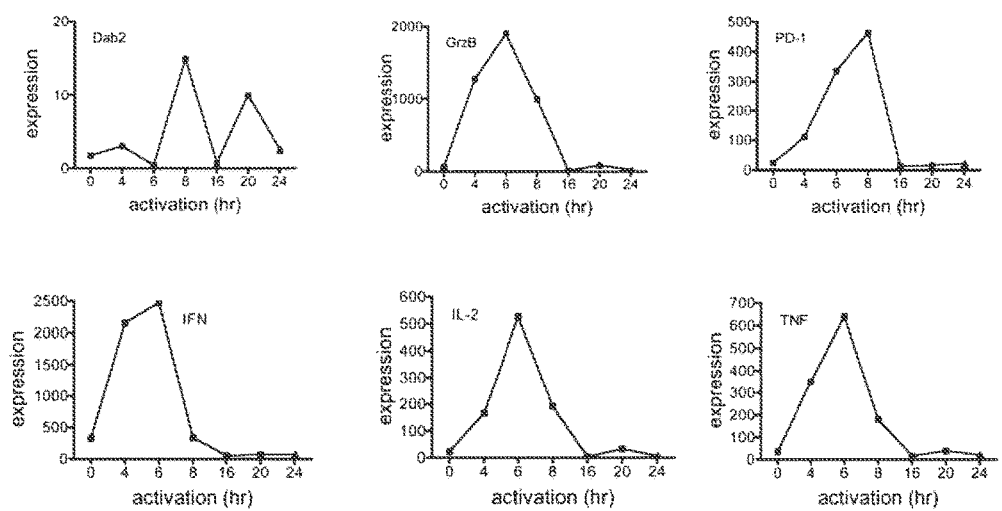
FIG. 7 shows gene array expression data for selected genes expressed in Cm cells upon activation. Relative expression at different times of activation of selected genes for which PCR validation is available is shown.

The undulating kinetics of pcdh18 expression (peaking twice within 24 h) is shared by 972 genes (by cluster analysis), which are nearly 20% of all active genes. This gene cluster (number 4) includes a candidate pcdh18-interacting partner Dab2 whose expression was also validated by RT-PCR. See also FIG. 7. pcdh18 belongs to the cadherin superfamily: a large family of transmembrane glycoproteins that mediate calcium-dependent, homophilic cell-cell adhesion. Interestingly, the analysis revealed the expression of more than 250 additional glycoproteins in the same cluster. Among these glycoproteins are CD55, Masp1, Nfam1, IL12A, P2RX7, P2X, Thbs1 and TLR4, genes that are implicated in activation of immune response. In addition, nearly 25% of the genes that belong to this cluster are classified as "membrane" genes and are also likely to participate in cell activation. Notably, 31 genes of this cluster are classified as "cell cycle" genes including: Cdca2, Bub1, Cdc25c, E2f2, Cyclin D1, Fgfr2, and Fgf10 (and another 12 genes are classified as "M phase" genes). The concomitant expression of both pcdh18, a mediator of TCR-signaling, and mitogenic genes that initiate cell cycle entry, suggests that pcdh18 may be influential in cell cycle entrance. Additional studies will reveal whether pcdh18 activation is cell cycle dependent. Furthermore, cell cycle entry of activated nonlytic TIL is typically followed by AICD [6]. Indeed, GO functional analysis of the early transcriptional response to Cm activation (cluster 2, genes that up-regulate 4 and 6 hours after activation) reveals strong enrichment of apoptotic genes in this cluster, among them the apoptotic facilitator BCL2-like 14, IFN, TNF and lymphotoxin A.

Figure 2:
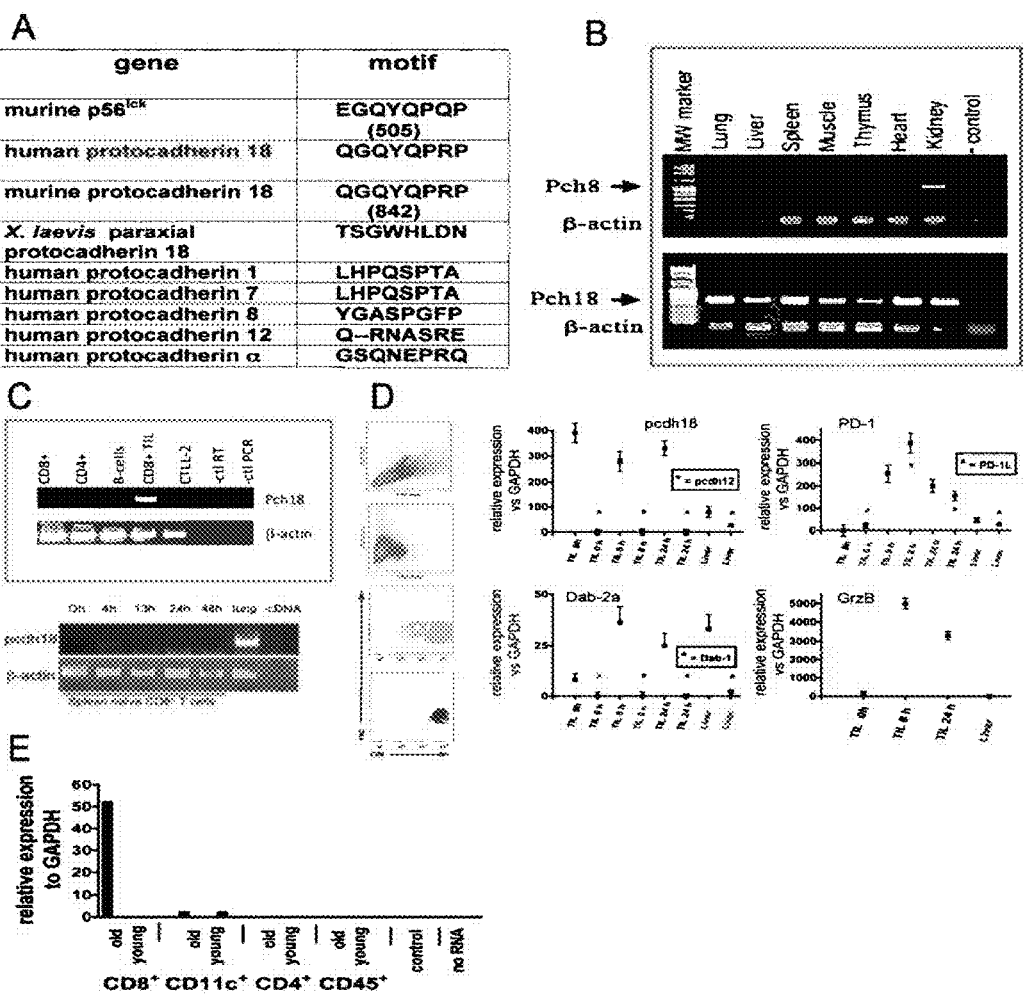
FIG. 2A-E shows RT-PCR analysis of protocadherin 18 in tissues and immune cells. A) Amino acid sequence comparison of the $p56^{lck}$ Y505 motif in protocadherins. The motifs listed therein are designated as follows: EGQYQPQP (SEQ ID NO: 1), QGQYQPRP (SEQ ID NO: 2), QGQYQPRP (SEQ ID NO: 3), TSGWHLDN (SEQ ID NO: 4), LHPQSPTA (SEQ ID NO: 5), YGASPGFP (SEQ ID NO: 6), QXRNASRE (SEQ ID NO: 7), and GSQNEPRQ (SEQ ID NO: 8). B) RT-PCR analysis of mouse tissues. The indicated tissues and organs were isolated from a control mouse, RNA was extracted and used to prepare cDNA, and PCR performed using control (pcdh8 and β-actin) or pch18 primers as described in 'Materials and Methods'. C) RT-PCR analysis of spleen cells. Spleens were isolated from a 7 week old mouse and the indicated cells were purified by FACS (top panel). TIL were isolated from an MCA38 tumor. CTLL-2 is a CD8+ lytic cell line. RNA was isolated and used to program RT-PCR as described in 'Materials and Methods'. Similarly spleen CD8+ T cells were purified and activated in vitro with anti-CD3 for the indicated times before analysis (bottom panel). D) TIL qRT-PCR analyses. Single cell suspensions of MCA38 tumors were prepared and CD4+ or CD8+ TIL were isolated by magnetic immunobeading. (Liver tissue was isolated and used for RNA isolation in certain control analyses. TIL were labeled with anti-CD4 or CD8 Ab and further purified by FACS (example of flow cytometry analysis shown in left panels) before RNA isolation and qRT-PCR analysis. TIL used to prepare RNA immediately after isolation are indicated in as 'nonlytic' or 'TIL 0 hr'. As indicated some TIL samples were cultured in vitro for 8 or 24 h before RNA isolation during which time TIL recover both proximal TCR-mediated signaling and lytic function [5, 7]. PCR analyses of various target RNAs are shown and include several control reactions that demonstrate specificity of the expression patterns observed (e.g. pcdh18 and pcdh12 in CD8+ TIL, Dab1 and Dab2a in CD8+ TIL, granzyme B in CD8+ TIL and liver, as well as TNF, IFN, IL-2, PD-1, and PD-1L). Data show SD from three independent experiments. E) qRT-PCR analysis of purified spleen cells. Spleen immune cells were isolated by FACS from young (4 week) or old (>48 week) control mice and RNA was isolated and used to program pcdh18 qRT-PCR as described in 'Materials and Methods'. The data shown are representative of multiple repetitions.

We also analyzed the array results for cluster distribution of ISR that have been shown to be expressed in T cells [16]. There are 8 'active' ISR genes (defined as having the highest coefficient of variation; >15% of total) and 17 'non-active' ISR genes expressed in activated Cm cells (this designation means that while expressed, the relative change in expression for this group is modest—having the lowest 85% of CV). Thus, 25 ISR genes are expressed during Cm cell conversion into Em cells which could potentially function to modulate proximal TCR signaling. This list includes several well-characterized ISR: PD-1, 2B4, CTLA-4, PEACAM (CD31), CEACAM-1 (CD66a), and CD85. RNA encoding a major ISR PD1 is expressed in freshly-isolated CD4+ TIL but not in CD8+ TIL (FIG. 2d). Upon activation of CD8+ TIL in vitro both PD-1 and its ligand PD-L1 are briskly unregulated with kinetics similar to GrzB. We interpret these data to mean that freshly-isolated TIL are nonlytic and express pcdh18 but not PD-1 RNA. In spite of upregulation of TIL PD-1 expression upon activation in vitro, if rested in vitro before activation, TIL regain lytic function diminishing a role for PD-1 in the nonlytic phenotype.

Gene array analysis showed that 'exhausted' CD8+ T cells that develop in response to persistent antigen load, are distinct from other T cells in different activation states, including anergic cells, and one gene prominently expressed in exhausted cells is PD-1 [19]. Since PD-1 RNA is not expressed in either nonlytic CD8+ TIL assayed in FIG. 2 and expression in Cm cells from aged mice is modest in comparison to Em cells, exhausted cells appear to be distinct from both Cm cells and nonlytic TIL. Interestingly, upon activation PD-1 is transcribed in both cell types and with similar kinetics as several genes characteristic of effector cells (e.g. GrzB, IL-2, TNF) [11, 12]. See also FIG. 7. A further distinction between nonlytic TIL and exhausted T cells is the rapidity with which TIL regain proximal TCR signaling and lytic function—within 2 h of purification [5]. However, exhausted T cells require dramatically longer to regain function (typically requiring PD-1 blockade [20]) and dysfunctional anergic T cells are thought to be very difficult to functionally recover.

As has been hypothesized previously, control of activation of the adaptive T cell immune response is tightly regulated by the activity of potentially a large number of ISR [16, 18]. Most ISR function as cell surface adaptor proteins that are themselves activated by an activating signal delivered to the cell (Ag recognition) and which function by recruiting an inhibitory phosphatase into proximity to its targets, often including the kinase responsible for activation of the ISR [17]. The rapidity and phenotype of inhibition of TCR signaling mediated by pcdh18 is characteristic of ISR expressed in immune cells which, although it differs from most ISR in lacking an ITIM motif and is activated by homophilic interaction in trans [21], functions equivalently in the inactivation of proximal TCR signaling by binding directly to $p56^{lck}$. Like other ISR (e.g. PD-1), pcdh18 is transcriptionally regulated upon activation of memory cells. Thus, in Cm cells where pcdh18 RNA is relatively low, functional inhibition of TCR signaling can occur after gene expression.

Expression of several dozen ISR genes during activation of Cm raises the question how Cm cells can be efficiently activated. The fact that Cm cells are rapidly activated and expand in vivo upon re-exposure to antigen supports the notion that: not all ISR transcripts are translated, that the encoded proteins are unable to function, or the inhibitory signal is superseded by the activation signal. It is also possible that ISR ligands are not expressed on APC during Cm re-activation, thus Ag-dependent activation is unimpeded. The notion that multiple ISR are expressed upon T cell activation but the availability of any given ligand controls ISR activity is supported by the observations that dendritic cells and endothelial cells can express ligands for multiple ISR [22, 23] and tumors commonly express ISR ligands (e.g. MCA38 tumors express pcdh18, B7-1 [24] and possibly additional ISR ligands). Such redundancy in this system that restricts effector T cell function argues its physiological importance in governing the response to re-activation of the memory response.

Collectively, our observations suggest that upon activation of CD8+ memory cells, pcdh18 interacts with $p56^{lck}$ and that the binding of $p56^{lck}$ by pcdh18 is causal to the failure to activate ZAP70 and subsequent deficient effector phase function. Thus, we have identified a novel p56$^{lck}$ binding protein that functions as an inhibitory signaling receptor during the effector phase in activated memory cells. In addition to the functional property of pcdh18 whereby it acts as an inhibitory signaling receptor that can arrest the effector phase, it is also the first described marker that uniquely identifies CD8$^+$ T cells of memory origin.

pcdh18 expressed in nonlytic TIL (or Em cells) is thought to engage in a homophilic interaction with pcdh18 expressed on a target cell, for example, a tumor, endothelial cell, or potentially an activated dendritic cell (DC). Extrapolating based on what is known with regard to other cadherins, pcdh18 is expected to display a 'polarity' due to the presence of a series of 'cadherin domains'. As characterized for other cadherins, these domains are also known to mediate interaction with ligands. pcdh18 has six cadherin-like domains. See, for example, FIG. 10, wherein the cadherin-like domains are referred to as ED1-ED6. As described herein, pcdh18 homodimerizes, thus one pcdh18 ligand is itself, but it is likely that other non-pcdh18 ligands exist. The individual cadherin domains of pcdh18 are, moreover, not identical in terms of amino acid sequence. When two cells that express pcdh18 interact, the pcdh18 molecules on each cell apparently lie side-by side. Thus, cadherin domain 1 (ED1 in FIGS. 10A and 10F) from one cell is thought to interact with domain 5 (ED5 in FIGS. 10D and 10F) from the other cell. Cadherin-like domains 2-4 likely also contribute to the homophilic interaction as well.

Although not wishing to be bound by theory, the present inventors propose that as a consequence of homophilic pcdh18 binding, recruitment of T cell pcdh18 into proximity with Csk permits phosphorylation at Y842. Y842 phosphorylation in turn either permits or enhances binding to p56$^{lck}$ leading to inactivation of kinase function or sequestration from its cognate targets TCRzeta or Zap70.

In accordance with the above, screening assays designed to identify modulators of pcdh18/pcdh18 interaction/binding and modulators of pcdh18/p56$^{lck}$ interaction/binding are envisioned herein. Such screening assays provide systems for identifying novel therapeutic agents and developing strategies to modulate immune responses qualitatively to induce a robust CD8+ memory T cell response to tumors in patients in need thereof. In one embodiment, a modulator of pcdh18/pcdh18 interaction/binding and/or pcdh18/p56$^{lck}$ interaction/binding is identified as an inhibitor because pcdh18/pcdh18 interaction/binding and/or pcdh18/p56$^{lck}$ interaction/binding is reduced or inhibited in its presence. Alternatively, a modulator of pcdh18/pcdh18 interaction/binding and/or pcdh18/p56$^{lck}$ interaction/binding is identified as an enhancer because pcdh18/pcdh18 interaction/binding and/or pcdh18/p56$^{lck}$ interaction/binding is increased or enhanced in its presence. Enhancers of pcdh18 interactions could, for example, stabilize pcdh18 homodimerization and thereby strengthen p56$^{lck}$ inhibition. Such enhancers would have application in treating autoimmune disease scenarios, such as Type I diabetes, wherein autoreactive CD8+ T cells cause pathology by inappropriately killing cells of the afflicted patient.

Screening assays as described herein may be performed using non-cell based assays and/or cell based assays. Such assays may be performed using full length pcdh18 protein or a fragment thereof. In a particular embodiment thereof, a screening assay is performed using an exemplary pcdh18 fragment such as the extracellular domain (ECD) of pcdh18, which is 697 amino acids long, which can be expressed and isolated (if necessary depending on the nature of the assay) using standard techniques known in the art. See, for example, FIGS. 9-11 and SEQ ID NOs: 9-18 and 54 therein. The ECD and fragments thereof are useful reagents for delineating the binding domain/s that are involved in pcdh18 homophilic binding. In this context, a functional fragment could be defined as an amino acid sequence that corresponds to a protein with a structure similar or identical to that of a cadherin-like binding motif of pcdh18. A cadherin binding motif is an amino acid sequence present in the extracellular portion of cadherin proteins that allows for interaction among the cadherins. The interaction between cadherin motifs requires Ca2+ ions. Usually three Ca2+ binding sites are present in any given Cadherin binding motif. Pcdh18 has six Cadherin-like motifs. It is believed that the homophilic interaction between the cadherin motif (CM) #1 of one Pcdh18 and the CM #5 of another Pcdh18 forms a stable conjugate. For the sake of clarity, CM1 is located at the N-terminus of the protein. Further to the above, exemplary pcdh18 fragments envisioned herein may consist of amino acid sequences of the cadherin-like binding motifs along with tags to allow for purification, identification of the protein and targeting.

In an alternate embodiment, an exemplary pcdh18 fragment is the pcdh18 cytoplasmic domain, which is 413 amino acids long and spans amino acid 721 to 1134 of full length pcdh18. Functional fragments thereof are also of utility and such fragments are envisioned to include the Y842 phosphorylation motif of pcdh18. In certain embodiments thereof, the tyrosine site of the fragment may be phosphorylated or mutated to an alternative amino acid. pcdh18 cytoplasmic domains and functional fragments thereof are used to investigate binding domains that are involved in pcdh18/p56$^{lck}$ interaction/binding and/or pcdh18/CSK interaction/binding. Also encompassed herein are pcdh18 cytoplasmic domains that comprise mutations in the DAB-1 binding region. Dab1 binding domains are the amino acids FQNP found at 1061-1064 of the amino acid sequence of pcdh18. Also envisioned herein are pcdh18 cytoplasmic domains that comprise mutations in some of the SH3 binding domains. SH3 domains consist of the amino acid sequence PXXP (wherein X can be any amino acid). There are three SH3-like sequences, which are located at the following amino acid positions 746-750, 933-936, 954-957 of pcdh18.

The ECD or a cytoplasmic domain of pcdh18 and functional fragments thereof may be labeled with a variety of protein tags, including detectable moieties that confer the ability to detect interaction/binding of labeled proteins to which they are attached and binding moieties, such as His Tags and GST tags that confer particular binding properties to proteins to which they are attached. Detectable labels include, for example, fluorescein, rhodamine, Texas Red, cyan fluorescent protein (CFP), yellow fluorescent protein (YFP), and green fluorescent protein (GFP) for visualization/detection. The ECD or a cytoplasmic domain of pcdh18 and functional fragments thereof may either be in solution or bound to a solid surface depending on the assay.

Non-Cell Based Assays

A variety of non-cell based assays have been described that may be utilized to identify modulators of pcdh18 mediated arrest of CD8$^+$ T cell effector phase, including affinity-based methods (e.g., affinity chromatography or panning), competitive inhibition assays (e.g., ELISAs), BIAcore assays, assays involving Covaspheres, and various visualization techniques, such as fluorescence resonance energy transfer (FRET). Each of these assays is well known in the art and may be performed in keeping with standard procedures.

In brief, BIAcore technology is based on surface plasmon resonance (SPR), an optical phenomenon that enables detection of unlabeled interactants in real time. SPR-based biosensors are used to determine the active concentration and assess molecular interactions, both with respect to affinity and chemical kinetics. A basic interaction experiment involves immobilizing one molecule of a binding pair on the sensor chip surface ("ligand") and injecting a series of concentrations of its partner ("analyte") across the surface. Changes in the index of refraction at the surface where the binding interaction occurs are detected by the hardware and recorded as RU (resonance units) in the control software. Curves are generated from the RU trace and are evaluated by fitting algorithms which compare the raw data to well-defined binding models. These fits are used to determine a variety of thermodynamic constants, including the apparent affinity of the binding interaction. Additional details pertaining to such BIAcore assays are known in the art and have been applied to a variety of cellular adhesion molecules. See, for example, Jin et al. (2008, Exp Biol Med 233:849-859); Chen et al. (2007, Proc Natl Acad Sci 104:13901-6); Sivakumar et al. (2007, J Biol Chem 282:7312-9); Catimel et al. (2005, J Proteome Res 4:1646-1656); and Syed et al. (2002, Biochem J 362:317-327), the entire content of each of which is incorporated herein by reference.

In one embodiment, direct interaction of the ECD or a cytoplasmic domain of pcdh18 and/or functional fragments thereof may be assessed in a BIAcore assay. In a particular embodiment thereof, the ECD of pcdh18 or functional fragment thereof, for example, is expressed as a GST fusion protein and immobilized on a BIAcore chip (the "ligand") and ECD or functional fragments thereof or synthetic peptides of motifs identified as binding motifs (the "analyte") are flowed over the chip to measure binding kinetics. Based on the kinetics, dissociation constants can be calculated. Although the above embodiment is set forth with respect to the ECD of pcdh18 or a functional fragment thereof, it is to be understood that the cytoplasmic domain of pcdh18 or functional fragment thereof could also be similarly tested in a BIAcore assay with an appropriate binding partner such as, for example, $p56^{lck}$. Accordingly, the embodiment involving the ECD of pcdh18 or a functional fragment thereof is set forth for illustrative purposes only.

Once the basic parameters of binding interactions are established for the BIAcore assay, potential modulators of pcdh18/pcdh18 interaction/binding can be added to the unbound molecules in advance of flow over the chip or during the flow over the chip step. In a particular embodiment thereof, if the presence of a modulator in the solution of molecules before or during the flow over the chip step reduces or inhibits binding of the analytes to the ligands, the modulator is identified as an inhibitor of the pcdh18/pcdh18 interaction/binding.

In another embodiment, a first population comprising pcdh18 ECDs or functional fragments thereof is covalently bound to a solid surface, such as a Red or Green MX Covasphere, and a second population comprising pcdh18 ECDs or functional fragments thereof is bound to a solid surface such as a Petri dish. Homophilic interaction of Covasphere-bound pcdh18 ECDs or functional fragments thereof and Petri dish-bound pcdh18 ECDs or functional fragments thereof can be detected by visualization of fluorescent Covaspheres bound to the Petri dish. Suitable controls would be performed to ensure that binding of Covaspheres is due to homophilic interaction of pcdh8 ECD or fragments thereof, as opposed to non-specific interactions. The activity of putative modulators of pcdh18 homophilic binding could be evaluated by performing the above assay in the presence or absence of putative modulators. A putative modulator would be identified as an inhibitor, for example, if pcdh18 homophilic binding (as measured by Covasphere binding to the Petri dish) is reduced in its presence. Similar methods have been used to delineate domains of various cell adhesion molecules, including L1 (Zhao et al. 1995, J Biol Chem 270:29413-29421; the entire content of which is incorporated herein by reference). As indicated herein above, the embodiment involving the ECD of pcdh18 or a functional fragment thereof is set forth for illustrative purposes only and other regions, domains, or fragments of pcdh18 can be assessed using Covasphere technology.

In yet another embodiment, protein interactions and modulation thereof can be examined using FRET. In brief, FRET is based on energy transfer between two chromophores. A donor chromophore, initially in its electronic excited state, may transfer energy to an acceptor chromophore through nonradiative dipole-dipole coupling. The efficiency of this energy transfer is inversely proportional to the sixth power of the distance between donor and acceptor, thus making FRET extremely sensitive to small distances. Accordingly, FRET can be used to measure the distance between two fluorophores. When adapted to analyses of protein-protein interactions, FRET can be used advantageously to determine if two proteins that are differentially labeled (i.e., wherein each is labeled with a different fluorophore) bind to each other since the FRET readout will differ depending on whether the differentially labeled proteins are bound to each other or not. Exemplary pairs of fluorophores for use in FRET based analyses of protein-protein interactions comprise cyan fluorescent protein (CFP) and yellow fluorescent protein (YFP). Both of which are color variants of green fluorescent protein (GFP). Labeling with organic fluorescent dyes requires purification, chemical modification, and intracellular injection of a host protein. Alternatively, GFP variants can be attached to a host protein by genetic engineering. Bioluminescence Resonance Energy Transfer (BRET) provides an alternative system wherein a bioluminescent luciferase (typically that of *Renilla reniformis*), rather than CFP is used to produce an initial photon emission compatible with YFP.

Accordingly, in an application of FRET, a first population comprising pcdh18 ECDs or functional fragments thereof, for example, is labeled with CFP and a second population comprising pcdh18 ECDs or functional fragments thereof is labeled with YFP and the two populations are brought into contact. Detection of binding/interaction between the differentially labeled first and second populations can be achieved by measuring fluorescence emissions that change based on proximity of the different labels. As described herein above with respect to other screening assays, the activity of putative modulators of pcdh18 homophilic binding could be evaluated by performing the above assay in the presence or absence of putative modulators. A putative modulator would be identified as an inhibitor, for example, if pcdh18 homophilic binding (as measured by a change in fluorescence emissions) was reduced in its presence. The above embodiment involving the ECD of pcdh18 or a functional fragment thereof is set forth for illustrative purposes only and is not intended to preclude analysis of other pcdh18 regions, domains, or fragments.

Cell Based Assays

Cell based assays are presented herein as an alternative primary screening assay or as a secondary screening assay to validate the activity of modulators identified in non-cell based assays. Any cell that expresses endogenous pcdh18 and $p56^{lck}$ or can be transfected to express exogenous pcdh18 and $p56^{lck}$ can be used in cell based assays. Suitable cell lines include Cos cells, baby hamster kidney (BHK) cells, Jurkat cells, and Chinese hamster ovary (CHO) cells. An exemplary cell based assay involves CD8+ cells that express endogenous pcdh18 (e.g., Em cells) or pcdh18-transfected CD8+ T cells. Naive T cells that are negative for pcdh18 provide a useful platform for cell based assays because they most closely resemble effector T cells. Such cells may originate from any mammal. Exemplary mammals include mice, rats, monkeys, and humans.

As described herein for the first time, pcdh18 has been identified as an inhibitory signaling receptor during the effector phase in activated memory cells. More particularly, results presented herein demonstrate that upon activation of $CD8^+$ memory cells, pcdh18 interacts with $p56^{lck}$ and binding of $p56^{lck}$ by pcdh18 results in failure to activate ZAP70 and subsequent deficient effector phase function. In light of the results presented herein, the present inventors have identified the first marker that uniquely identifies $CD8^+$ T cells of memory origin and, moreover, characterized it functionally as a novel $p56^{lck}$ binding protein that can arrest the effector phase in activated CD8+ memory.

Further to the discovery that pcdh18 binds to $p56^{lck}$, which in turn leads to failure to activate ZAP70 and inhibition of the effector phase in activated CD8+ memory cells, the present inventors have developed cell based screening assays to identify agents/molecules capable of modulating pcdh18/pcdh18 interaction/binding and/or capable of modulating pcdh18/p56" interaction/binding. Such screening assays provide systems for identifying novel therapeutic agents and developing strategies to modulate immune responses qualitatively to induce a robust CD8+ memory T cell response to tumors in patients in need thereof.

In a particular embodiment, cell based screening assays directed to identifying agents/molecules capable of blocking pcdh18/pcdh18 homophilic binding (i.e., inhibitors thereof), which leads to failure to activate ZAP70 and inhibition of the effector phase in activated CD8+ memory cells (see, e.g., FIG. 6) are described. Such screening assays may, for example, be cell based assays that utilize cells that express endogenous pcdh18 or are transfected to express exogenous pcdh18 or a functional fragment thereof. As described herein above with respect to non-cell based assays, pcdh18 fragments useful for investigating pcdh18/pcdh18 homophilic binding and the identification of modulators thereof (e.g., inhibitors) include the ECD of pcdh18 and functional fragments thereof that are capable of conferring pcdh18/pcdh18 homophilic binding. Such polypeptides may be expressed with or without tags, such as for example a Histidine (His) tag or the like.

In a particular embodiment of a cell-based assay, a CD8+ T cell is transfected with a construct that encodes pcdh18 such as that described in the Examples set forth herein (see also FIG. 6 and description thereof) so as to generate a CD8+ T cell that expresses transfected pcdh18 on its cell surface (CD8+/pcdh18+ T cells). CD8+/pcdh18+ T cells can then be brought into contact with cell types that express pcdh18 on their cell surface (e.g., a tumor cell, endothelial cell, or an activated dendritic cell) and incubated in the presence or absence of a potential candidate agent or plurality of candidate agents to determine if the presence of the candidate agent/s modulates pcdh18 mediated inhibition, for example, of the effector phase in activated CD8+ memory cells and resultant induction of nonlytic TIL characterized by defective proximal TCR signaling, cytokine secretion, and cytolysis, and enhanced AICD. Accordingly, a candidate agent or agents that partially or completely restore proximal TCR signaling as reflected by, for example, activation of ZAP70, calcium flux and cytolytic activity is identified as an inhibitor. Assays envisioned herein for assessing proximal TCR signaling also include, without limitation, increased total phospho-tyrosinylated proteins. Tyrosine phosphorylation of other proteins that participate in TCR signal transduction include LAT, ERK, PLCγ-1. Tyrosine phosphorylation of these indicator proteins of proximal TCR signaling can be detected by flow cytometry or immunoblotting using commercially available antibodies. See also "Cellular and Molecular Immunology" $7^{th}$ ed. Abbas et al. 2011.

An exemplary cell line for the aforementioned embodiment is the CTLL-2 cell line, which is a mouse CD8+ T cell that does not express pcdh18. CTLL-2 exhibits lytic function, so it shares in common many of the functions that the TIL described herein possess. "Activated primary effector" T cells (negative for pchd18 but which have lytic functions) used in some experiments described herein share the expression of certain cell surface markers with authentic memory cells taken straight from the body, including $CD8^{hi}CD44^{hi}CD62L^{hi}$.

Alternatively, the above described CD8+/pcdh18+ T cells can be contacted with the ECD of pcdh18 or a fragment thereof that confers homophilic pcdh18 binding (which may be expressed with or without a tag, such as, e.g., a His tag) and in like fashion to the above, a candidate agent or a plurality of same can be evaluated to determine if the agent/s partially or completely restore proximal TCR signaling.

In an alternative embodiment, a CD8+ T cell that expresses endogenous pcdh18 can be used in the above outlined screening assays to assess the potential of candidate agents to restore TCR signalling partially or completely. As outlined above, such assays may be performed with cell types that express pcdh18 on their cell surface or pcdh18 ECD polypeptides or fragments thereof.

Additional cell based assay readouts include an assessment of cellular clustering. This assessment is based on the finding that one of the functions of pcdh18 in primary CD8+ T cells is to affect clustering. When activated in vitro by cross-linking of the TCR, primary CD8+ T cells expand and under the microscope appear as "clusters". If the cells are transfected to express pcdh18 before activation they do not form clusters, but instead die via apoptosis. Accordingly, modulators of the pcdh18 mediated inhibition of clustering can be identified using clustering and/or cell viability as a readout/indicator.

Agents identified using the screening assays described herein can be used in therapeutic applications directed to promoting CD8+ T cell response to tumors and, more particularly, to promoting CD8+ effector function in the tumor environment to confer a more effective immune response against pcdh18 expressing tumors in patients in need thereof.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed.

(1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. TERMINOLOGY

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned in part with antigen-antibody type reactions and homophilic and heterophilic ligand interactions.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" is any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J. Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An antibody or antigen-binding portion thereof may, furthermore, be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93 101) and use of a cysteine residue, a marker peptide and a C-terminal polyhistidine tag to make bivalent and biotinylated scFv molecules (Kipriyanov, S. M., et al. (1994) Mol. Immunol. 31:1047 1058). Antibody portions, such as Fab and F(ab)$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Further to the above, antibodies may be xenogeneic, allogeneic, or syngeneic; or modified forms thereof, e.g. humanized, chimeric, etc. Preferably, antibodies of the invention bind specifically or substantially specifically to pcdh18 molecules. The term "humanized antibody", as used herein, is intended to include antibodies made by a non-human cell having variable and constant regions which have been altered to more closely resemble antibodies made by a human cell. This may be achieved by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-cancer or anti-tumor specific antibody. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF) or a toxin (e.g., ricin) or anti-mitotic or apoptotic agent or factor.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "adjuvant" refers to a compound or mixture that enhances the immune response, particularly to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

As used herein, the term "immunomodulator" refers to an agent which is able to modulate an immune response. An example of such modulation is an enhancement of cell activation or of antibody production.

The term "effective amount" of an immunomodulator refers to an amount of an immunomodulator sufficient to enhance a vaccine-induced immune response, be it cell-mediated, humoral or antibody-mediated. An effective amount of an immunomodulator, if injected, can be in the range of about 0.1-1,000 μg, preferably 1-900 μg, more preferably 5-500 μg, for a human subject, or in the range of about 0.01-10.0 μg/Kg body weight of the subject animal. This amount may vary to some degree depending on the mode of administration, but will be in the same general range. If more than one immunomodulator is used, each one may be present in these amounts or the total amount may fall within this range. An effective amount of an antigen may be an amount capable of eliciting a demonstrable immune response in the absence of an immunomodulator. For many antigens, this is in the range of about 5-100 μg for a human subject. The appropriate amount of antigen to be used is dependent on the specific antigen and is well known in the art.

The exact effective amount necessary will vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the vaccine art.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The term "comprise" is generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtiter plates for use in immunoassays, or will be mixed with pharmaceutically acceptable carriers or diluents when used in diagnosis or therapy.

As used herein, "pg" means picogram, "ng" means nanogram, "ug" or "μg" mean microgram, "mg" means milligram, "ul" or "μl" mean microliter, "ml" means milliliter, "l" means liter.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |

-continued

| TABLE OF CORRESPONDENCE | | |
|---|---|---|
| SYMBOL 1-Letter | 3-Letter | AMINO ACID |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding pcdh18 or peptide sequences therein or comprising or consisting of sequences which are degenerate thereto. DNA sequences having the nucleic acid sequence encoding the peptides of the invention are contemplated, including degenerate sequences thereof encoding the same, or a conserved or substantially similar, amino acid sequence. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |

```
                       -continued
Threonine (Thr or T)    ACU or ACC or ACA or ACG Alanine (Ala or A)      GCU or GCC or GCA or GCG Tyrosine (Tyr or Y)     UAU or UAC Histidine (His or H)    CAU or CAC Glutamine (Gln or Q)    CAA or CAG Asparagine (Asn or N)   AAU or AAC Lysine (Lys or K)       AAA or AAG Aspartic Acid (Asp or D) GAU or GAC Glutamic Acid (Glu or E) GAA or GAG Cysteine (Cys or C)     UGU or UGC Arginine (Arg or R)     CGU or CGC or CGA or CGG or AGA or AGG Glycine (Gly or G)      GGU or GGC or GGA or GGG Tryptophan (Trp or W)   UGG Termination codon       UAA (ochre) or UAG (amber) or UGA (opal)
```

It should be understood that the codons specified above are for RNA sequences. The corresponding codons for DNA have a T substituted for U.

Mutations can be made in the sequences encoding the protein or peptide sequences of the pcdh18 proteins, peptides or immune activator proteins or peptides of the invention, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at Ph 6.0)
Aspartic acid, Glutamic acid
Basic Amino Acids (Positively Charged at pH 6.0)
Lysine, Arginine, Histidine (at pH 6.0)
Another Grouping May be Those Amino Acids with Phenyl Groups:
Phenylalanine, Tryptophan, Tyrosine Another grouping may be according to molecular weight (i.e., size of R groups):

| Glycine | 75 | Alanine | 89 |
|---|---|---|---|
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues, preferably at least about 80%, and most preferably at least about 90, 91, 92, 93, 94, 95, 96, 97, 98, or 99% of the amino acid residues are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The term 'agent' means any molecule, including pcdh18-derived peptides or other polypeptides, antibodies, polynucleotides, chemical compounds and small molecules. In particular the term agent includes compounds such as test compounds or drug candidate compounds. The term 'modulator agent" as used herein refers to an agent whose presence alters an interaction (e.g., a biochemical or physical interaction) relative to a control or inert agent. A modulator agent may, therefore, increase/enhance or decrease/reduce such an interaction relative to a control or inert agent. In a particular aspect, a modulator agent identified in a screening assay described herein inhibits pcdh18/pcdh18 homophilic interactions and is, therefore, identified as an inhibitor of pcdh18 mediated inhibition of CD8+ T cell effector function.

The term 'agonist' refers to a ligand that stimulates the receptor to which the ligand binds in the broadest sense or stimulates a response that would be elicited on binding of a natural ligand to a binding site.

The term 'assay' means any process used to measure a specific property of a compound or agent. A 'screening assay' means a process used to characterize or select compounds based upon their activity from a collection of compounds.

"Preventing" or "prevention" refers to a reduction in risk of acquiring a disease or disorder.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

The term 'treating' or 'treatment' of any disease or infection refers, in one embodiment, to ameliorating the disease or infection (i.e., arresting the disease or growth of a causative infectious agent or bacteria, or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, the term "autologous" refers to organs, tissues, cells, or proteins isolated from a donor patient that are later re-introduced into the donor patient. Accordingly, the donor and recipient are the same patient in autologous transfers. The term "autologous T cells", for example, refers to T cells that have been isolated from a subject and then administered to the same patient. Typically, and in accordance with the present methods, the isolated T cells may be stimulated in cell culture prior to administration to the patient.

B. FURTHER ASPECTS OF THE DETAILED DESCRIPTION

The invention relates generally to methods and agents for inducing immune responses to tumors, particularly those that express pcdh18. Prior to the discoveries detailed herein, there was no appreciation that pcdh18 on CD8+ T cells and homophilic engagement thereof by pcdh18 on a tumor cell leads to inhibition of CD8+ T cell effector function against the tumor. This insight into the mechanism/s whereby tumors expressing pcdh18 subvert the immune response to be a less effective weapon against tumor cell clearance has been used to advantage to design new screening assays and methods for using same to identify agents that modulate pcdh18/pcdh18 interaction. Agents identified thereby and therapeutic regimens utilizing these agents are also encompassed. Also subsumed herein are pcdh18 fragments that may be used to advantage for therapeutic purposes.

Accordingly, methods and agents for inducing an effective immune response to tumors that express pcdh18, including colorectal cancer, breast cancer, ovarian cancer, cervical cancer, endometrial cancer, glioma, lymphoma, lung cancer, melanoma, pancreatic cancer, and liver cancer are presented herein. See also worldwide website for the Human Protein Atlas relating to pcdh18 and its expression pattern in various cancers, the entire content of which is incorporated herein in its entirety. In one aspect, a method directed to promoting CD8+ T cell responses against tumors and, more particularly, to promoting CD8+ T cell responses to pcdh18 expressing tumors so as to induce a more effective immune response against these tumors is presented.

The present invention provides assays for screening and identifying agents, compounds or peptides to modulate immune response to a pcdh18 expressing tumor, indicators to evaluate the effectiveness of an immune response to a pcdh18 expressing tumor, and methods for stimulating or facilitating immune response to a pcdh18 expressing tumor. The methods, assays, and indicators described herein are based, in part, on the ability of pcdh18/pcdh18 interaction/binding to inhibit CD8+ T cell effector function by inhibiting proximal TCR signaling. The methods, agents and assays of the invention can be implemented in therapeutic strategies (e.g., vaccine strategies) directed to the stimulation of a CD+ T cell-based immune response to, for example, pcdh18 expressing tumors.

Thus, in an embodiment, method is directed to inducing an effective immune response to pcdh18 expressing tumors, including colorectal cancer, breast cancer, ovarian cancer, cervical cancer, endometrial cancer, glioma, lymphoma, lung cancer, melanoma, pancreatic cancer, and liver cancer are presented herein. See also worldwide website for the Human Protein Atlas relating to pcdh18 and its expression pattern in various cancers, the entire content of which is incorporated herein in its entirety. As described above, triggering an effective CD8+ T cell-based immune response to pcdh18 expressing tumors comprises one aspect of an effective immune response.

The present invention also includes pcdh18 domains (such as, e.g., the ECD or cytoplasmic domain) or a fragment thereof, which are covalently attached to or otherwise associated with other molecules or agents. These other molecules or agents include, but are not limited to, molecules (including antibodies or antibody fragments) with distinct recognition, targeting or binding characteristics, immune cell modulators, immune cell antigens, toxins, ligands, adjuvants, and chemotherapeutic agents.

Peptides and proteins of the invention may be labelled with a detectable or functional label. Detectable labels include, but are not limited to, radiolabels such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{117}$Lu, $^{211}$At, $^{198}$Au, $^{67}$Cu, $^{225}$Ac, $^{213}$Bi, $^{99}$Tc and $^{186}$Re, which may be attached to antibodies of the invention using conventional chemistry known in the art of antibody imaging. Labels also include fluorescent labels (for example fluorescein, rhodamine, Texas Red) and labels used conventionally in the art for MRI-CT imaging. They also include enzyme labels such as horseradish peroxidase, β-glucoronidase, β-galactosidase, and urease. Labels further include chemical moieties such as biotin which may be detected via binding to a specific cognate detectable moiety, e.g. labelled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

Peptides of and of use in the present invention may include synthetic, recombinant or peptidomimetic entitites. The peptides may be monomers, polymers, multimers, dendrimers, concatamers of various forms known or contemplated in the art, and may be so modified or mutlimerized so as to improve activity, specificity or stability. For instance, and not by way of limitation, several strategies have been pursued in efforts to increase the effectiveness of antimicrobial peptides including dendrimers and altered amino acids (Tam et al (2002) Eur J Biochem 269 (3): 923-932; Janiszewska et al (2003) Bioorg Med Chem Lett 13 (21):3711-3713; Ghadiri et al. (2004) Nature 369(6478):301-304; DeGrado et al (2003) Protein Science 12(4):647-665; Tew et al. (2002) PNAS 99(8):5110-5114; Janiszewska et al (2003) Bioorg Med Chem Lett 13 (21): 3711-3713). U.S. Pat. No. 5,229,490 discloses a particular polymeric construction formed by the binding of multiple antigens to a dendritic core or backbone.

Protamines or polycationic amino acid peptides containing combinations of one or more recurring units of cationic amino acids, such as arginine (R), tryptophan (W), lysine (K), even synthetic polyarginine, polytryptophan, polylysine, have been shown to be capable of killing microbial cells. These peptides cross the plasma membrane to facilitate uptake of various biopolymers or small molecules (Mitchell D J et al (2002) J Peptide Res 56(5):318-325).

Conjugates or fusion proteins of the present invention, wherein pcdh18 or domains or fragments thereof or modulatory agents identified using screening methods as described herein are conjugated or attached to other molecules or agents further include, but are not limited to, binding members conjugated to a cell targeting agent or sequence, chemical ablation agent, toxin, immunomodulator, cytokine, cytotoxic agent, chemotherapeutic agent or drug.

Uptake and targeting of DCs, for example, can be achieved using a variety techniques known in the art, including coupling to antibodies targeting DC-specific surface molecules (Romani et al., 2010; the entire contents of which is incorporated herein in its entirety, including references cited therein); utilization of engineered Sindbis envelope that specifically target DC instead of VSV-G (Yang et al., 2008; the entire content of which is incorporated herein in its entirety); site of administration; blood infusion; or ex vivo culture of DC, treatment of ex vivo cultured DC to introduce the desired construct/s, and re-injection of same into subject in need thereof.

In vitro assays are described herein which may be utilized by the skilled artisan to further or additionally screen, assess, and/or verify the activities of pcdh18 or domains or fragments thereof or modulatory agents identified using screening methods as described herein, including further assessing TIL activity. Cell based assays and in vitro methods are described herein and were utilized to perform experiments as described, for example, in the Examples.

In vivo animal models of human pcdh18 expressing tumors and adenocarcinoma or immune response to same may be utilized by the skilled artisan to further or additionally screen, assess, and/or verify the activity of pcdh18 or domains or fragments thereof or modulatory agents identified using screening methods as described herein, including further assessing immune responses targeted against pcdh18 expressing tumor cells in vivo. Such animal models include, but are not limited to models of immune system modulation or immune response.

Proteins, peptides, immune activators or agents of the present invention may be administered to a patient in need of treatment via any suitable route, including by intravenous, intraperitoneal, intramuscular injection, or orally. The precise dose will depend upon a number of factors, including whether the proteins, peptides, immune activators or agents are for diagnosis or for treatment or for prevention. The dosage or dosing regime of an adult patient may be proportionally adjusted for children and infants, and also adjusted for other administration or other formats, in proportion for example to molecular weight or immune response. Administration or treatments may be repeated at appropriate intervals, at the discretion of the physician.

Proteins, peptides, immune activators or agents described herein are generally administered in the form of a pharmaceutical composition, which may comprise at least one component in addition to the proteins, peptides, immune activators or agents. Pharmaceutical compositions according to the present invention, and for use in accordance with the present invention, may comprise, in addition to active ingredient, a pharmaceutically acceptable excipient, carrier, buffer, stabiliser or other materials known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

The mode of administration of a pharmaceutical composition comprising a modulatory agent/s identified using screening methods described herein or an immunogenic composition of the invention, whether of the pcdh18 or domains or fragments thereof alone or as part of an immunogenic conjugate, may be by any suitable route which delivers a therapeutically effective amount or an immuno-protective amount of the protein or agent to the subject. One such route is the parenteral route, such as by intramuscular or subcutaneous administration. Other modes of administration may also be employed, where desired, such as the mucosal route, such as by oral, rectal, buccal or intranasal administration, or via other parenteral routes, i.e., intradermally, intravenously, intraperitoneally, or intratumorally.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the proteins, peptides, immune activators or agents herein described and other agents or therapeutics such as immune modulators, antibodies, immune cell stimulators, or adjuvants. In addition, the composition may be administered with hormones, such as dexamethasone, immune modulators, such as interleukins, tumor necrosis factor (TNF) or other growth factors, colony stimulating factors, or cytokines which stimulate the immune response and reduction or elimination of virus. The composition may also be administered with, or may include combinations along with immune cell antigen antibodies or immune cell modulators.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A protein, peptide, immune activator or agent can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like Accordingly, also encompassed herein is a composition comprising at least one of pcdh18, a domain or fragment thereof as described herein or nucleic acid sequences encoding same or an agent identified using a screening assay described herein and a pharmaceutically acceptable buffer, for use in treating a patient with pcdh18 expressing tumor, such as adenocarcinoma, wherein said composition alleviates symptoms of the pcdh18 expressing tumor in the patient when administered to the patient in a therapeutically effective amount. Such compositions may also have utility for use in prophylaxis for a patient at risk for developing a pcdh18 expressing tumor, including adenocarcinoma, wherein said composition prevents or alleviates symptoms in the patient when administered to the patient in an effective amount. Also encompassed herein is the use of a therapeutically effective amount of a composition comprising at least one of pcdh18, a domain or fragment thereof as described herein or nucleic acid sequences encoding same or an agent identified using a screening assay described herein and a pharmaceutically acceptable buffer in the manufacture of a medicament for treating a patient with an pcdh18 expressing tumor, such as adenocarcinoma, wherein the medicament alleviates or prevents symptoms of the pcdh18 expressing tumor when administered to the patient. Also encompassed herein is at least one of pcdh18, a domain or fragment thereof as described herein or nucleic acid sequences encoding same or an agent identified using a screening assay described herein and compositions thereof for use in treating cancer in a subject.

The peptide or agent containing compositions are conventionally administered intramuscularly, intravenously, as by injection of a unit dose, or orally, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of activation and immune response desired. Precise amounts of active ingredient required to be administered depend on the judgment of the practitioner and are peculiar to each individual. Suitable regimens for initial administration and follow on administration are also variable, and may include an initial administration followed by repeated doses at appropriate intervals by a subsequent injection or other administration.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Nucleic Acids

The present invention further provides an isolated nucleic acid encoding a protein, peptide, immune activator or agent of the present invention. Nucleic acid includes DNA and RNA. In a preferred aspect, the present invention provides a nucleic acid which codes for a polypeptide of the invention as defined above, including any one of SEQ ID NO: 9 or a fragment thereof as set out herein. See, for example, FIG. 10 and SEQ ID NOs: 11, 13, and 15.

The present invention also provides constructs in the form of plasmids, vectors, and transcription or expression cassettes which comprise at least one polynucleotide as above. The present invention also provides a recombinant host cell which comprises one or more constructs as above. A nucleic acid encoding any specific binding member as provided herein forms an aspect of the present invention, as does a method of production of the specific binding member which method comprises expression from encoding nucleic acid therefor. Expression may conveniently be achieved by culturing recombinant host cells containing the nucleic acid under appropriate conditions. Following production by expression, a specific binding member may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, adenocarcinoma cells and many others. A common, preferred bacterial host is *E. coli*. The expression of antibodies and antibody fragments in prokaryotic cells such as *E. coli* is well established in the art.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. The present invention also provides a method which comprises using a construct as stated above in an expression system in order to express a specific binding member or polypeptide as above.

Another feature of this invention is the expression of DNA sequences contemplated herein, particularly those encoding pcdh18 and domains, fragments, and peptides thereof, or an agent of the invention. As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences (sequences that control the expression of a DNA sequence operatively linked to it) may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

The invention also provides pcdh18 chimeric or fusion proteins. As used herein, a pcdh18 "chimeric protein" or "fusion protein" comprises a pcdh18 polypeptide operatively linked to a non-pcdh18 polypeptide. A "pcdh18 polypeptide" refers to a polypeptide having an amino acid sequence corresponding to full length pcdh18 polypeptide or a domain or fragment thereof, whereas a "non-pcdh18 polypeptide" refers to a polypeptide having an amino acid sequence corresponding to a protein which is not substantially homologous to the pcdh18 protein. In a particular embodiment, a pcdh18 fusion protein comprises at least one biologically active portion of a pcdh18 protein, e.g., an extracellular domain of a pcdh18 protein. Within the fusion protein, the term "operatively linked" is intended to indicate that the pcdh18 polypeptide and the non-pcdh18 polypeptide are fused in-frame to each other. The non-pcdh18 polypeptide can be fused to the N-terminus or C-terminus of the pcdh18 polypeptide.

For example, in one embodiment, the fusion protein is a GST-pcdh18 in which the pcdh18 sequences are fused to the C-terminus of the GST sequences. In another embodiment, the fusion protein is a pcdh18-HA fusion protein in which the pcdh18 nucleotide sequence is inserted in a vector such as pCEP4-HA vector (Herrscher, R. F. et al. (1995) Genes Dev. 9:3067-3082) such that the pcdh18 sequences are fused in frame to an influenza hemagglutinin epitope tag. Such fusion proteins can facilitate the purification of a recombinant pcdh18 protein.

A pcdh18 fusion protein can be produced by recombinant expression of a nucleotide sequence encoding a first peptide having pcdh18 activity, and a nucleotide sequence encoding a second peptide corresponding to a moiety that alters the solubility, affinity, stability or valency of the first peptide, for example, an immunoglobulin constant region. In a particular embodiment, the first peptide consists of a portion of the pcdh18 polypeptide (e.g., the ECD or a fragment thereof as presented in SEQ ID NO: 10 that is sufficient to confer pcdh18 homophilic binding/interaction). The second peptide can include an immunoglobulin constant region, for example, a human Cγ1 domain or Cγ4 domain (e.g., the hinge, CH2 and CH3 regions of human IgCγ 1, or human IgCγ4, see e.g., Capon et al. U.S. Pat. Nos. 5,116,964; 5,580,756; 5,844,095 and the like, incorporated herein by reference in its entirety). A resulting fusion protein may have altered pcdh18 solubility, binding affinity, stability and/or valency (i.e., the number of binding sites available per molecule) and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

In a particular embodiment, pcdh18 Ig fusion proteins include the extracellular domain portion or functional homophilic binding region thereof coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a pcdh18 polypeptide can be joined to DNA encoding the hinge, CH2 and CH3 regions of human IgGγ1 and/or IgGγ4 modified by site directed mutagenesis, e.g., as taught in WO 97/28267. Fusion proteins of, e.g., pcdh18 and an immunoglobulin fusion protein may be referred to interchangeably herein as "pcdh18Ig" or "pcdh18Fc". Other variations which incorporate the terms "Ig" or "Fc" may also be used.

pcdh18 fusion proteins of the invention are produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide or an HA epitope tag). A pcdh18 encoding nucleic acid can be cloned into such an expression vector such that the fusion moiety is linked in-frame to the pcdh18 protein.

In another embodiment, the fusion protein is a pcdh18 protein containing a heterologous signal sequence at its N-terminus. In certain host cells (e.g., mammalian host cells), expression and/or secretion of pcdh18 can be increased through use of a heterologous signal sequence.

The pcdh18 fusion proteins of the invention can be incorporated into pharmaceutical compositions and administered to a subject in vivo. Use of pcdh18 fusion proteins is useful for therapeutic modulation of an immune response to various tumors. Moreover, the pcdh18-fusion proteins of the invention, (e.g., full length protein or portions thereof) can be used as immunogens to produce anti-pcdh18 antibodies in a subject, to purify pcdh18 and in screening assays to identify molecules which inhibit homophilic interaction of pcdh18 molecules on, for example, CD8+ T cells and tumor cells.

Humanized antibodies specific for another ISR, programmed cell death-1 or programmed death-1 (PD-1), have shown great promise as immune modulators and are currently be assessed in Phase I and III clinical trials. The fully humanized anti-PD-1 monoclonal antibody is known as MDX-1106 binds to and blocks PD-1. Details pertaining to PD-1 and its role as an ISR, as well as methods for generating antibodies thereto and methods of using anti-PD-1 antibodies in the treatment of various cancers (including, e.g., certain types of advanced skin, kidney and lung cancers) are found, for example, in U.S. Pat. Nos. 7,105,328 and 7,700,301, the entire content of each of which is incorporated herein by reference.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Materials and Methods

Mice:
C57BL/6 male mice were obtained from Jackson Laboratories (Bar Harbor, Me.), were housed five per cage in a barrier facility, and were maintained on a 12 hr light/dark cycle (7 AM to 7 PM) with ad libitum access to food and water. A sentinel program revealed that tumor-bearing mice were Murine Hepatitis Virusnegative. Experiments involving animals were conducted with the approval of the New York University School of Medicine Committee on Animal Research.

Tumors:
MCA38 adenocarcinoma [5,7] (a gift of Nick Restifo, National Cancer Institute) was passaged from tissue culture plasticware by incubation in HBSS containing 3 mM EDTA followed by washing in HBSS. Cell viability was determined by Trypan Blue dye exclusion and 1-26105 cells were injected intraperitoneally in a volume of 0.1 ml of HBSS for tumor induction. Cells were passaged in vitro for 3-5 weeks following which new frozen stocks were thawed for usage.

Tissue Culture:
RPMI-1640 medium (Biowhittaker, Walkersville, Md.) was used for growth of MCA-38 cells and for culture of T cells as described [6]. Thymoma EL-4 (ATCC) was passaged by dilution of media and CTLL-2 cells were maintained in media supplemented with rIL-2.

Isolation of cells: Tumors were dissected, mechanically disrupted by passage through a tissue press, digested into single cell suspensions using collagenase, and TIL were isolated by immunomagnetic separation using type LS+ columns and anti-CD8a (or anti-CD4) conjugated magnetic beads (Miltenyi Biotec, Auburn, Calif.) as described previously [6]. Aliquots of isolated T cells were analyzed by flow cytometry and were routinely, 95% CD8+. TIL were used immediately after isolation for experiments ('non-lytic') except in some experiments where TIL were plated in complete RPMI-1640 medium (~2×10$^6$ cells/ml) for 6-18 h before usage ('lytic'). In some experiments TIL were further purified by FACS. Splenocytes and bone marrow cells were usually enriched for CD8+ T cells by negative selection magnetic immunobeading (Miltenyi Biotec) followed by FACS. In some experiments splenocytes were labeled with anti-CD11c, B220, CD4 or CD8 and sorted using a MoFlo Legacy high-speed sorter. Cells were collected in media and immediately reanalyzed for purity in a LSR-II cytometer. Cells were collected and placed in Trizol immediately for RNA isolation and RT-PCR.

cDNA Cloning of Pcdh-18:
Primers were designed with restriction sites that are absent within Pcdh-18 for cloning into pIRES (SacI and XmaI). The primers used were, Pcdh-18-SacI-Forward: 5' TTGAGCTCTGAGTGGCTGGAGGA (SEQ ID NO: 20), and Pcdh-18-XmaI-Reverse: 5' TTCCCGGGACAC-CTCGGGATCTTC (SEQ ID NO: 21). A 28-cycle RT-PCR using cDNA generated from lung as a template and a high fidelity Taq (Phusion Taq, Life Technologies) generated a 3.4 Kbp product. The band was extracted from an agarose gel and purified using the 'PCR clean up kit' (Denville). pcdh-18-pIRES was then digested with SacI and XmaI, the products separated in an agarose gel, and the linear plasmid was extracted and purified. The plasmid was dephosphorylated and ligated to the PCR product (Ligation Kit, Life Technology) and used to transform DH5α. A selected clone was subjected to restriction digestion to confirm the presence of pcdh-18 which was also confirmed by DNA sequencing.

Generation of a Pcdh-18 Point Mutant (Y842F):
PCR primers were selected with restriction sites that are present within pcdh-18, KpnI (cDNA nucleotide 2287) and SspI (cDNA nucleotide 2557). The primers used were, pcdh-18-Y842-Forward: 5' CACCAGGGGCA ATTTCAGCCACGGCCA (SEQ ID NO: 22), and pcdh-18-Y842-Reverse: 5' AAGCATGGAGAGAAGCTGCGA-GACCTC (SEQ ID NO: 23). The forward primer contains the mutated nucleotide (in bold T instead of an A) that generated the single point mutation in the product. A 30-cycle PCR using pcdh-18-pIRES as a template and a high fidelity Taq polymerase (Phusion Taq, Life Technologies)

generated a 270 bp product. The band was extracted from an agarose gel and purified using 'PCR clean up kit' (Denville). pcdh-18-pIRES was digested with KpnI and SspI. The digested products were separated in an agarose gel and the linear plasmid was extracted and purified. The plasmid was dephosphorylated and ligated to the PCR product (Ligation Kit, Life Technology) and used to transform DH5a. A selected clone was subjected to restriction digestion to confirm the presence of pcdh-18 and confirmed by sequencing.

Transfection of Primary CD8+ T Cells:

Splenocytes were isolated, plated in complete media at $5 \times 10^6$ cells supplemented with 10% of conditioned media from 2C11 hybridoma. After 36 h cells were collected and re-plated at $2 \times 10^6$ cells/well supplemented with 10% of conditioned medium from an IL-2 producer line. 0.008 mg of plasmids was used to transfect by nucleofection (using program X-001, Lonza). Cells were cultured for 4 h in complete media containing IL-2. For signaling experiments, cells were then cultured in RPMI medium lacking IL-2 and FBS for 3-4 h prior to any experiment.

Gene Array Sample Preparation:

Ten spleens were pooled from 62 week old C57BL/6 male mice and enriched for CD8+ T cells by negative selection using a cocktail of biotinylated antibodies to deplete CD4, CD11c, CD11b, MHC-11, B220, and NK cells. Cells were then stained for CD8, CD44, CD62L, and CD127 and sorted (using a iCyt Reflection parallel cell sorter). Cells were collected and cultured ($0.5 \times 10^6$ cells/well) in 10% complete RPMI media supplemented with 0.005 ugr Con A and RNA prepared using TRIZOL and the 'RNeasy clean-up kit' (Invitrogen) after activation for different times.

We established transcriptional profiles for 6 time points after T cell activation (4, 6, 8, 16, 20, 24 h) including a zero h time point (prior to activation). RNA was isolated by standard procedures and its quality was assessed by the NYU Center for Health Informatics and Bioinformatics. cDNAs were hybridized to GeneSpring arrays using the mouse genome MOE430 2.0 array (Affymetrix) which interrogates ~45,000 transcripts. The data discussed herein have been deposited in NCBI's Gene Expression Omnibus and are accessible through GEO Series accession number GSE34618.

Analysis of Gene Expression Data:

Utilizing GeneSpring 7.2 (Agilent), raw Affymetrix CEL files were processed and normalized by applying the Robust Multi-Array Average expression measure (RMA) and baseline scaling. These metrics were further filtered to obtain 35,160 "valid genes", representing transcripts (gene probes) that were detected as "Present" in at least one sample across all tested time points. To obtain a subset of variable genes, we calculated the coefficient of variation (CV) for each transcript and generated a set of 5274 "active genes" containing the transcripts with the highest (15% of the total) CV scores. For discovering prominent expression patterns we used the EXPANDER program [25] and executed CLICK, a novel clustering algorithm [26] that makes no prior assumptions on the structure or the number of the clusters. CLICK discovered five unique expression patterns. Cluster 4 has a unique undulating kinetics and includes pcdh18 that peaks twice within 24 h. We utilized functional annotations of murine genes provided by the Murine Genome Informatics, which uses the standard vocabulary introduced by the Gene Ontology (GO) consortium. Enriched functional categories (p#0.01, after correction for multiple testing) were identified in each of the gene sets using EXPANDER, in which hypergeometric calculation is used to determine overrepresented GO functional categories in a target set relative to a background set (the entire collection of putative murine genes) [27]. To avoid biases, genes represented by multiple probe sets were counted only once.

Quantitative RT-PCR Analysis:

Total RNA was isolated (Trizol), converted into cDNA using Superscript II reverse transcriptase (Invitrogen, Carlsbad, Calif.), and was analyzed by real-time PCR ('SYBR Green PCR master mix', Applied Biosystems, Carlsbad, Calif.) using 200 fmol/uL primer concentration for 40 cycles. SYBR incorporation into PCR products was monitored using a model 7500 real-time PCR system (AB). Dissociation curve analysis (SDS 2.0 software) assessed the specificity and integrity of the PCR products. Degradation of total RNA used in the cDNA synthesis was normalized by determining the threshold cycle (Ct) values for target genes and housekeeping genes (β-actin and GAPDH) in each sample. Target gene/housekeeping gene ratios were calculated as: ratio=$2^{[Ct(housekeeping)-Ct(target)]}$. Relative mRNA levels are expressed as 'fold induction' for samples at different times of activation with ConA compared to time '0' (ca 2-72 hr). PCR reactions were conducted in triplicate and repeated at least once with unique samples.

Primers Used were:

Pcdh18, Pcdh12, Pcdh8, IL-2, TNF, IFN, bactin, GAPDH, granzyme B, PD-1, PD1-L, Dab1, Dab2a, Dab2b. Sequences provided in Table 1 below:

TABLE 1

Primers for qPCR: (Ta = annealing temperature).
The primers listed in Table 1 are designated as follows:

| | |
|---|---|
| CCACGGAAATTGTCTGGTTG, | (SEQ ID NO: 24) |
| TGCTGCATAATCAGCTACGG, | (SEQ ID NO: 25) |
| ACCATCACTTGTCTCCTCGGCTGT, | (SEQ ID NO: 26) |
| CGTCCCGAGGTACAAGGCGG, | (SEQ ID NO: 27) |
| CACTGATACCAGCCAATCCC, | (SEQ ID NO: 28) |
| AATCAAGCTTGCAAGAGATTTGT, | (SEQ ID NO: 29) |
| ACCAGCGCCAAGAAAGACT, | (SEQ ID NO: 30) |
| ATCAGCTTGGCTTTGACCG, | (SEQ ID NO: 31) |

TABLE 1-continued

| | |
|---|---|
| GTGAGGGGCAATGACAATCT, | (SEQ ID NO: 32) |
| GAAGAGCTGTCGAGCCTGTT, | (SEQ ID NO: 33) |
| CAGGCTGGGTAGAAGGTGAG, | (SEQ ID NO: 34) |
| CATTCACTTGGGCTGTGCT, | (SEQ ID NO: 35) |
| AGCAACAGCAAGGCGAAAA, | (SEQ ID NO: 36) |
| CTGGACCTGTGGGTTGTTGA, | (SEQ ID NO: 37) |
| CATGTAGGGTCGAGAGTGGG, | (SEQ ID NO: 38) |
| CCTCCTGCTACTGCTGACCT, | (SEQ ID NO: 39) |
| GTGCTCCTTGTCAACAGCG, | (SEQ ID NO: 40) |
| GGGGAGTTTCAGGTTCCTGTA, | (SEQ ID NO: 41) |
| AAGTCATGCTGGCTCCACAG, | (SEQ ID NO: 42) |
| CACTGATACCAGCCAATCCC, | (SEQ ID NO: 43) |
| TGTGTCCGTCGTGGATCTGA, | (SEQ ID NO: 44) |
| CCTGCTTCACCACCTTCTTGA, | (SEQ ID NO: 45) |
| AGAGGCACTCCCCCAAAAGAT, | (SEQ ID NO: 46) |
| GCAGGAATGAGAAGAGGCTGA, | (SEQ ID NO: 47) |
| TTTGGGGCGCGATTCTCCGA, | (SEQ ID NO: 48) |
| GGACTCTGCACTCCTCCGTA, | (SEQ ID NO: 49) |
| ATCTCGGGCCGAGAAGCTGA, | (SEQ ID NO: 50) |
| CGGGGACACGTATCTGCTAC, | (SEQ ID NO: 51) |
| CCGTGAAAAGATGACCCAGATC, and | (SEQ ID NO: 52) |
| CATACCCAGGAAGGAAGGCTG. | (SEQ ID NO: 53) |

| GENE | 5'→3' SEQUENCE | qPCR Ta |
|---|---|---|
| PD-1L | FW CCACGGAAATTGTCTGGTTG (SEQ ID NO: 24) | 60 |
| PD-1L | RV TGCTGCATAATCAGCTACGG (SEQ ID NO: 25) | 60 |
| PCDH-19 | FW ACCATCACTTGTCTCCTCGGCTGT (SEQ ID NO: 26) | 58 |
| PCDH-19 | RV CGTCCCGAGGTACAAGGCGG (SEQ ID NO: 27) | 58 |
| DAB-2b | FW CACTGATACCAGCCAATCCC (SEQ ID NO: 28) | 58 |
| DAB-2b | RV AATCAAGCTTGCAAGAGATTTGT (SEQ ID NO: 29) | 58 |
| DAB1 | RV ACCAGCGCCAAGAAAGACT (SEQ ID NO: 30) | 58 |
| DAB1 | FW ATCAGCTTGGCTTTGACCG (SEQ ID NO: 31) | 58 |
| PCDH-12 | FW GTGAGGGGCAATGACAATCT (SEQ ID NO: 32) | 56 |
| PCDH-12 | RV GAAGAGCTGTCGAGCCTGTT (SEQ ID NO: 33) | 56 |
| PD-1 | FW CAGGCTGGGTAGAAGGTGAG (SEQ ID NO: 34) | 60 |

TABLE 1-continued

| Gene | Dir | Sequence | Temp |
|---|---|---|---|
| PD-1 | RV | CATTCACTTGGGCTGTGCT (SEQ ID NO: 35) | 60 |
| IFN | FW | AGCAACAGCAAGGCGAAAA (SEQ ID NO: 36) | 58 |
| IFN | RV | CTGGACCTGTGGGTTGTTGA (SEQ ID NO: 37) | 58 |
| GRANZYME-B | FW | CATGTAGGGTCGAGAGTGGG (SEQ ID NO: 38) | 58 |
| GRANZYME-B | RV | CCTCCTGCTACTGCTGACCT (SEQ ID NO: 39) | 58 |
| IL-2 | FW | GTGCTCCTTGTCAACAGCG (SEQ ID NO: 40) | 58 |
| IL-2 | RV | GGGGAGTTTCAGGTTCCTGTA (SEQ ID NO: 41) | 58 |
| DAB2a | RV | AAGTCATGCTGGCTCCACAG (SEQ ID NO: 42) | 58 |
| DAB2a | FW | CACTGATACCAGCCAATCCC (SEQ ID NO: 43) | 58 |
| GAPDH | FW | TGTGTCCGTCGTGGATCTGA (SEQ ID NO: 44) | 56 |
| GAPDH | RV | CCTGCTTCACCACCTTCTTGA (SEQ ID NO: 45) | 56 |
| TNF | FW | AGAGGCACTCCCCCAAAAGAT (SEQ ID NO: 46) | 58 |
| TNF | RV | GCAGGAATGAGAAGAGGCTGA (SEQ ID NO: 47) | 58 |
| PCDH-18 | FW | TTTGGGGCGCGATTCTCCGA (SEQ ID NO: 48) | 56 |
| PCDH-18 | RV | GGACTCTGCACTCCTCCGTA (SEQ ID NO: 49) | 56 |
| PCDH-8 | FW | ATCTCGGGCCGAGAAGCTGA (SEQ ID NO: 50) | 56 |
| PCDH-8 | RV | CGGGGACACGTATCTGCTAC (SEQ ID NO: 51) | 56 |
| b-ACTIN | FW | CCGTGAAAAGATGACCCAGATC (SEQ ID NO: 52) | 56 |
| b-ACTIN | RV | CATACCCAGGAAGGAAGGCTG (SEQ ID NO: 53) | 56 |

Antibodies:

Antibodies, reagents, and procedures used in immunoblotting and flow cytometry were as described previously [5]. Additional Ab used were: phospho-p56lck (Ab Y505/527, Cell Signaling Technology, Beverly, Mass.), phosphotyrosine (clone 4G10, Cell Signaling Technology, Beverly, Mass.), p56lck (mouse Ab 3A5; Santa Cruz Biotechnology), p56lck (Ab 2102; Santa Cruz Biotechnology), rabbit anti-Pcdh18 was prepared by creation of a GsT fusion protein containing the cytoplasmic domain of Pcdh18 and hyperimmunization of rabbits. Rabbit anti-pcdh18 with a similar specificity was also purchased (HPA017976, Sigma Chemical Company, St. Louis, Mo.).

Flow Cytometric Analysis:

All analyses were performed in general as described previously [5]. Primary Ab were added to cells ($10^6$/mL) at empirically determined optimal concentrations. After incubation at 4° for 20 min, cells were washed once with 1 ml of FACS wash (PBS, 2% FBS) and fixed with 1% paraformaldehyde before analysis. For analysis of intracellular molecules, cells were first fixed and permeabilized using BD cytofix/Cytoperm (BD-bioscience). When used, secondary antibodies were diluted in the perm-wash buffer. Species-matched, control primary Ab was used to determine parameters and settings for flow cytometry.

T Cell Activation:

TIL (or activated primary splenocytes 4 h after transfection) were isolated and incubated in serum-free RPMI1640 medium for 3 h, washed, resuspended in cold compete medium, and anti-CD3 epsilon added for 30 min. Samples were collected and resuspended in warm medium containing anti-hamster Ig for 1, 2, or 5 min before preparation of detergent extracts or fixation for flow cytometry for staining with activation-specific anti-Zap70.

Calcium Flux:

After transfection of primary spleen cells as described above, cells were incubated in 1% FBS RPMI1640 containing with 0.001 mg/mL biotinylated anti-CD3, 0.001 mg/mL biotinylated anti-CD8b, anti-CD8 PE, 0.0032 mg/mL Indo-1 AM (eBioscience) and 2 mM Probenecid (Sigma) for 30 minutes at RT° in the dark. Samples were washed twice with serum-free RPMI, then resuspended at $1\times10^7$ cells mL. Cells were equilibrated to 37° five min before reading on a LSRII and were activated by crosslinking with 0.0125 mg/mL of streptavidin (Pierce).

Listeria Monocytogenes:

Listeria monocytogenes (wt and recombinant expressing ova, a gift of Eric Pamer, MSKCI) were grown in BHK media and diluted in PBS for mouse injection (iv). A dose of $5-10\times10^3$ bacteria was sufficient to induce infection in wt mice which was cleared in 3-4 days as assessed by colony formation on agar plate of extracts of various organs.

Chromium-Release Assay:

Cytolysis activity of TIL or transfected primary lytic effector cells was assessed in standard re-directed [$^{51}$Cr]-release assays using P815 cells performed in quadruplicate wells for each E:T ratio exactly as described [14]. Maximal release from target cells was determined by treatment of cells with 1% Triton X-100, spontaneous release was determined from cultures of labeled target cells incubated with medium only, and the formula used for determination of specific lysis was: (experimental release−spontaneous release)/(maximal release−spontaneous release)×100.

Results

Identification of a p56$^{lck}$ Binding Protein in TIL.

Analysis of p56$^{lck}$ activation status in nonlytic TIL by immuneprecipitation and reciprocal immunoblotting using Ab reactive with the phosphorylated form of the src family kinase inhibitory motif (centered on Y505) showed that this motif in p56$^{lck}$ was not appreciably phosphorylated upon conjugation in vitro with cognate tumor cells (FIG. 1a). However, a high molecular weight band (~120 kD) co-immuneprecipitated with p56$^{lck}$ and was recognized by motif-specific anti-pY505. The equivalent experiment using TIL that were briefly cultured in vitro before analysis (and therefore had re-established proximal TCR signaling and lytic function [5]), showed the presence of the 120 kD band, but its abundance and conjugation-dependent phosphorylation was dramatically reduced compared to nonlytic TIL (FIG. 1a, lower panel). (Regulation of p56$^{lck}$ centered on motifs Y394 and Y505 is shown diagrammatically in FIG. 1b). Since anti-peptide Ab may have significant non-specific crossreactivity, this analysis was repeated using anti-pY Ab (4G10) and produced equivalent results (FIG. 1c). A trivial possible basis for this observation (dimerization of p56$^{lck}$ during cell lysis) was eliminated by reciprocal immunoblotting using a second Ab for blotting that is reactive with a different epitope of p56$^{lck}$ which did not detect the ~120 kD protein (FIG. 1d).

These observations implied that a ~120 kD protein interacts with p56" in nonlytic TIL, contains the epitope recognize by anti-pY505, and is rapidly tyrosine phosphorylated upon contact with cognate tumor cells. BLAST analysis performed using as search query the p56" inhibitory motif peptide sequence to which anti-pY505 was raised (EGQYQPQP; SEQ ID NO: 1) identified Protocadherin-18 ('pcdh18', [8]) as a polypeptide comprising the following sequence: QGQYQPRP (SEQ ID NO: 2). Sequence comparison of protocadherin and related cadherin gene families revealed that pcdh18 is the only protocadherin member that contains a Y residue in the context of a Q/P motif (FIG. 2a) and also is the only non-src gene in the database to contain the src inhibitory motif. Expression of pcdh18 was examined by RT-PCR analysis of various tissues and assessed with respect to closely-related pcdh genes for specificity control (pcdh8, FIG. 2b and pcdh12, FIG. 2d). pcdh18 RNA is widely expressed in adult tissues and is notably expressed in cognate MCA38 tumor, whereas expression of other pcdh genes is more restricted.

In order to identify the spleen cell type that expresses pcdh18, purified splenocytes from young control mice were analyzed by RT-PCR in comparison to nonlytic TIL and the CD8$^+$ T cell line CTLL-2 (FIG. 2c). No signal was detected from major cell types including NK cells (even after activation when lytic function and IFN expression is high). A modest PCR signal was detected in CD11c$^+$ bone marrow-derived DC that increased upon activation. Cells isolable with the spleen capsule express pcdh18, possibly accounting for the PCR signal obtained from total spleen preparations. To determine if pcdh18 expression was a function of activation status, CD8$^+$ spleen cells from young naive mice were treated with ConA but found to be negative (FIG. 2c). Nonlytic CD8$^+$ TIL express pcdh18 RNA immediately upon isolation whose levels undulate with time of cell activation in vitro (FIG. 2d). CD4$^+$ TIL purified from the same tumor as CD8$^+$ TIL do not express pcdh18. Inhibitory signaling receptor PD-1 RNA is not detected in nonlytic TIL but is induced after brief culture in vitro, as is its ligand PD-1L.

We considered the possibility that the differentiation status of spleen cells may account for the inconsistent PCR findings and next compared FACS-purified CD4$^+$, CD8$^+$, CD11c$^+$, and CD45$^+$ cells from young (4 week) and aged (>48 weeks) control mice using qRT-PCR (FIG. 2e). CD8$^+$ T cells of aged mice contain pcdh18 RNA and, since older mice contain a greater percentage of memory T cells compared to younger mice, prompted consideration that pcdh18 is expressed in CD8$^+$ memory cells. Further supporting this notion is the previous observation that TIL are effector memory cells [6].

Pcdh18 is Expressed in Memory T Cells.

Figure 3:
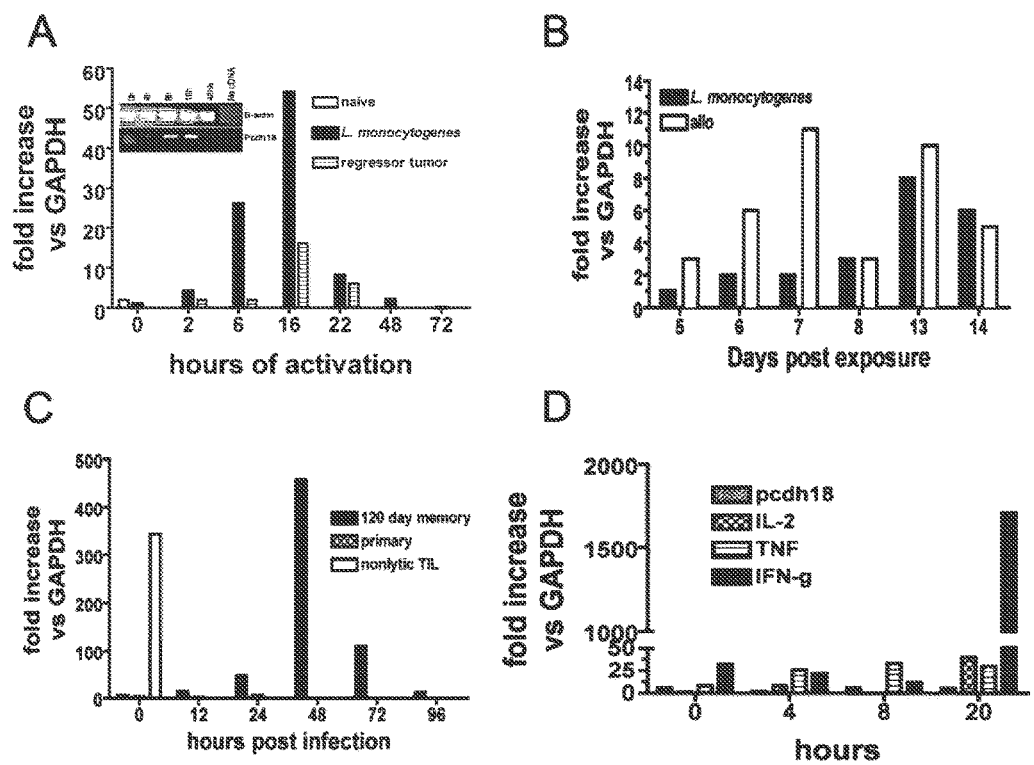
FIG. 3A-D shows RNA analyses of spleen cells after induction of memory in vivo. A) qRT-PCR analysis of spleen CD8+ T cells isolated from BL/6 mice previously infected with either 5,000 recombinant *Listeria monocytogenes*, buffer controls, or EL4 cells at a subtumorigenic dose ('regressor tumor'). 28 days after exposure spleen CD8+ T cells were purified, activated in vitro with Con A for the indicated times, RNA prepared and qRT-PCR performed as described in 'Materials and Methods'. (This analysis has been performed using mice previously infected for times up to 1 year with similar results). Insert shows gel analysis of pcdh18 RT-PCR expression from *L. monocytogenes*-immune mice. B) qRT-PCR analysis of purified CD8+ T cells from mice injected with *L. monocytogenes* or allogeneic H-2D spleen cells. C) qRT-PCR analysis of purified CD8+ T cells from mice originally infected with *L. monocytogenes* which were challenged by in vivo infection by *L. monocytogenes*. Spleens were isolated at the indicated times following challenge. Age-matched naive mice received only primary exposure given at the time of secondary challenge. Nonlytic TIL are shown for comparison. D) qRT-PCR analysis of purified control CD8+ spleen T cells and activated in vitro with anti-CD3e for the indicated times before RNA isolation and analysis by qRT-PCR. The data shown are representative of multiple repetitions.

A memory response was induced by: infection with Listeria monocytogenes (and clearance), injection of allogeneic splenocytes (H-2D), or inoculation of a sub-tumorigenic dose of a transplantable syngeneic tumor (EL-4). At different times post antigen exposure (3 weeks up to >50 weeks) spleen total CD8$^+$ T cells were isolated and pcdh18 expression analyzed. Expression of pcdh18 was low, but in cells from immunized mice was rapidly and robustly increased upon in vitro activation (FIG. 3a). Induction started ~2 h post activation and by ~24 h expression was reduced close to that of non-activated cells. The rapid kinetics and transient nature of induction in cells following development of memory due to antigen exposure suggests pcdh18 is an immediate-early response gene of the memory response.

CD8$^+$ T cells isolated following primary in vivo treatment express low levels (FIG. 3b) in comparison to re-activation of a memory response (approximately 6-fold less). Additionally, mice were infected with L. monocytogenes (or injected with allogeneic spleen cells, dns) to establish memory and subsequently challenged in vivo (FIG. 3c, pcdh18 expression in CD8$^+$ TIL is shown at one time point for comparison). After priming by infection and resting before re-challenge (for more than four months in this case), pcdh18 was rapidly and robustly induced in total CD8$^+$ splenocytes upon in vivo challenge showing that pcdh18 expression is not a phenomenon restricted to the in vitro experimental model. Control age-matched mice given only challenge ('primary') showed minimal pcdh18 expression, reinforcing the notion that pcdh18 is expressed in memory CD8$^+$ T cells. Transcriptional regulation of expression following in vivo re-activation, by either re-infection with *L. monocytogenes* (FIG. 3c) or re-injection of allogeneic cells (dns) demonstrates the physiological relevance of pcdh18 expression. CD4$^+$ T cells were also isolated from these groups of mice and did not express pcdh18 RNA, dns. Expression was never detected in CD4$^+$ T cells, irrespective of whether the CD4+ cells are TIL, naive or memory cells (FIG. 2c). Expression of pcdh18 in CD8$^+$ cells of naive mice following activation in vitro was assessed in comparison to selected cytokines (FIG. 3d). pcdh18 is not appreciably expressed in activated naive CD8$^+$ T cells. Characteristic of naive cells, expression of effector phase cytokine RNAs is minimal until late in activation at which point IFN is robustly transcribed (FIG. 3d).

Analysis of Pcdh18 Expression in Memory Cells.

Figure 4:
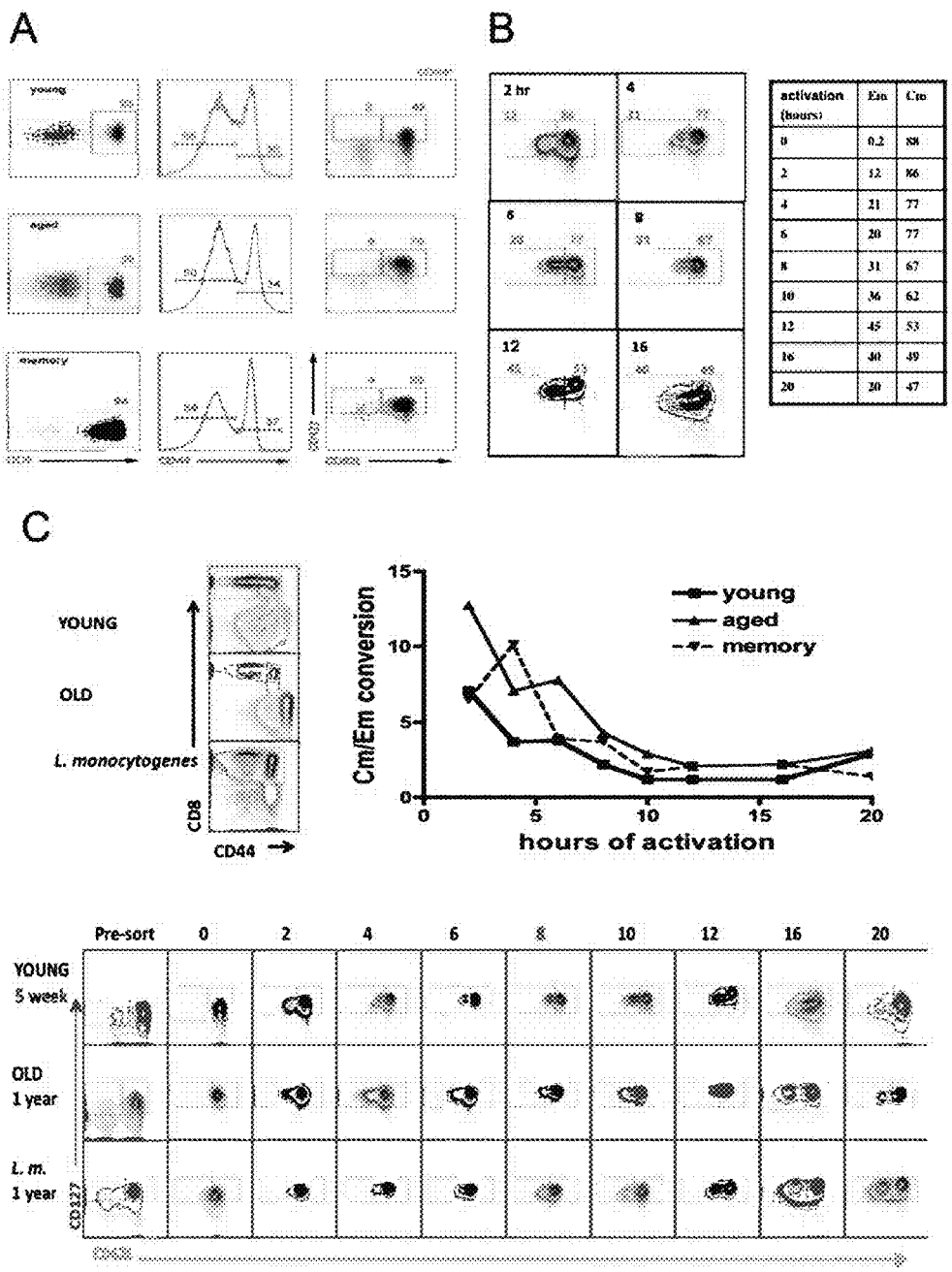
FIG. 4A-C shows conversion of Cm into Em cells upon activation in vitro. A) FACS purification of spleen CD8+ CD44$^{hi}$CD62L$^{lo}$CD127$^{hi}$ (Effector-memory) and CD44$^{hi}$CD62L$^{hi}$CD127$^{hi}$ (Central-memory) cells obtained from young (<5 week) and >50 week old naive, and 50 week old mice that were previously injected with allogeneic spleen cells as indicated. Following sorting, an aliquot of cells was immediately taken for RNA isolation without activation. Analyses in the left panels are gated on CD8+ cells and show the distribution of CD44+ cells. Analyses in the right panels show Em and Cm cells within the CD44$^{lo}$ and CD44$^{hi}$ populations as indicated. B) Cm and Em cells were isolated by FACS from young, old, and memory (*L. monocytogenes*-infected) mice and activated in vitro with ConA for the indicated times before qRT-PCR. The % of CD8+CD44$^{hi}$ cells as CD62L$^{lo}$CD127$^{hi}$ (Em) and CD62L$^{hi}$CD127$^{hi}$ (Cm from the 'young' cohort are shown in the table. Flow cytometry analyses of some samples from the kinetic experiment are shown to illustrate gating. C) Enriched CD8+ spleen cells prior to sorting are shown in the left panels. After labeling, Cm were isolated and activated in vitro. The recovery of Em and Cm cells was determined by flow cytometry after re-staining and flow cytometric analysis. Shown are the FACS analyses after the indicated times of Cm activation. Also shown is the number of Cm and Em cells derived from in vitro activation of Cm cells represented as a ratio of Cm to Em cells at the various times of analyses.

In order to determine if pcdh18 is preferentially expressed in cells of a given differentiation state, CD8$^+$ central memory T cells ('Cm', CD44$^{hi}$CD62L$^{hi}$CD127$^+$) were FACS-purified from young (4 weeks), aged (ca 1 year), or mice that had been infected with *L. monocytogenes* >10 months prior ('memory'). Central memory cells represented the major population of CD8$^+$CD44$^{hi}$ cells and effector memory cells were ~4% of cells respectively in each group of mice (FIG. 4a). Preliminary experiments suggested that upon activation of purified Cm cells in vitro, pcdh18 was expressed starting at ~2 h coincident with conversion to the effector memory phenotype (loss of CD62L). To extend those observations, following in vitro activation of endogenous Cm, Cm and Em cells were purified by FACS before RNA analysis by qRT-PCR (FIG. 4b+c). Selected FACS data for young mice is shown in FIG. 4b where a reciprocal relation is seen between decreased recovery of Cm cells and increased Em cells (as a percentage of live cells) as a function of time of activation. The number of Cm and Em cells recovered at various times after activation in vitro was plotted as a ratio of Cm to Em cells ('Cm/Em conversion', FIG. 4c). Aged mice had greater starting numbers of Cm cells, thus the ratio is initially higher for that group, but rate of loss of CD62L upon activation in vitro is very similar between the three groups. For all groups of mice the percentage of Cm cells declined steeply at early times of activation (FIG. 4c). Conversion of Cm (CD62L$^{hi}$) to Em (CD62L$^{lo}$) cells after in vitro activation likely reflects a combination of factors (including death) but primarily differentiation.

pcdh18 qRT-PCR of FACS re-purified Cm and Em cells following in vitro activation of endogenous Cm cells is shown in FIG. 5a. Even after activation for extended time, Cm cells from each model expressed comparatively low levels of pcdh18 RNA. In contrast, Em cells of aged and memory mice express robust levels even at the earliest activation time (2 h). The pattern of expression in Em cells was different between aged and memory mice and in aged mice levels undulated over the assay period with maxima approximately every 6 h. This temporal pattern reflects expression as determined by gene array analysis performed on a separate biological sample of Cm cells from aged mice (FIG. 5a, bottom panel). [In the array analysis Cm cells were activated in vitro but were not re-purified (to eliminate Em cells) before RNA isolation and thus contain CD62L$^{lo}$ cells that differentiate in vitro under these conditions.]

Results demonstrating a high level of expression of IFN, IL-2 and grzB in newly-differentiated Em cells from mice in which a memory response was deliberately induced (by *L. monocytogenes* infection) supports the idea that CD44$^{hi}$CD62L$^{lo}$CD127$^{hi}$ cells in immune ('memory') mice contain bona fide Em cells and young mice do not. Cm cells (CD62L$^{hi}$CD127$^{hi}$) show an obverse pattern of those cytokines associated with the effector phase. Collectively considered, pcdh18 is expressed relatively poorly in Cm cells, whereas in Em cells the kinetics of expression closely follows the pattern of grzB, IFN, and IL-2 which is consistent with the idea that pcdh18 expression is restricted to recently activated Em cells.

In order to evaluate the expression of pcdh18 in a different population of memory cells total CD8$^+$ T cells from bone marrow were analyzed (FIG. 5b). pcdh18 expression trended with paradigmatic RNAs of memory cells (IFN and grzB) in that expression was greater in old versus young mice supporting the generality of our findings.

Pcdh18 Expression in Primary CD8$^+$ Lytic T Cells.

Spleen cells activated in vitro with anti-CD3 (followed by IL-2 treatment) expand a population of CD8$^+$ CD44$^{hi}$ cells coincident with development of lytic function (FIG. 6a) [9]. Interestingly, these cells resemble memory cells in terms of being CD62L$^{hi}$CD127$^+$ and upon activation resemble Em cells in that they start to lose expression of CD62L. Since these cells do not contain pcdh18 RNA (FIG. 3d), in order to assess the effect of pcdh18 expression on effector phase function, pcdh18 was expressed in these cells. A cDNA encoding pcdh18 was obtained from a TIL library, sequenced and found to be in agreement with the published sequence. An Ab raised to a recombinant cytoplasmic domain of pcdh18 used in reciprocal immunoblotting of TIL extracts (FIG. 6b top) confirmed the identity of pcdh18 (FIG. 1a). Expression of pcdh18 protein in transfected primary lytic effector cells was confirmed by flow cytometry analysis of where ~32% of PI$^-$CD8$^+$ lytic effector cells are pcdh18$^+$ (FIG. 6b).

Cells transfected with control vector form prominent clusters upon activation ~24 h post transfection (FIG. 6c). The number and size of clusters in control plasmid transfected cells increased with culture time reflecting cell division. However, cells transfected with pcdh18 form dramatically fewer and smaller clusters implying an effect on activation. Expression of pcdh18 containing a point mutation in the src inhibitory domain homology [QGQYQP (SEQ ID NO: 19), Y842F] completely reverses the effect on cluster formation implying phosphorylation of the motif is important in pcdh18 function (see below). Similarly, expression of cytokine RNA in pcdh18-transfected cells was significantly diminished compared to controls (FIG. 6d). Cytokine PCR analyses of nonlytic and lytic TIL are shown for comparison. Further, analysis of AICD in pcdh18-expressing cells (bottom panels in FIG. 6d) showed a dramatic reduction in both cell recovery and viability: cells expressing pcdh18 are more Annexin V$^+$ (early apoptosis) and PI$^+$/Annexin V$^+$ (late apoptosis, FIG. 6d). Indeed, the induction of AICD by pcdh18 expression in primary T cells and high-density culture is reminiscent of PD-1 which upon ligation and TCR activation also causes AICD [10-12]. Similar to the effect on cluster formation, expression of the Y842F mutant significantly reverses enhanced AICD caused by wt pcdh18. In addition, more cells are recovered when transfected cells are not activated in vitro showing a requirement for activation in induction of cell death.

Figure 6:
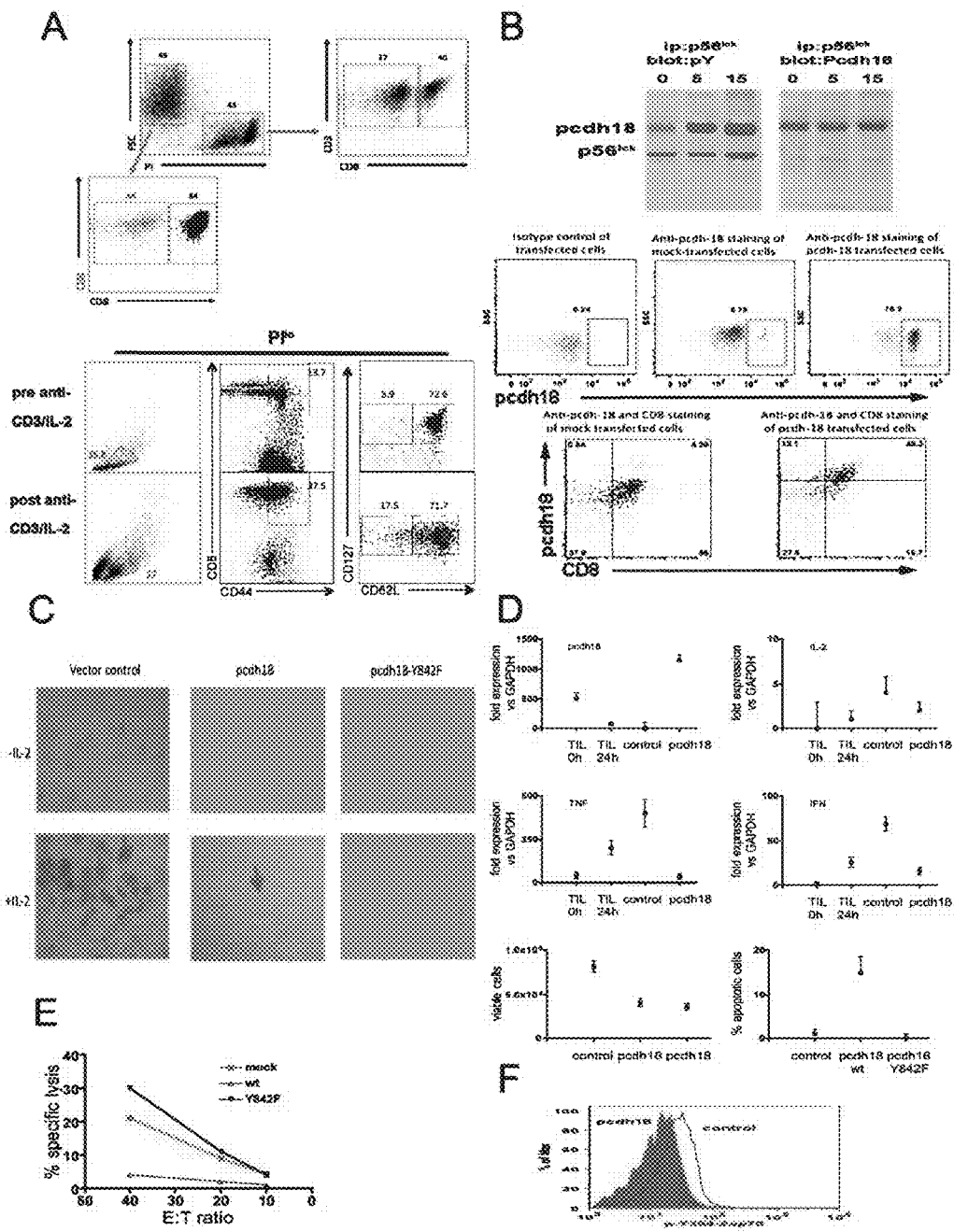
FIG. 6A-F shows biochemical and functional analyses of lytic T cells transfected with pcdh18. A) Flow cytometry analysis of primary lytic effector cells generated from spleens of 7 week old mice (prepared as described in 'Materials and Methods'). PI$^{lo}$ cells are >80% CD8+, PI$^{hi}$ cells are ~40% CD8+ (top panel). >70% of CD8+ CD44$^{hi}$ cells are CD62L$^{hi}$CD127$^{hi}$ (bottom panel). B) (top) Reciprocal immunoblot of p56$^{lck}$ isolated from nonlytic TIL. Analysis was performed as described in FIG. 1a (after conjugation with cognate MCA38 tumor cells for 0, 5, or 15 min as indicated and immunoprecipitated with anti-p56$^{lck}$ Ab 2102—left panels—or Ab 3A5-right panels) and blots were probed with anti-pY or anti-Pcdh18 as indicated. (bottom) Expression of pcdh18 protein in transfected effector cells by flow cytometry was as described in 'Materials and Methods'. Cells were stained with control or anti-pcdh18 Ab as indicated (top). C) Phase contrast microscopy of transfected cells. Effector cells were transfected as indicated and cultured in vitro in the presence or absence of IL-2 for ~24 h before microscopy. Arrows indicate cell clusters. D) RNA was extracted from transfected effector cells ('control' or 'pcdh18'), nonlytic TIL ('TIL 0 h'), or lytic TIL that were activated with anti-CD3 for 4 hours ('TIL 24 h') and used for cytokine qRT-PCR, or cells were assessed for viability (PI and Annexin V staining), as described in 'Materials and Methods'. In the viability assay two different plasmid constructs were used in separate experiments (bottom left panel) or the Y842F mutant (bottom right panel). E) transfected effector cells were assayed for lytic function by re-directed cytolysis assay as described in 'Materials and Methods'. F) Transfected cells were assayed for binding of anti-Zap70 pY493 after permeabilization following activation with anti-TCR for 2 min as described in 'Material and Methods'.

Expression of pcdh18 in primary effector cells also inhibited cytolysis (FIG. 6e), calcium flux, and activation of Zap70 (FIG. 6O confirming a site of action in the proximal TCR pathway. Similar to TIL or transfected primary CD8$^+$ T cells (though less robustly), we determined that CD44$^+$ CD62L$^+$pcdh18$^+$ endogenous Cm cells in aged mice have diminished calcium flux and Zap70 activation compared to CD44$^-$ naive cells derived from the same mouse. Wildtype pcdh18 was shown to bind to p56$^{lck}$ (FIG. 1) and phosphorylation of Y842 is required for inhibition of T cell functions (FIG. 6). Thus, pcdh18 is a strong candidate to mediate the effector phase defects in nonlytic TIL since each of these characteristic biochemical and functional deficiencies in transfected primary effector cells phenocopy nonlytic TIL [5-7, 13, 14].

DISCUSSION

Collectively, our observations suggest that upon activation of CD8$^+$ memory cells, pcdh18 interacts with p56$^{lck}$ and that the binding of p56$^{lck}$ by pcdh18 is causal to the failure to activate ZAP70 and subsequent deficient effector phase function. Thus, we have identified a novel p56$^{lck}$ binding protein that functions as an inhibitory signaling receptor during the effector phase in activated memory cells. pcdh18 is not only an inhibitory signaling receptor that can arrest the effector phase, but it is the first described marker that uniquely identifies CD8$^+$ T cells of memory origin.

In accordance with the results presented herein, identification and design of agents that inhibit pcdh18/pcdh18 intercellular interaction/binding and/or identification of agents that inhibit pcdh18/p56$^{lck}$ intracellular interaction/binding presents an opportunity to develop therapeutic agents that have the ability to re-set a patient's immune system to promote strong, effective anti-tumor T cell responses, particularly those of CD8+ TILs.

REFERENCES

1. Pittet, M J, D Valmori, P R Dunbar, D E Speiser, D Lienard, F Lejeune, K Fleischhauer, V Cerundolo, J C Cerottini, and P Romero. (1999). High frequencies of naive Melan-A/MART-1-specific CD8(+) T cells in a large proportion of human histocompatibility leukocyte antigen (HLA)-A2 individuals. J Exp Med 190: 705-715.
2. Romero, P, P R Dunbar, D Valmori, M Pittet, G S Ogg, D Rimoldi, J L Chen, D Lienard, J C Cerottini, and V Cerundolo. (1998). Ex vivo staining of metastatic lymph nodes by class I major histocompatibility complex tetramers reveals high numbers of antigen-experienced tumor-specific cytolytic T lymphocytes. J Exp Med 188: 1641-1650.
3. Zippelius, A, P Batard, V Rubio-Godoy, G Bioley, D Lienard, F Lejeune, D Rimoldi, P Guillaume, N Meidenbauer, A Mackensen, N Rufer, N Lubenow, D Speiser, J C Cerottini, P Romero, and M J Pittet. (2004). Effector function of human tumor-specific CD8 T cells in melanoma lesions: a state of local functional tolerance. Cancer Res 64: 2865-2873.
4. Frey, A B, and N Monu. (2006). Effector-phase tolerance: another mechanism of how cancer escapes antitumor immune response. J Leukoc Biol 79: 652-662.
5. Monu, N, and A B Frey. (2007). Suppression of proximal T cell receptor signaling and lytic function in CD8+ tumor-infiltrating T cells. Cancer Res 67: 11447-11454.
6. Radoja, S, M Saio, and A B Frey. (2001). CD8+ tumor-infiltrating lymphocytes are primed for Fas-mediated activation-induced cell death but are not apoptotic in situ. J Immunol 166: 6074-6083.
7. Koneru, M, D Schaer, N Monu, A Ayala, and A B Frey. (2005). Defective proximal TCR signaling inhibits CD8+ tumor-infiltrating lymphocyte lytic function. J Immunol 174: 1830-1840.
8. Homayouni, R, D S Rice, and T Curran. (2001). Disabled-1 interacts with a novel developmentally regulated protocadherin. Biochem Biophys Res Commun 289: 539-547.
9. Ma, J S, N Monu, D T Shen, I Mecklenbrauker, N Radoja, T F Haydar, M Leitges, A B Frey, S Vukmanovic, and S Radoja. (2007). Protein kinase Cdelta regulates antigen receptor-induced lytic granule polarization in mouse CD8+ CTL. J Immunol 178: 7814-7821.
10. Dong, H, S E Strome, D R Salomao, H Tamura, F Hirano, D B Flies, P C Roche, J Lu, G Zhu, K Tamada, V A Lennon, E Celis, and L Chen. (2002). Tumor-associated B7-H1 promotes T-cell apoptosis: a potential mechanism of immune evasion. Nat Med 8: 793-800.
11. Greenwald, R J, G J Freeman, and A H Sharpe. (2005). The B7 family revisited. Annu Rev Immunol 23: 515-548.
12. Agata, Y, A Kawasaki, H Nishimura, Y Ishida, T Tsubata, H Yagita, and T Honjo. (1996). Expression of the PD-1 antigen on the surface of stimulated mouse T and B lymphocytes. Int Immunol 8: 765-772.
13. Koneru, M, N Monu, D Schaer, J Barletta, and A B Frey. (2006). Defective adhesion in tumor infiltrating CD8+ T cells. J Immunol 176: 6103-6111.
14. Radoja, S, M Saio, D Schaer, M Koneru, S Vukmanovic, and A B Frey. (2001). CD8(+) tumor-infiltrating T cells are deficient in perforin-mediated cytolytic activity due to defective microtubule-organizing center mobilization and lytic granule exocytosis. J Immunol 167: 5042-5051.
15. Sharpe, A H, E J Wherry, R Ahmed, and G J Freeman. (2007). The function of programmed cell death 1 and its ligands in regulating autoimmunity and infection. Nat Immunol 8: 239-245.
16. Vazquez-Cintron, E J, N R Monu, and A B Frey. (2010). Tumor-induced disruption of proximal TCR-mediated signal transduction in tumor-infiltrating CD8+ lymphocytes inactivates antitumor effector phase. J Immunol 185: 7133-7140.
17. Vivier, E, and N Anfossi. (2004). Inhibitory NK-cell receptors on T cells: witness of the past, actors of the future. Nat Rev Immunol 4: 190-198.
18. Blackburn, S D, H Shin, W N Haining, T Zou, C J Workman, A Polley, M R Betts, G J Freeman, D A Vignali, and E J Wherry. (2009). Coregulation of CD8+ T cell exhaustion by multiple inhibitory receptors during chronic viral infection. Nat Immunol 10: 29-37.
19. Wherry, E J, S J Ha, S M Kaech, W N Haining, S Sarkar, V Kalia, S Subramaniam, J N Blattman, D L Barber, and R Ahmed. (2007). Molecular signature of CD8+ T cell exhaustion during chronic viral infection. Immunity 27: 670-684.
20. Barber, D L, E J Wherry, D Masopust, B Zhu, J P Allison, A H Sharpe, G J Freeman, and R Ahmed. (2006). Restoring function in exhausted CD8 T cells during chronic viral infection. Nature 439: 682-687.
21. Aamar, E, and I B Dawid. (2008). Protocadherin-18a has a role in cell adhesion, behavior and migration in zebrafish development. Dev Biol 318: 335-346.
22. Newman, D K, C Hamilton, and P J Newman. (2001). Inhibition of antigen-receptor signaling by Platelet Endothelial Cell Adhesion Molecule-1 (CD31) requires functional ITIMs, SHP-2, and p56(lck). Blood 97: 2351-2357.
23. Penna, G, A Roncari, S Amuchastegui, K C Daniel, E Bern, M Colonna, and L Adorini. (2005). Expression of the inhibitory receptor ILT3 on dendritic cells is dispensable for induction of CD4+Foxp3+ regulatory T cells by 1,25-dihydroxyvitamin D3. Blood 106: 3490-3497.

24. Zou, W, and L Chen. (2008). Inhibitory B7-family molecules in the tumour microenvironment. Nat Rev Immunol 8: 467-477.
25. Sharan, R, A Maron-Katz, and R Shamir. (2003). CLICK and EXPANDER: a system for clustering and visualizing gene expression data. Bioinformatics 19: 1787-1799.
26. Sharan, R, and R Shamir. (2000). CLICK: a clustering algorithm with applications to gene expression analysis. Proc Int Conf Intell Syst Mol Biol 8: 307-316.
27. Shamir, R, A Maron-Katz, A Tanay, C Linhart, I Steinfeld, R Sharan, Y Shiloh, and R Elkon. (2005). EXPANDER—an integrative program suite for microarray data analysis. BMC Bioinformatics 6: 232.
28. Blomgran, R, and J D Ernst. (2011). Lung neutrophils facilitate activation of naive antigen-specific CD4+ T cells during *Mycobacterium tuberculosis* infection. J Immunol 186: 7110-7119.
29. Hosack, D A, G Dennis, Jr., B T Sherman, H C Lane, and R A Lempicki. (2003). Identifying biological themes within lists of genes with EASE. Genome Biol 4: R70.

What is claimed is:

1. A method for screening to identify agents that modulate pcdh18 mediated inhibition of T cell effector function, the method comprising: a) contacting a T cell expressing pcdh18 with a population of pcdh18 molecules in the presence or absence of a candidate modulator agent; and b) determining the ability of the candidate modulator agent to modulate proximal T cell receptor signaling, wherein a change in proximal T cell receptor signaling in the presence of the candidate modulator agent relative to that in the absence of the candidate modulator agent or in the presence of a control agent identifies the candidate modulator agent as a modulator pcdh18 mediated inhibition of T cell effector function.

2. The method of claim 1, wherein modulation of the proximal T cell receptor signaling is determined by measuring ZAP70 phosphorylation.

3. The method of claim 2, wherein the candidate modulator agent inhibits pcdh18 mediated inhibition of T cell effector function and thereby increases ZAP70 phosphorylation.

4. The method of claim 2, wherein the candidate modulator agent enhances pcdh18 mediated inhibition of T cell effector function and thereby decreases ZAP70 phosphorylation.

5. The method of claim 2, wherein the population of pcdh18 molecules is expressed on a cell.

6. The method of claim 5, wherein the cell is a tumor cell that expresses pcdh18.

7. The method of claim 6, wherein the tumor cell is an adenocarcinoma cell, a breast cancer cell, an ovarian cancer cell, a cervical cancer cell, an endometrial cancer cell, a glioma cell, a lymphoma cell, a lung cancer cell, a melanoma cell, a pancreatic cancer cell, and a liver cancer cell.

* * * * *

UNITED STATES PATENT AND TRADEMARK OFFICE
CERTIFICATE OF CORRECTION

PATENT NO. : 9,562,892 B2
APPLICATION NO. : 14/044087
DATED : February 7, 2017
INVENTOR(S) : Alan B. Frey et al.

Page 1 of 1

It is certified that error appears in the above-identified patent and that said Letters Patent is hereby corrected as shown below:

In the Specification

At Column 1, Lines 16-19, replace:
"The research leading to the present invention was supported, at least in part, by National Institutes of Health Grant Nos. R01 CA108573, F31 CA136164, and F31 CA162875. Accordingly, the Government has certain rights in the invention."

With:
--This invention was made with government support under grant numbers R01 CA108573, F31 CA136164, and F31 CA162875 awarded by the National Institutes of Health. The government has certain rights in the invention.--

Signed and Sealed this
Seventh Day of May, 2019

Andrei Iancu
*Director of the United States Patent and Trademark Office*

SEQUENCE LISTING

```
<160> NUMBER OF SEQ ID NOS: 54

<210> SEQ ID NO 1
<211> LENGTH: 8
<212> TYPE: PRT
<213> ORGANISM: Mus musculus

<400> SEQUENCE: 1

Glu Gly Gln Tyr Gln Pro Gln Pro
 1               5

<210> SEQ ID NO 2
<211> LENGTH: 8
<212> TYPE: PRT
<213> ORGANISM: Homo sapiens

<400> SEQUENCE: 2

Gln Gly Gln Tyr Gln Pro Arg Pro
 1               5

<210> SEQ ID NO 3
<211> LENGTH: 8
<212> TYPE: PRT
<213> ORGANISM: Mus musculus

<400> SEQUENCE: 3

Gln Gly Gln Tyr Gln Pro Arg Pro
 1               5

<210> SEQ ID NO 4
<211> LENGTH: 8
<212> TYPE: PRT
<213> ORGANISM: Xenopus laevis

<400> SEQUENCE: 4

Thr Ser Gly Trp His Leu Asp Asn
 1               5

<210> SEQ ID NO 5
<211> LENGTH: 8
<212> TYPE: PRT
<213> ORGANISM: Homo sapiens

<400> SEQUENCE: 5

Leu His Pro Gln Ser Pro Thr Ala
 1               5

<210> SEQ ID NO 6
<211> LENGTH: 8
<212> TYPE: PRT
<213> ORGANISM: Homo sapiens

<400> SEQUENCE: 6
```

```
Tyr Gly Ala Ser Pro Gly Phe Pro
 1               5

<210> SEQ ID NO 7
<211> LENGTH: 8
<212> TYPE: PRT
<213> ORGANISM: Homo sapiens
<220> FEATURE:
<221> NAME/KEY: misc_feature
<222> LOCATION: (2)...(2)
<223> OTHER INFORMATION: Xaa is any amino acid

<400> SEQUENCE: 7

Gln Xaa Arg Asn Ala Ser Arg Glu
 1               5

<210> SEQ ID NO 8
<211> LENGTH: 8
<212> TYPE: PRT
<213> ORGANISM: Homo sapiens

<400> SEQUENCE: 8

Gly Ser Gln Asn Glu Pro Arg Gln
 1               5

<210> SEQ ID NO 9
<211> LENGTH: 5906
<212> TYPE: DNA
<213> ORGANISM: Homo sapiens

<400> SEQUENCE: 9
gcaatcacgg gtgtttagtc tgcagccgag cagctaaagg gagaaagaat cgctcaggaa      60
agacacactg cagactccac cggcaccctg caatagatgg attccgacta cacaagggag     120
aaaacgcgga ggtgacactc tcctgcctgg aaagaggacg aacgaccaaa caaacgcaag     180
gactggactc catgccgaag gtatctggaa gtcgtgacac ggtgtgtata aaacaaaagt     240
ttgcgagctg ttaattgctg tgctgtgtta ttaagagacg ctttcaagtt tcaagtacca     300
aatgtagctt tacgttgcca aaggaagttg aggcaattgc tttgctgttt taacttgctc     360
tgtgagggaa atctcataaa ctgaccaatg caccaaatga atgctaaaat gcactttagg     420 tttgttttg cacttctgat agtatctttc aaccacgatg tactgggcaa gaatttgaaa      480
tacaggattt atgaggaaca gagggttgga tcagtaattg caagactatc agaggatgtg     540
gctgatgttt tattgaagct tcctaatcct tctactgttc gatttcgagc catgcagagg     600
ggaaattctc ctctacttgt agtaaacgag gataatgggg aaatcagcat aggggctaca     660
attgaccgtg aacaactgtg ccagaaaaac ttgaactgtt ccatagagtt tgatgtgatc     720
actctaccca cagagcatct gcagcttttc catattgaag ttgaagtgct ggatattaat     780
gacaattctc cccagttttc aagatctctc atacctattg agatatctga gagtgcagca     840
gttgggactc gcattcccct ggacagtgca tttgatccag atgttgggga aaattccctc     900
cacacatact cgctctctgc caatgatttt tttaatatcg aggttcggac caggactgat     960
ggagccaagt atgcagaact catagtggtc agagagttag atcgggagct gaagtcaagc    1020
tacgagcttc agctcactgc ctcagacatg ggagtacctc agaggtctgg ctcatccata    1080
ctaaaaataa gcatttcaga ctccaatgac aacagccctg cttttgagca gcaatcttat    1140
ataatacaac tcttagaaaa ctccccggtt ggcactttgc tcttagatct gaatgccacg    1200
gatccagatg agggcgctaa tgggaaaatt gtatattcct tcagcagtca tgtgtctccc    1260
```

```
aaaattatgg agactttta aattgattct gaaagaggac atttgactct tttcaagcaa      1320
gtggattatg aaatcaccaa atcctatgag attgatgttc aggctcaaga tttgggtcca      1380
aattcaatcc cagcccattg caaaattata attaaggttg tggatgttaa tgacaataaa      1440
cctgaaatta acatcaacct catgtcccct ggaaaagaag aaatatctta tatttttgaa      1500
ggggatccta ttgatacatt tgttgctttg tcagagttc aggacaagga ttctgggctg       1560
aatggagaaa tagtttgtaa gcttcatgga catggtcact ttaaacttca gaagacatat      1620
gaaaacaatt atttaatctt aactaatgcc acactggata gagaaagag atctgagtat       1680
agtttgactg taatcgctga ggacagggg acacccagtc tctctacagt gaaacatttt       1740
acagttcaaa tcaatgatat caatgacaat ccaccccact tccagagaag ccgatatgaa      1800
tttgtaattt cagaaaataa ctcaccaggg gcatatatca ccactgttac agccacagat      1860
cctgatcttg gagaaaatgg gcaagtgaca tacaccatct tggagagttt tattctagga      1920
agttccataa ctacatatgt aaccattgac ccatctaatg gagccatcta tgccctcaga      1980
atctttgatc atgaagaagt gagtcagatc acttttgtgg tagaagcaag agatggagga      2040
agcccgaagc aactggtaag caataccaca gttgtgctca ccatcattga cgaaaatgac      2100
aacgttcctg tggttatagg gcctgcattg cgtaataata cggcagaaat caccattccc      2160
aaaggggctg aaagtggctt tcatgtcaca agaataaggg caattgacag agactctggt      2220
gtgaatgctg aactcagctg cgccatagta gcaggtaatg aggagaatat cttcataatt      2280
gatccacgat catgtgacat ccataccaac gttagcatgg attctgttcc ctacacagaa      2340
tgggagctgt cagttatcat tcaggacaaa ggcaatcctc agctacatac caaagtcctt      2400
ctgaagtgca tgatctttga atatgcagag tcggtgacaa gtacagcaat gacttcagta      2460
agccaggcat ccttggatgt ctccatgata ataattattt ccttaggagc aatttgtgca      2520
gtgttgctgg ttattatggt gctatttgca actaggtgta accgcgagaa gaaagacact      2580
agatcctata actgcagggt ggccgaatca acttaccagc accacccaaa aaggccatcc      2640
cggcagattc acaaggggga catcacattg gtgcctacca taaatggcac tctgcccatc      2700
agatctcatc acagatcgtc tccatcttca tctcctacct tagaaagagg gcagatgggc      2760
agccggcaga gtcacaacag tcaccagtca ctcaacagtt tggtgacaat ctcatcaaac      2820
cacgtgccag agaattctc attagaactc acccacgcca ctcctgctgt tgagcaggtc      2880
tctcagcttc tttcaatgct tcaccagggg caatatcagc aagaccaag ttttcgagga      2940
aacaaatatt ccaggagcta cagatatgcc cttcaagaca tggacaaatt tagcttgaaa      3000
gacagtggcc gtggtgacag tgaggcagga cagtgatt atgatttggg gcgagattct       3060
ccaatagata ggctgttggg tgaaggattc agcgacctgt ttctcacaga tggaagaatt      3120
ccagcagcta tgagactctg cacggaggag tgcagggtcc tgggacactc tgaccagtgc      3180
tggatgccac cactgccctc accgtcttct gattatagga gtaacatgtt cattccaggg      3240
gaagaattcc caacgcaacc ccagcagcag catccacatc agagtcttga ggatgacgct      3300
cagcctgcag attccggtga aaagaagaag agttttttcca cctttggaaa ggactcccca      3360
aacgatgagg acactgggga taccagcaca tcatctctgc tctcggaaat gagcagtgtg      3420
ttccagcgtc tcttaccgcc ttccctggac acctattctg aatgcagtga ggtggatcgg      3480
tccaactccc tggagcgcag gaagggaccc ttgccagcca aaactgtggg ttacccacag      3540
ggggtagcgg catgggcagc cagtacgcat tttcaaaatc ccaccaccaa ctgtgggccg      3600
```

-continued

```
ccacttggaa ctcactccag tgtgcagcct tcttcaaaat ggctgccagc catggaggag    3660
atccctgaaa attatgagga agatgatttt gacaatgtgc tcaaccacct caatgatggg    3720
aaacacgaac tcatggatgc cagtgaactg gtggcagaga ttaacaaact gcttcaagat    3780
gtccgccaga gctaggagat tttagcgaag cattttttgtt tccatgtata tggaaatagg    3840
gaacaacaac aacaacaaaa aaccctgaaa gaactggcat tgccaaatag ttgcatttat    3900
cataaatgtg tctgtgtata ttgaatatta aatactgtat tttcgtatgt acacaatgca    3960
agtgtgatta ttttaatctg tattttaaaa atacatttgt accttatatt tatgtgtaat    4020
ttaacaaaca aattttatttt ttttactccc atgacagaca tgttttttcct agtcgtgtag    4080
aaactagcca ctgttcaaat ctgatacact attcaaccac aaagtgtaaa ggcactgctt    4140
agattagttt tgttggggaa gaattattat gttgtatgaa caacccccact gaagcattat    4200
acaattctta attccattaa gtgatcccac ttttttttcaa taacttttta gaaattaaga    4260
atcattaaaa ttgttaagct atttttattgt tattttctct actttctact agccccaata    4320
gttgaactct tataggaaaa tcgaaagata aagtgaaagt ttatttcagg actgagaaat    4380
atcttgaagg ttatttatta gatgactatc tcaaatgaac ttttttataga caatgatgaa    4440
aacagaatta aagtcaatgt ttcctgactc ccaggcccct actattccag gccatcacac    4500
tggcctgttc cggagaatat ttctctcaca atattattat ctacttataa ttatggtaaa    4560
caataaattt tattccatcc ttgtagtatg aaacatgctc caaggaaatg gaatctgtcc    4620
tttaaatgga taacagtatg tgttctaatg gcataaaata ttactggata aaaacagttg    4680
tgtcagtgtc tctcctaagg tagtaaatat aattgactta ttctgaaccc attctatttt    4740
gaatctcccc tttcctctca caatacttga acatttttaat cttttggaat attgtctttc    4800
tttgttataa ctattcattt ttagcttttg tctccagtgc atgatctcat atttttgctt    4860
ttattttttag tataagaaca tttataaaat catattttttg ttactgcaat tgtttttattt    4920
gttgtgtggc aaatgagaaa tccttttattt attgtgctgt gatctctctg tgtggaatgc    4980
cttggtgaga gagatgctta ttatgactat tatcatttct gaccaagctt ctattaatgt    5040
tatttctaat aatacactat cttgattgta ctctccagaa aatttttctg tcagtgaaaa    5100
taaaagaaaa attaaagtaa agctaaggaa ctgtctataa gtcagagtcc tgttcctaca    5160
tatttgttca aaagcttggc atgcagcagg cccttcctga gcgggtgatt cagtgttgag    5220
tttcaaataa taaacaggca gcattcagtt ggctgggcga acaagaaaaa cacaatggaa    5280
aaggaatgag tttgagactt gtaatgggaa tgaaagtagt aagccatatt ccagctaaat    5340
aagttaaatg catttgggga ataaagaaaa aagagtaagc aagcaataat tgcttgaata    5400
tttttcaaat tacaacaaaa aaaaatactt tcttaggaca ttttgtatta aattgtgcag    5460
gataaaaagg tatccttaca atgtttccag gaggcaagaa tattatcgtc cctggcttgc    5520
tagtcaggaa ttgaaacact gggaaagtta agtaactgaa aagtgactaa aattcagata    5580
tttgaattct caaatgagta ccacattaaa tagaatatat tacctctttc aacaggcaca    5640
ttttcctttta taggagagat tgcaattaca agtgaaattt cagtatattt ttcagtagat    5700
tacacacaca aacgctaacc atatttaaat gcattctgcc tttcaacttc acttcctttc    5760
agtatatatt accattaaga aaaagacttt tatatcctca ctgttcttaa tttaaagcac    5820
cagcagtaat atgggaagct atgctgaaaa ccgctatttt gaataatgtg aaataaataa    5880
aatgcaatat ttcattcaac acaaaa                                         5906
```

```
<210> SEQ ID NO 10
<211> LENGTH: 1134
<212> TYPE: PRT
<213> ORGANISM: Homo sapiens

<400> SEQUENCE: 10

Met His Gln Met Asn Ala Lys Met His Phe Arg Phe Val Phe Ala Leu
1               5                   10                  15

Leu Ile Val Ser Phe Asn His Asp Val Leu Gly Lys Asn Leu Lys Tyr
            20                  25                  30

Arg Ile Tyr Glu Glu Gln Arg Val Gly Ser Val Ile Ala Arg Leu Ser
        35                  40                  45

Glu Asp Val Ala Asp Val Leu Leu Lys Leu Pro Asn Pro Ser Thr Val
50                  55                  60

Arg Phe Arg Ala Met Gln Arg Gly Asn Ser Pro Leu Leu Val Val Asn
65                  70                  75                  80

Glu Asp Asn Gly Glu Ile Ser Ile Gly Ala Thr Ile Asp Arg Glu Gln
                85                  90                  95

Leu Cys Gln Lys Asn Leu Asn Cys Ser Ile Glu Phe Asp Val Ile Thr
            100                 105                 110

Leu Pro Thr Glu His Leu Gln Leu Phe His Ile Glu Val Glu Val Leu
        115                 120                 125

Asp Ile Asn Asp Asn Ser Pro Gln Phe Ser Arg Ser Leu Ile Pro Ile
130                 135                 140

Glu Ile Ser Glu Ser Ala Ala Val Gly Thr Arg Ile Pro Leu Asp Ser
145                 150                 155                 160

Ala Phe Asp Pro Asp Val Gly Glu Asn Ser Leu His Thr Tyr Ser Leu
                165                 170                 175

Ser Ala Asn Asp Phe Phe Asn Ile Glu Val Arg Thr Arg Thr Asp Gly
            180                 185                 190

Ala Lys Tyr Ala Glu Leu Ile Val Val Arg Glu Leu Asp Arg Glu Leu
        195                 200                 205

Lys Ser Ser Tyr Glu Leu Gln Leu Thr Ala Ser Asp Met Gly Val Pro
210                 215                 220

Gln Arg Ser Gly Ser Ser Ile Leu Lys Ile Ser Ile Ser Asp Ser Asn
225                 230                 235                 240

Asp Asn Ser Pro Ala Phe Glu Gln Gln Ser Tyr Ile Ile Gln Leu Leu
                245                 250                 255

Glu Asn Ser Pro Val Gly Thr Leu Leu Leu Asp Leu Asn Ala Thr Asp
            260                 265                 270

Pro Asp Glu Gly Ala Asn Gly Lys Ile Val Tyr Ser Phe Ser Ser His
        275                 280                 285

Val Ser Pro Lys Ile Met Glu Thr Phe Lys Ile Asp Ser Glu Arg Gly
290                 295                 300

His Leu Thr Leu Phe Lys Gln Val Asp Tyr Glu Ile Thr Lys Ser Tyr
305                 310                 315                 320

Glu Ile Asp Val Gln Ala Gln Asp Leu Gly Pro Asn Ser Ile Pro Ala
                325                 330                 335

His Cys Lys Ile Ile Ile Lys Val Val Asp Val Asn Asp Asn Lys Pro
            340                 345                 350

Glu Ile Asn Ile Asn Leu Met Ser Pro Gly Lys Glu Glu Ile Ser Tyr
        355                 360                 365

Ile Phe Glu Gly Asp Pro Ile Asp Thr Phe Val Ala Leu Val Arg Val
370                 375                 380
```

```
Gln Asp Lys Asp Ser Gly Leu Asn Gly Glu Ile Val Cys Lys Leu His
385                 390                 395                 400

Gly His Gly His Phe Lys Leu Gln Lys Thr Tyr Glu Asn Asn Tyr Leu
            405                 410                 415

Ile Leu Thr Asn Ala Thr Leu Asp Arg Glu Lys Arg Ser Glu Tyr Ser
        420                 425                 430

Leu Thr Val Ile Ala Glu Asp Arg Gly Thr Pro Ser Leu Ser Thr Val
    435                 440                 445

Lys His Phe Thr Val Gln Ile Asn Asp Ile Asn Asp Asn Pro Pro His
450                 455                 460

Phe Gln Arg Ser Arg Tyr Glu Phe Val Ile Ser Glu Asn Asn Ser Pro
465                 470                 475                 480

Gly Ala Tyr Ile Thr Thr Val Thr Ala Thr Asp Pro Asp Leu Gly Glu
            485                 490                 495

Asn Gly Gln Val Thr Tyr Thr Ile Leu Glu Ser Phe Ile Leu Gly Ser
        500                 505                 510

Ser Ile Thr Thr Tyr Val Thr Ile Asp Pro Ser Asn Gly Ala Ile Tyr
    515                 520                 525

Ala Leu Arg Ile Phe Asp His Glu Val Ser Gln Ile Thr Phe Val
530                 535                 540

Val Glu Ala Arg Asp Gly Gly Ser Pro Lys Gln Leu Val Ser Asn Thr
545                 550                 555                 560

Thr Val Val Leu Thr Ile Ile Asp Glu Asn Asp Asn Val Pro Val Val
            565                 570                 575

Ile Gly Pro Ala Leu Arg Asn Asn Thr Ala Glu Ile Thr Ile Pro Lys
        580                 585                 590

Gly Ala Glu Ser Gly Phe His Val Thr Arg Ile Arg Ala Ile Asp Arg
    595                 600                 605

Asp Ser Gly Val Asn Ala Glu Leu Ser Cys Ala Ile Val Ala Gly Asn
610                 615                 620

Glu Glu Asn Ile Phe Ile Ile Asp Pro Arg Ser Cys Asp Ile His Thr
625                 630                 635                 640

Asn Val Ser Met Asp Ser Val Pro Tyr Thr Glu Trp Glu Leu Ser Val
            645                 650                 655

Ile Ile Gln Asp Lys Gly Asn Pro Gln Leu His Thr Lys Val Leu Leu
        660                 665                 670

Lys Cys Met Ile Phe Glu Tyr Ala Glu Ser Val Thr Ser Thr Ala Met
    675                 680                 685

Thr Ser Val Ser Gln Ala Ser Leu Asp Val Ser Met Ile Ile Ile Ile
690                 695                 700

Ser Leu Gly Ala Ile Cys Ala Val Leu Leu Val Ile Met Val Leu Phe
705                 710                 715                 720

Ala Thr Arg Cys Asn Arg Glu Lys Lys Asp Thr Arg Ser Tyr Asn Cys
            725                 730                 735

Arg Val Ala Glu Ser Thr Tyr Gln His His Pro Lys Arg Pro Ser Arg
        740                 745                 750

Gln Ile His Lys Gly Asp Ile Thr Leu Val Pro Thr Ile Asn Gly Thr
    755                 760                 765

Leu Pro Ile Arg Ser His His Arg Ser Ser Pro Ser Ser Pro Thr
770                 775                 780

Leu Glu Arg Gly Gln Met Gly Ser Arg Gln Ser His Asn Ser His Gln
785                 790                 795                 800

Ser Leu Asn Ser Leu Val Thr Ile Ser Ser Asn His Val Pro Glu Asn
```

805                 810                 815
Phe Ser Leu Glu Leu Thr His Ala Thr Pro Ala Val Glu Val Ser Gln
                820                 825                 830

Leu Leu Ser Met Leu His Gln Gly Gln Tyr Gln Pro Arg Pro Ser Phe
            835                 840                 845

Arg Gly Asn Lys Tyr Ser Arg Ser Tyr Arg Tyr Ala Leu Gln Asp Met
        850                 855                 860

Asp Lys Phe Ser Leu Lys Asp Ser Gly Arg Gly Asp Ser Glu Ala Gly
865                 870                 875                 880

Asp Ser Asp Tyr Asp Leu Gly Arg Asp Ser Pro Ile Asp Arg Leu Leu
                885                 890                 895

Gly Glu Gly Phe Ser Asp Leu Phe Leu Thr Asp Gly Arg Ile Pro Ala
            900                 905                 910

Ala Met Arg Leu Cys Thr Glu Glu Cys Arg Val Leu Gly His Ser Asp
        915                 920                 925

Gln Cys Trp Met Pro Pro Leu Pro Ser Pro Ser Ser Asp Tyr Arg Ser
930                 935                 940

Asn Met Phe Ile Pro Gly Glu Glu Phe Pro Thr Gln Pro Gln Gln Gln
945                 950                 955                 960

His Pro His Gln Ser Leu Glu Asp Asp Ala Gln Pro Ala Asp Ser Gly
                965                 970                 975

Glu Lys Lys Lys Ser Phe Ser Thr Phe Gly Lys Asp Ser Pro Asn Asp
            980                 985                 990

Glu Asp Thr Gly Asp Thr Ser Thr Ser Ser Leu Leu Ser Glu Met Ser
        995                 1000                1005

Ser Val Phe Gln Arg Leu Leu Pro Pro Ser Leu Asp Thr Tyr Ser Glu
    1010                1015                1020

Cys Ser Glu Val Asp Arg Ser Asn Ser Leu Glu Arg Arg Lys Gly Pro
1025                1030                1035                1040

Leu Pro Ala Lys Thr Val Gly Tyr Pro Gln Gly Val Ala Ala Trp Ala
                1045                1050                1055

Ala Ser Thr His Phe Gln Asn Pro Thr Thr Asn Cys Gly Pro Pro Leu
            1060                1065                1070

Gly Thr His Ser Ser Val Gln Pro Ser Ser Lys Trp Leu Pro Ala Met
        1075                1080                1085

Glu Glu Ile Pro Glu Asn Tyr Glu Glu Asp Phe Asp Asn Val Leu
    1090                1095                1100

Asn His Leu Asn Asp Gly Lys His Glu Leu Met Asp Ala Ser Glu Leu
1105                1110                1115                1120

Val Ala Glu Ile Asn Lys Leu Leu Gln Asp Val Arg Gln Ser
                1125                1130

<210> SEQ ID NO 11
<211> LENGTH: 306
<212> TYPE: DNA
<213> ORGANISM: Homo sapiens

<400> SEQUENCE: 11
tacaggattt atgaggaaca gagggttgga tcagtaattg caagactatc agaggatgtg    60
gctgatgttt tattgaagct tcctaatcct tctactgttc gatttcgagc catgcagagg   120
ggaaattctc ctctacttgt agtaaacgag gataatgggg aaatcagcat aggggctaca   180
attgaccgtg aacaactgtg ccagaaaaac ttgaactgtt ccatagagtt tgatgtgatc   240
actctaccca cagagcatct gcagcttttc catattgaag ttgaagtgct ggatattaat   300
gacaat                                                                306

<210> SEQ ID NO 12
<211> LENGTH: 102
<212> TYPE: PRT
<213> ORGANISM: Homo sapiens

<400> SEQUENCE: 12

Tyr Arg Ile Tyr Glu Glu Gln Arg Val Gly Ser Val Ile Ala Arg Leu
1               5                   10                  15

Ser Glu Asp Val Ala Asp Val Leu Leu Lys Leu Pro Asn Pro Ser Thr
            20                  25                  30

Val Arg Phe Arg Ala Met Gln Arg Gly Asn Ser Pro Leu Leu Val Val
        35                  40                  45

Asn Glu Asp Asn Gly Glu Ile Ser Ile Gly Ala Thr Ile Asp Arg Glu
    50                  55                  60

Gln Leu Cys Gln Lys Asn Leu Asn Cys Ser Ile Glu Phe Asp Val Ile
65                  70                  75                  80

Thr Leu Pro Thr Glu His Leu Gln Leu Phe His Ile Glu Val Glu Val
                85                  90                  95

Leu Asp Ile Asn Asp Asn
            100

<210> SEQ ID NO 13
<211> LENGTH: 309
<212> TYPE: DNA
<213> ORGANISM: Homo sapiens

<400> SEQUENCE: 13
tatgaatttg taatttcaga aaataactca ccaggggcat atatcaccac tgttacagcc      60
acagatcctg atcttggaga aaatgggcaa gtgacataca ccatcttgga gagttttatt    120
ctaggaagtt ccataactac atatgtaacc attgacccat ctaatggagc catctatgcc    180
ctcagaatct ttgatcatga agaagtgagt cagatcactt ttgtggtaga agcaagagat    240
ggaggaagcc cgaagcaact ggtaagcaat accacagttg tgctcaccat cattgacgaa    300
aatgacaac                                                            309

<210> SEQ ID NO 14
<211> LENGTH: 103
<212> TYPE: PRT
<213> ORGANISM: Homo sapiens

<400> SEQUENCE: 14

Tyr Glu Phe Val Ile Ser Glu Asn Asn Ser Pro Gly Ala Tyr Ile Thr
1               5                   10                  15

Thr Val Thr Ala Thr Asp Pro Asp Leu Gly Glu Asn Gly Gln Val Thr
            20                  25                  30

Tyr Thr Ile Leu Glu Ser Phe Ile Leu Gly Ser Ser Ile Thr Thr Tyr
        35                  40                  45

Val Thr Ile Asp Pro Ser Asn Gly Ala Ile Tyr Ala Leu Arg Ile Phe
    50                  55                  60

Asp His Glu Glu Val Ser Gln Ile Thr Phe Val Val Glu Ala Arg Asp
65                  70                  75                  80

Gly Gly Ser Pro Lys Gln Leu Val Ser Asn Thr Thr Val Val Leu Thr
                85                  90                  95

Ile Ile Asp Glu Asn Asp Asn

<210> SEQ ID NO 15
<211> LENGTH: 1753
<212> TYPE: DNA
<213> ORGANISM: Homo sapiens

<400> SEQUENCE: 15

```
taacttgctc tgtgagggaa atctcataaa ctgaccaatg caccaaatga atgctaaaat      60
gcactttagg tttgtttttg cacttctgat agtatcttte aaccacgatg tactgggcaa     120
gaatttgaaa tacaggattt atgaggaaca gagggttgga tcagtaattg caagactatc     180
agaggatgtg gctgatgttt tattgaagct tcctaatcct tctactgttc gatttcgagc     240
catgcagagg ggaaattctc ctctacttgt agtaaacgag ataatgggg aaatcagcat      300
aggggctaca attgaccgtg aacaactgtg ccagaaaaac ttgaactgtt ccatagagtt     360
tgatgtgatc actctaccca cagagcatct gcagcttttc catattgaag ttgaagtgct     420
ggatattaat gacaattctc cccagttttc aagatctctc atacctattg agatatctga     480
gagtgcagca gttgggactc gcattcccct ggacagtgca tttgatccag atgttgggga     540
aaattccctc cacacatact cgctctctgc caatgatttt tttaatatcg aggttcggac     600
caggactgat ggagccaagt atgcagaact catagtggtc agagagttag atcgggagct     660
gaagtcaagc tacgagcttc agctcactgc ctcagacatg ggagtacctc agaggtctgg     720
ctcatccata ctaaaaataa gcatttcaga ctccaatgac aacagccctg cttttgagca     780
gcaatcttat ataatacaac tcttagaaaa ctccccggtt ggcactttgc tcttagatct     840
gaatgccacg gatccagatg agggcgctaa tgggaaaatt gtatattcct tcagcagtca     900
tgtgtctccc aaaattatgg agactttaa aattgattct gaaagaggac atttgactct     960
tttcaagcaa gtggattatg aaatcaccaa atcctatgag attgatgttc aggctcaaga    1020
tttgggtcca aattcaatcc cagcccattg caaaattata attaaggttg tggatgttaa    1080
tgacaataaa cctgaaatta acatcaacct catgtcccct ggaaaagaag aaatatctta    1140
tatttttgaa ggggatccta ttgatacatt tgttgctttg gtcagagttc aggacaagga    1200
ttctgggctg aatggagaaa tagttttgta agcttcatgga catggtcact ttaaacttca    1260
gaagacatat gaaaacaatt atttaatctt aactaatgcc acactggata gagaaaagag    1320
atctgagtat agtttgactg taatcgctga ggacaggggg acacccagtc tctctacagt    1380
gaaacatttt acagttcaaa tcaatgatat caatgacaat ccaccccact tccagagaag    1440
ccgatatgaa tttgtaattt cagaaaataa ctcaccaggg gcatatatca ccactgttac    1500
agccacagat cctgatcttg gagaaaatgg gcaagtgaca tacaccatct tggagagttt    1560
tattctagga agttccataa ctacatatgt aaccattgac ccatctaatg gagccatcta    1620
tgccctcaga atctttgatc atgaagaagt gagtcagatc acttttgtgg tagaagcaag    1680
agatggagga agcccgaagc aactggtaag caataccaca gttgtgctca ccatcattga    1740
cgaaaatgac aac                                                      1753
```

<210> SEQ ID NO 16
<211> LENGTH: 697
<212> TYPE: PRT
<213> ORGANISM: Homo sapiens

<400> SEQUENCE: 16

Met His Gln Met Asn Ala Lys Met His Phe Arg Phe Val Phe Ala Leu

```
             1               5              10              15
           Leu Ile Val Ser Phe Asn His Asp Val Leu Gly Lys Asn Leu Lys Tyr
                            20                  25                  30
           Arg Ile Tyr Glu Glu Gln Arg Val Gly Ser Val Ile Ala Arg Leu Ser
                            35                  40                  45
           Glu Asp Val Ala Asp Val Leu Leu Lys Leu Pro Asn Pro Ser Thr Val
                50                  55                  60
           Arg Phe Arg Ala Met Gln Arg Gly Asn Ser Pro Leu Leu Val Val Asn
           65                  70                  75                  80
           Glu Asp Asn Gly Glu Ile Ser Ile Gly Ala Thr Ile Asp Arg Glu Gln
                                85                  90                  95
           Leu Cys Gln Lys Asn Leu Asn Cys Ser Ile Glu Phe Asp Val Ile Thr
                           100                 105                 110
           Leu Pro Thr Glu His Leu Gln Leu Phe His Ile Glu Val Glu Val Leu
                           115                 120                 125
           Asp Ile Asn Asp Asn Ser Pro Gln Phe Ser Arg Ser Leu Ile Pro Ile
                130                 135                 140
           Glu Ile Ser Glu Ser Ala Ala Val Gly Thr Arg Ile Pro Leu Asp Ser
           145                 150                 155                 160
           Ala Phe Asp Pro Asp Val Gly Glu Asn Ser Leu His Thr Tyr Ser Leu
                               165                 170                 175
           Ser Ala Asn Asp Phe Phe Asn Ile Glu Val Arg Thr Arg Thr Asp Gly
                           180                 185                 190
           Ala Lys Tyr Ala Glu Leu Ile Val Val Arg Glu Leu Asp Arg Glu Leu
                           195                 200                 205
           Lys Ser Ser Tyr Glu Leu Gln Leu Thr Ala Ser Asp Met Gly Val Pro
                210                 215                 220
           Gln Arg Ser Gly Ser Ser Ile Leu Lys Ile Ser Ile Ser Asp Ser Asn
           225                 230                 235                 240
           Asp Asn Ser Pro Ala Phe Glu Gln Gln Ser Tyr Ile Ile Gln Leu Leu
                               245                 250                 255
           Glu Asn Ser Pro Val Gly Thr Leu Leu Leu Asp Leu Asn Ala Thr Asp
                           260                 265                 270
           Pro Asp Glu Gly Ala Asn Gly Lys Ile Val Tyr Ser Phe Ser Ser His
                           275                 280                 285
           Val Ser Pro Lys Ile Met Glu Thr Phe Lys Ile Asp Ser Glu Arg Gly
                290                 295                 300
           His Leu Thr Leu Phe Lys Gln Val Asp Tyr Glu Ile Thr Lys Ser Tyr
           305                 310                 315                 320
           Glu Ile Asp Val Gln Ala Gln Asp Leu Gly Pro Asn Ser Ile Pro Ala
                               325                 330                 335
           His Cys Lys Ile Ile Ile Lys Val Val Asp Val Asn Asp Asn Lys Pro
                           340                 345                 350
           Glu Ile Asn Ile Asn Leu Met Ser Pro Gly Lys Glu Glu Ile Ser Tyr
                           355                 360                 365
           Ile Phe Glu Gly Asp Pro Ile Asp Thr Phe Val Ala Leu Val Arg Val
                370                 375                 380
           Gln Asp Lys Asp Ser Gly Leu Asn Gly Glu Ile Val Cys Lys Leu His
           385                 390                 395                 400
           Gly His Gly His Phe Lys Leu Gln Lys Thr Tyr Glu Asn Asn Tyr Leu
                               405                 410                 415
           Ile Leu Thr Asn Ala Thr Leu Asp Arg Glu Lys Arg Ser Glu Tyr Ser
                           420                 425                 430
```

Leu Thr Val Ile Ala Glu Asp Arg Gly Thr Pro Ser Leu Ser Thr Val
        435                 440                 445

Lys His Phe Thr Val Gln Ile Asn Asp Ile Asn Asp Asn Pro Pro His
    450                 455                 460

Phe Gln Arg Ser Arg Tyr Glu Phe Val Ile Ser Glu Asn Asn Ser Pro
465                 470                 475                 480

Gly Ala Tyr Ile Thr Thr Val Thr Ala Thr Asp Pro Asp Leu Gly Glu
                485                 490                 495

Asn Gly Gln Val Thr Tyr Thr Ile Leu Glu Ser Phe Ile Leu Gly Ser
            500                 505                 510

Ser Ile Thr Thr Tyr Val Thr Ile Asp Pro Ser Asn Gly Ala Ile Tyr
        515                 520                 525

Ala Leu Arg Ile Phe Asp His Glu Val Ser Gln Ile Thr Phe Val
    530                 535                 540

Val Glu Ala Arg Asp Gly Gly Ser Pro Lys Gln Leu Val Ser Asn Thr
545                 550                 555                 560

Thr Val Val Leu Thr Ile Ile Asp Glu Asn Asp Asn Val Pro Val Val
                565                 570                 575

Ile Gly Pro Ala Leu Arg Asn Asn Thr Ala Glu Ile Thr Ile Pro Lys
            580                 585                 590

Gly Ala Glu Ser Gly Phe His Val Thr Arg Ile Arg Ala Ile Asp Arg
        595                 600                 605

Asp Ser Gly Val Asn Ala Glu Leu Ser Cys Ala Ile Val Ala Gly Asn
    610                 615                 620

Glu Glu Asn Ile Phe Ile Ile Asp Pro Arg Ser Cys Asp Ile His Thr
625                 630                 635                 640

Asn Val Ser Met Asp Ser Val Pro Tyr Thr Glu Trp Glu Leu Ser Val
                645                 650                 655

Ile Ile Gln Asp Lys Gly Asn Pro Gln Leu His Thr Lys Val Leu Leu
            660                 665                 670

Lys Cys Met Ile Phe Glu Tyr Ala Glu Ser Val Thr Ser Thr Ala Met
        675                 680                 685

Thr Ser Val Ser Gln Ala Ser Leu Asp
    690                 695

<210> SEQ ID NO 17
<211> LENGTH: 3405
<212> TYPE: DNA
<213> ORGANISM: Mus musculus

<400> SEQUENCE: 17
atgcaccaaa tgaatactaa atgcactttt agatttgcac ttgcacttct gatggcgttt      60
ttcagccacg atgtcctggc taagaatctg aaatacagga tttatgagga gcagagggtc     120
ggatcggtaa ttgctagact atcagaagat gtggctgatg tttattgaa gctaccaaat      180 ccttctgctg ttcgttttcg agccatgcca cgggggaatt ctcctctcct ggtcgtaaat     240
gagaataccg agaaatcag catagggct aaaattgacc gcgagcaact atgccaaaaa       300
aacttgaact gttcgataga gtttgatgtg ctcactctgc cgaccgagca tctgcagctg     360
ttccacattg aagtggacgt gctggacatt aatgacaatt ccccccaatt ctcgagaccc     420
gtcattccca ttgagatatc ggagagcgca gcagttggga ctcgtatccc cctggacagt    480
gcgttcgacc cagatgttgg ggaaaattcc ctccacacct actcgctctc tgctaatgat     540
tattttaata tcgaagtgcg aaccaggaca gacggggcca agtacgctga actcatagtg    600

```
gtgaaagagt tggatcggga gctgaaggct agctacgagc ttcagctcac cgcctccgac    660
atgggagtgc ctcagaggtc tggctcctcc atcctgaaaa tcagcatttc ggattccaac    720
gacaacagcc cggcctttga gcagccttct tacacaatac aactcttaga aaactcccca    780
gttggaacct tgctccttga tctaaatgcc accgatccag atgagggcgc taatgggaga    840
attgtgtatt ctttcagcag tcatgtgtct cccaaaatta tagagacttt taagatcgac    900
tcagaaaaag gccacttgac tcttttcaag ccagtggatt atgaaatcac caagtcctat    960
gagatagacg ttcaagccca agatttgggt cccaattcca ttcctgctca ttgcaaaatt   1020
ataattaagg ttgtggatgt caatgacaat aaacctgaaa ttagcataaa tctcatgtcc   1080
cctggaaaag aagaagtatc ttatgtcttt aaggggatcc ccattgatac attcgttgct   1140
atcgtcaggt tcaagacaa ggattctggg ctgaatgggg aaataatctg taagcttcat   1200
gggcatggac attttaaact tcagaagaca tatgaaaata actacttgat cttgaccaat   1260
gccactctgg atagaaaaa gagatctgag tatagtttga ctgtgattgc tgaggacaag   1320
ggaacaccaa gcctctcctc agtgagacat tttactgttc aaatcaatga cataaatgac   1380
aatccacctc gcttccagag gagccgatat gaatttgtca tctcagagaa taattcacca   1440
ggggcgtata tcaccacagt tacagccact gatccagatc ttggtgaaaa cggacatgtg   1500
acatacacca ttttggagag ttttgtcttg gaagttcca tcaccacgta tgtaaccatt   1560
gacccctcta atggcgccat ctatgccctc aggatctttg atcatgaaga agtgagtcag   1620
atcacttttg tggtggaagc cagggatgga gggagtcaga agcaactctc cagcaacacc   1680
accgttgtgc tgaccatcat tgatgagaat gacaatgtcc ctgtggttat agggcctgca   1740
atgcacaata atactgcaga aatatccatc cccaaaggag ctgaaagtgg ttttcatgtc   1800
acaagaataa gggtggtcga cagggactct ggtgccaatg ctgaattcag ctgctccata   1860
gtatctggta atgaggaaaa catctttatc atggaccta ggtcatgtga cattcatacc   1920
aacgtcagca tggaatccat tccctctgcg gaatgggcac tctcagttat catccaggac   1980
aagggcagtc ctcctctgca caccaaagtc cttctgaggt gcatggtctt tgactatgca   2040
gaatctgtga caagcacagc catgacctct gtcagccgcg catccttgga tgtgtccatg   2100
atcataatta tttccttggg agcaatttgt gctgtgttgc tggttattat ggtcctgttt   2160
gcaacgaggt gtaatagaga aaagaaagac accagatcct acaactgcag ggtggcagaa   2220
tccacgtacc agcatcatcc taaaaggcca tccaggcaga ttcacaaagg agacatcaca   2280
ctggtaccca ccatcaatgg cactctgccc atcagatctc accacagatc ctccccatct   2340
tcatccccaa ccttggagag gggacaaatg ggcagccgcc agagtcacaa cagtcaccag   2400
tcactcaaca gtttggtgac catctcatca aaccacgtgc cagagaattt ttcattagaa   2460
ctcacccacg ccactcctgc tgttgaggtc tcgcagcttc tctccatgct tcaccagggg   2520
caatatcagc cacggccaag ttttcgagga aacaaatatt ccaggagcta tagatatgcc   2580
cttcaagaca tggataaatt tagcctgaaa gacagtggcc gtggagatag cgaagcagga   2640
gatagcgatt atgatttggg gcgcgattct ccgatagaca ggctcctggg agaaggattc   2700
agtgacctct tcctcacgga cgggagaatt ccagcagcaa tgaggctatg tacggaggag   2760
tgcagagtcc tgggccactc tgaccagtgc tggatgcccc cgctgccctc gccatcctct   2820
gactacagaa gcaacatgtt catccccgga gaagaattcc cagctcaacc tcagcaacag   2880
cattctcatc agggccttga tgatgacagc cagcctgcag aaaacgggga gaaaaaaag   2940
```

-continued

| | |
|---|---|
| agcttctcca ctttgggaa ggactcccct agcgacgagg attcgggaga ctctagcaca | 3000 |
| tcatctctgc tatcagaaat gagcagtgtg ttccagcgcc ttctcccgc atccctagat | 3060 |
| acctttctg aatgcaacga aggggatcgc tccaactctc tggaacgtcg aaagggtccg | 3120 |
| gcacagggca aaactggggg ttacccacaa ggggttgcgg cctgggcagc cagcacacat | 3180 |
| tttcagaacc ccaccagcag ctctgggacc cctctgggga ctcactctag tgtgcagcct | 3240 |
| tcctccaagt ggctgccagc tatggaggag attcctgaaa attacgagga agatgatttt | 3300 |
| gacaatgtgc ttaaccatct cagcgatggg aaacacgaac tcatggatgc cagcgagctg | 3360 |
| gtggctgaga tcaacaaact gcttcaagac gtccgccaga gctag | 3405 |

<210> SEQ ID NO 18
<211> LENGTH: 1134
<212> TYPE: PRT
<213> ORGANISM: Mus musculus

<400> SEQUENCE: 18

Met His Gln Met Asn Thr Lys Met His Phe Arg Phe Ala Leu Ala Leu
1               5                   10                  15

Leu Met Ala Phe Phe Ser His Asp Val Leu Ala Lys Asn Leu Lys Tyr
            20                  25                  30

Arg Ile Tyr Glu Glu Gln Arg Val Gly Ser Val Ile Ala Arg Leu Ser
        35                  40                  45

Glu Asp Val Ala Asp Val Leu Leu Lys Leu Pro Asn Pro Ser Ala Val
    50                  55                  60

Arg Phe Arg Ala Met Pro Arg Gly Asn Ser Pro Leu Leu Val Val Asn
65                  70                  75                  80

Glu Asn Thr Gly Glu Ile Ser Ile Gly Ala Lys Ile Asp Arg Glu Gln
                85                  90                  95

Leu Cys Gln Lys Asn Leu Asn Cys Ser Ile Glu Phe Asp Val Leu Thr
            100                 105                 110

Leu Pro Thr Glu His Leu Gln Leu Phe His Ile Glu Val Asp Val Leu
        115                 120                 125

Asp Ile Asn Asp Asn Ser Pro Gln Phe Ser Arg Pro Val Ile Pro Ile
    130                 135                 140

Glu Ile Ser Glu Ser Ala Ala Val Gly Thr Arg Ile Pro Leu Asp Ser
145                 150                 155                 160

Ala Phe Asp Pro Asp Val Gly Glu Asn Ser Leu His Thr Tyr Ser Leu
                165                 170                 175

Ser Ala Asn Asp Tyr Phe Asn Ile Glu Val Arg Thr Arg Thr Asp Gly
            180                 185                 190

Ala Lys Tyr Ala Glu Leu Ile Val Val Lys Glu Leu Asp Arg Glu Leu
        195                 200                 205

Lys Ala Ser Tyr Glu Leu Gln Leu Thr Ala Ser Asp Met Gly Val Pro
    210                 215                 220

Gln Arg Ser Gly Ser Ser Ile Leu Lys Ile Ser Ile Ser Asp Ser Asn
225                 230                 235                 240

Asp Asn Ser Pro Ala Phe Glu Gln Pro Ser Tyr Thr Ile Gln Leu Leu
                245                 250                 255

Glu Asn Ser Pro Val Gly Thr Leu Leu Leu Asp Leu Asn Ala Thr Asp
            260                 265                 270

Pro Asp Glu Gly Ala Asn Gly Arg Ile Val Tyr Ser Phe Ser Ser His
        275                 280                 285

Val Ser Pro Lys Ile Ile Glu Thr Phe Lys Ile Asp Ser Glu Lys Gly

```
            290                 295                 300
His Leu Thr Leu Phe Lys Pro Val Asp Tyr Glu Ile Thr Lys Ser Tyr
305                 310                 315                 320

Glu Ile Asp Val Gln Ala Gln Asp Leu Gly Pro Asn Ser Ile Pro Ala
                    325                 330                 335

His Cys Lys Ile Ile Lys Val Val Asp Val Asn Asp Asn Lys Pro
                    340                 345                 350

Glu Ile Ser Ile Asn Leu Met Ser Pro Gly Lys Glu Val Ser Tyr
                355                 360                 365

Val Phe Glu Gly Asp Pro Ile Asp Thr Phe Val Ala Ile Val Arg Val
370                 375                 380

Gln Asp Lys Asp Ser Gly Leu Asn Gly Glu Ile Ile Cys Lys Leu His
385                 390                 395                 400

Gly His Gly His Phe Lys Leu Gln Lys Thr Tyr Glu Asn Asn Tyr Leu
                    405                 410                 415

Ile Leu Thr Asn Ala Thr Leu Asp Arg Glu Lys Arg Ser Glu Tyr Ser
                420                 425                 430

Leu Thr Val Ile Ala Glu Asp Lys Gly Thr Pro Ser Leu Ser Ser Val
                    435                 440                 445

Arg His Phe Thr Val Gln Ile Asn Asp Ile Asn Asp Asn Pro Pro Arg
450                 455                 460

Phe Gln Arg Ser Arg Tyr Glu Phe Val Ile Ser Glu Asn Asn Ser Pro
465                 470                 475                 480

Gly Ala Tyr Ile Thr Thr Val Thr Ala Thr Asp Pro Asp Leu Gly Glu
                    485                 490                 495

Asn Gly His Val Thr Tyr Thr Ile Leu Glu Ser Phe Val Leu Gly Ser
                500                 505                 510

Ser Ile Thr Thr Tyr Val Thr Ile Asp Pro Ser Asn Gly Ala Ile Tyr
                515                 520                 525

Ala Leu Arg Ile Phe Asp His Glu Glu Val Ser Gln Ile Thr Phe Val
530                 535                 540

Val Glu Ala Arg Asp Gly Gly Ser Gln Lys Gln Leu Ser Ser Asn Thr
545                 550                 555                 560

Thr Val Val Leu Thr Ile Ile Asp Glu Asn Asp Asn Val Pro Val Val
                    565                 570                 575

Ile Gly Pro Ala Met His Asn Asn Thr Ala Glu Ile Ser Ile Pro Lys
                580                 585                 590

Gly Ala Glu Ser Gly Phe His Val Thr Arg Ile Arg Val Val Asp Arg
                595                 600                 605

Asp Ser Gly Ala Asn Ala Glu Phe Ser Cys Ser Ile Val Ser Gly Asn
                610                 615                 620

Glu Glu Asn Ile Phe Ile Met Asp Pro Arg Ser Cys Asp Ile His Thr
625                 630                 635                 640

Asn Val Ser Met Glu Ser Ile Pro Ser Ala Glu Trp Ala Leu Ser Val
                645                 650                 655

Ile Ile Gln Asp Lys Gly Ser Pro Pro Leu His Thr Lys Val Leu Leu
                660                 665                 670

Arg Cys Met Val Phe Asp Tyr Ala Glu Ser Val Thr Ser Thr Ala Met
                675                 680                 685

Thr Ser Val Ser Arg Ala Ser Leu Asp Val Ser Met Ile Ile Ile Ile
                690                 695                 700

Ser Leu Gly Ala Ile Cys Ala Val Leu Leu Val Ile Met Val Leu Phe
705                 710                 715                 720
```

```
Ala Thr Arg Cys Asn Arg Glu Lys Lys Asp Thr Arg Ser Tyr Asn Cys
                725                 730                 735

Arg Val Ala Glu Ser Thr Tyr Gln His His Pro Lys Arg Pro Ser Arg
            740                 745                 750

Gln Ile His Lys Gly Asp Ile Thr Leu Val Pro Thr Ile Asn Gly Thr
        755                 760                 765

Leu Pro Ile Arg Ser His His Arg Ser Ser Pro Ser Ser Ser Pro Thr
770                 775                 780

Leu Glu Arg Gly Gln Met Gly Ser Arg Gln Ser His Asn Ser His Gln
785                 790                 795                 800

Ser Leu Asn Ser Leu Val Thr Ile Ser Ser Asn His Val Pro Glu Asn
                805                 810                 815

Phe Ser Leu Glu Leu Thr His Ala Thr Pro Ala Val Glu Val Ser Gln
            820                 825                 830

Leu Leu Ser Met Leu His Gln Gly Gln Tyr Gln Pro Arg Pro Ser Phe
        835                 840                 845

Arg Gly Asn Lys Tyr Ser Arg Ser Tyr Arg Tyr Ala Leu Gln Asp Met
850                 855                 860

Asp Lys Phe Ser Leu Lys Asp Ser Gly Arg Gly Asp Ser Glu Ala Gly
865                 870                 875                 880

Asp Ser Asp Tyr Asp Leu Gly Arg Asp Ser Pro Ile Asp Arg Leu Leu
                885                 890                 895

Gly Glu Gly Phe Ser Asp Leu Phe Leu Thr Asp Gly Arg Ile Pro Ala
            900                 905                 910

Ala Met Arg Leu Cys Thr Glu Cys Arg Val Leu Gly His Ser Asp
        915                 920                 925

Gln Cys Trp Met Pro Pro Leu Pro Ser Pro Ser Ser Asp Tyr Arg Ser
930                 935                 940

Asn Met Phe Ile Pro Gly Glu Phe Pro Ala Gln Pro Gln Gln Gln
945                 950                 955                 960

His Ser His Gln Gly Leu Asp Asp Ser Gln Pro Ala Glu Asn Gly
                965                 970                 975

Glu Lys Lys Lys Ser Phe Ser Thr Phe Gly Lys Asp Ser Pro Ser Asp
            980                 985                 990

Glu Asp Ser Gly Asp Ser Ser Thr Ser Ser Leu Leu Ser Glu Met Ser
        995                 1000                1005

Ser Val Phe Gln Arg Leu Leu Pro Ala Ser Leu Asp Thr Phe Ser Glu
    1010                1015                1020

Cys Asn Glu Gly Asp Arg Ser Asn Ser Leu Glu Arg Arg Lys Gly Pro
1025                1030                1035                1040

Ala Gln Gly Lys Thr Gly Gly Tyr Pro Gln Gly Val Ala Ala Trp Ala
                1045                1050                1055

Ala Ser Thr His Phe Gln Asn Pro Thr Ser Ser Ser Gly Thr Pro Leu
            1060                1065                1070

Gly Thr His Ser Ser Val Gln Pro Ser Ser Lys Trp Leu Pro Ala Met
        1075                1080                1085

Glu Glu Ile Pro Glu Asn Tyr Glu Glu Asp Asp Phe Asp Asn Val Leu
    1090                1095                1100

Asn His Leu Ser Asp Gly Lys His Glu Leu Met Asp Ala Ser Glu Leu
1105                1110                1115                1120

Val Ala Glu Ile Asn Lys Leu Leu Gln Asp Val Arg Gln Ser
                1125                1130
```

<210> SEQ ID NO 19
<211> LENGTH: 6
<212> TYPE: PRT
<213> ORGANISM: Homo sapiens

<400> SEQUENCE: 19

Gln Gly Gln Tyr Gln Pro
 1               5

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 20
ttgagctctg agtggctgga gga                                      23

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
ttcccgggac acctcgggat cttc                                     24

<210> SEQ ID NO 22
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 22
caccaggggc aatttcagcc acggcca                                  27

<210> SEQ ID NO 23
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 23
aagcatggag agaagctgcg agacctc                                  27

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
ccacggaaat tgtctggttg                                          20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide -continued

```
<400> SEQUENCE: 25
tgctgcataa tcagctacgg                                              20

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
accatcactt gtctcctcgg ctgt                                         24

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
cgtcccgagg tacaaggcgg                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
cactgatacc agccaatccc                                              20

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 29
aatcaagctt gcaagagatt tgt                                          23

<210> SEQ ID NO 30
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 30
accagcgcca agaaagact                                               19

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 31
atcagcttgg ctttgaccg                                               19

<210> SEQ ID NO 32
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 32
gtgaggggca atgacaatct                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gaagagctgt cgagcctgtt                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
caggctgggt agaaggtgag                                               20

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 35
cattcacttg ggctgtgct                                                19

<210> SEQ ID NO 36
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 36
agcaacagca aggcgaaaa                                                19

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
ctggacctgt gggttgttga                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
```
catgtagggt cgagagtggg                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
cctcctgcta ctgctgacct                                              20

<210> SEQ ID NO 40
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 40
gtgctccttg tcaacagcg                                               19

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 41
ggggagtttc aggttcctgt a                                            21

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
aagtcatgct ggctccacag                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
cactgatacc agccaatccc                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
tgtgtccgtc gtggatctga                                              20

<210> SEQ ID NO 45
<211> LENGTH: 21
<212> TYPE: DNA
<213> ORGANISM: Artificial Sequence

```
<220> FEATURE:
<223> OTHER INFORMATION: Synthetic oligonucleotide

<400> SEQUENCE: 45
cctgcttcac caccttcttg a                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 46
agaggcactc ccccaaaaga t                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 47
gcaggaatga gaagaggctg a                                              21

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
tttggggcgc gattctccga                                                20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
ggactctgca ctcctccgta                                                20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
atctcgggcc gagaagctga                                                20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
cggggacacg tatctgctac                                                20
```

<210> SEQ ID NO 52
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 52
ccgtgaaaag atgacccaga tc                                               22

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53
catacccagg aaggaaggct g                                                21

<210> SEQ ID NO 54
<211> LENGTH: 2025
<212> TYPE: DNA
<213> ORGANISM: Homo sapiens

<400> SEQUENCE: 54
atgcaccaaa tgaatgctaa aatgcacttt aggtttgttt ttgcacttct gatagtatct      60
ttcaaccacg atgtactggg caagaatttg aaatacagga tttatgagga acagagggtt    120
ggatcagtaa ttgcaagact atcagaggat gtggctgatg tttttattga acttcctaat    180
ccttctactg ttcgatttcg agccatgcag aggggaaatt ctcctctact tgtagtaaac    240
gaggataatg gggaaatcag catagggggct acaattgacc gtgaacaact gtgccagaaa    300
aacttgaact gttccataga gtttgatgtg atcactctac ccacagagca tctgcagctt    360
ttccatattg aagttgaagt gctggatatt aatgacaatt ctccccagtt ttcaagatct    420
ctcatacctt tgagatatc tgagagtgca gcagttggga ctcgcattcc cctggacagt    480
gcatttgatc cagatgttgg ggaaaattcc ctccacacat actcgctctc tgccaatgat    540
ttttttaata tcgaggttcg gaccaggact gatggagcca agtatgcaga actcatagtg    600
gtcagagagt tagatcggga gctgaagtca agctacgagc ttcagctcac tgcctcagac    660
atgggagtac ctcagaggtc tggctcatcc atactaaaaa taagcatttc agactccaat    720
gacaacagcc ctgcttttga gcagcaatct tatataatac aactcttaga aaactccccg    780
gttggcactt tgctcttaga tctgaatgcc acggatccag atgagggcgc taatgggaaa    840
attgtatatt ccttcagcag tcatgtgtct cccaaaatta tggagacttt taaaattgat    900
tctgaaagag gacatttgac tcttttcaag caagtggatt atgaaatcac caaatcctat    960
gagattgatg ttcaggctca agatttgggt ccaaattcaa tcccagccca ttgcaaaatt   1020
ataattaagg ttgtggatgt taatgacaat aaacctgaaa ttaacatcaa cctcatgtcc   1080
cctggaaaag aagaaatatc ttatatttttt gaagggggatc ctattgatac atttgttgct   1140
ttggtcagag ttcaggacaa ggattctggg ctgaatggaa aatagtttg taagcttcat   1200 ggacatggtc actttaaact tcagaagaca tatgaaaaca attatttaat cttaactaat   1260
gccacactgg atagagaaaa agatctgag tatagtttga ctgtaatcgc tgaggacagg   1320
gggacaccca gtctctctac agtgaaacat tttacagttc aaatcaatga tatcaatgac   1380
aatccacccc acttccagag aagccgatat gaatttgtaa tttcagaaaa taactcacca   1440

```
-continued ggggcatata tcaccactgt tacagccaca gatcctgatc ttggagaaaa tgggcaagtg    1500
acatacacca tcttggagag ttttattcta ggaagttcca taactacata tgtaaccatt    1560
gacccatcta atggagccat ctatgccctc agaatctttg atcatgaaga agtgagtcag    1620
atcacttttg tggtagaagc aagagatgga ggaagcccga agcaactggt aagcaatacc    1680
acagttgtgc tcaccatcat tgacgaaaat gacaacgttc ctgtggttat agggcctgca    1740
ttgcgtaata atacggcaga aatcaccatt cccaaagggg ctgaaagtgg ctttcatgtc    1800
acaagaataa gggcaattga cagagactct ggtgtgaatg ctgaactcag ctgcgccata    1860
gtagcaggta atgaggagaa tatcttcata attgatccac gatcatgtga catccatacc    1920
aacgttagca tggattctgt tccctacaca gaatgggagc tgtcagttat cattcaggac    1980
aaaggcaatc ctcagctaca taccaaagtc cttctgaagt gcatg                    2025
```